(12) United States Patent
Kühnert et al.

(10) Patent No.: US 8,178,684 B2
(45) Date of Patent: *May 15, 2012

(54) SUBSTITUTED NICOTINAMIDES AS KCNQ2/3 MODULATORS

(75) Inventors: Sven Kühnert, Düren (DE); Beatrix Merla, Aachen (DE); Gregor Bahrenberg, Monschau-Konzen (DE); Wolfgang Schröder, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/720,894

(22) Filed: Mar. 10, 2010

(65) Prior Publication Data

US 2010/0234429 A1     Sep. 16, 2010

Related U.S. Application Data

(60) Provisional application No. 61/159,552, filed on Mar. 12, 2009.

(30) Foreign Application Priority Data

Mar. 12, 2009   (EP) .................................... 09003598

(51) Int. Cl.
C07D 211/72    (2006.01)
A61K 31/44     (2006.01)

(52) U.S. Cl. ........................................ 546/290; 514/345

(58) Field of Classification Search .................... None
See application file for complete search history.

(56) References Cited

U.S. PATENT DOCUMENTS

| 2002/0128277 A1 | 9/2002 | Dworetzky et al. |
| 2010/0234372 A1 | 9/2010 | Kuhnert et al. |
| 2010/0234419 A1 | 9/2010 | Kuhnert et al. |
| 2010/0234421 A1 | 9/2010 | Kuhnert et al. |
| 2010/0234428 A1 | 9/2010 | Kuhnert et al. |

FOREIGN PATENT DOCUMENTS

| EP | 0 480 258 A1 | 9/1991 |
| EP | 0 716 077 A1 | 6/1996 |
| EP | 0 900 824 A1 | 3/1999 |
| EP | 1 449 841 A1 | 8/2004 |
| FR | 2 532 939 A1 | 3/1984 |
| WO | 96 26925 A1 | 9/1996 |
| WO | 00 42026 A1 | 7/2000 |
| WO | 01 10380 A2 | 2/2001 |
| WO | 01 10381 A2 | 2/2001 |
| WO | 02 066036 A1 | 8/2002 |
| WO | 02 074388 A1 | 9/2002 |
| WO | 02 081728 A2 | 10/2002 |
| WO | 2004 026816 A1 | 4/2004 |
| WO | 2004 058704 A2 | 7/2004 |
| WO | 2004 058704 A3 | 7/2004 |
| WO | 2005 035514 A2 | 4/2005 |
| WO | 2005 105733 A1 | 11/2005 |
| WO | 2006 051311 A1 | 5/2006 |
| WO | 2006 092143 A1 | 9/2006 |
| WO | 2007 015767 A1 | 2/2007 |
| WO | 2007 030582 A2 | 3/2007 |
| WO | 2007 057447 A1 | 5/2007 |
| WO | 2008 011080 A2 | 1/2008 |
| WO | 2008 011110 A2 | 1/2008 |
| WO | 2008 012532 A2 | 1/2008 |
| WO | 2009 018466 A1 | 2/2009 |
| WO | WO 2009019149 A1 * | 2/2009 |
| WO | 2009 052078 A1 | 4/2009 |

OTHER PUBLICATIONS

Silverman, R. "The Organic Chemistry of Drug Design and Drug Action," 2004, Elsevier, pp. 28-32.*
Patani, G. et al., Chem. Rev., 1996, vol. 96, pp. 3147-3176.*
Silverman, R. "The Organic Chemistry of Drug Design and Drug Action," 2004, Elsevier, p. 9.*
Bennett et al; "A peripheral mononeuropathy in rat that produces disorders of pain sensation like those seen in man" Pain, 33 (1988) 87-107.
Gordon Blackburn-Munro; "The anticonvulsant retigabine attenuates nociceptive behaviours in rat models of persistent and neuropathic pain"; European Journal of Pharmacology 460 (2003) 109-116.
De Sarro et al; "Influence of retigabine on the anticonvulsant activity of some antiepileptic drugs against audiogenic seizures in DBA/2 mice"; Naunyn-Schmiedeberg's Arch Pharmacol (2001) 363: 330-336.
Dencker; "Effect of the new antiepileptic drug retigabine in a rodent model of mania"; ScienceDirect, Epilepsy & Behavior 12 (2008) 49-53.
Dost et al; "The anti-hyperalgesic activity of retigabine is mediated by KCNQ potassium channel activation"; Naunyn-Schmiedeberg's Arch Pharmacol (2004) 369 : 382-390.
Dubuisson et al; "The formalin test: A quantitative study of the analgesic effects of morphine, meperidine, and brain stem stimulation in rats and cats"Pain, 4 (1977) 161-174.
Gribkoff; "The therapeutic potential of neuronal Kv7 (KCNQ) channel modulators: an update"; Expert Opin. Ther. Targets (2008) 12(5): 565-581.
Gribkoff; "The therapeutic potential of neuronal KCNQ channel modulators" Expert Opin. Ther. Targets (2003) 7(6): 737-748.
Hansen et al: "The neuronal KCNQ channel opener retigabine inhibits locomotor activity and reduces forebrain excitatory responses to the psychostimulants cocaine, methylphenidate and phencyclidine"; ScienceDirect, European Journal of Pharmacology 570 (2007) 77-88.
Kim, et al; "An experimental model for peripheral neuropathy produced by segmental spinal nerve ligation in the rat"; Pain, 50 (1992) 355-363.

(Continued)

Primary Examiner — Janet Andres
Assistant Examiner — Heidi Reese
(74) Attorney, Agent, or Firm — Norris McLaughlin & Marcus, P.A.

(57) ABSTRACT

The invention relates to substituted nicotinamides, to processes for their preparation, to medicaments comprising these compounds and to the use of these compounds in the preparation of medicaments.

12 Claims, No Drawings

OTHER PUBLICATIONS

Korsgaard, et al; "Anxiolytic Effects of Maxipost (BMS-204352) and Retigabine via Activation of Neuronal Kv7 Channels"; The Journal of Pharmacology and Experimental Therapeutics vol. 314, No. 1:282-292, 2005.

Litchfield, Jr. et al; "A simplified method of evaluating dose-effect experiments"; Stamford Research Laboratories, American Cyanamid Company, Stamford, Connecticut, Royal Society of Medicine 1948; pp. 99-113.

Miceli, et al; "Molecular pharmacology and therapeutic potential of neuronal Kv7-modulating drugs"; ScienceDirect, Current Opinion in Pharmacology 2008, 8:65-74.

Nielsen, et al; "Pharmacological characterisation of acid-induced muscle allodynia in rats"; ScienceDirect, European Journal of Pharmacology 487 (2004) 93-103.

Passmore, et al; "KCNQ/M Currents in Sensory Neurons: Significance for Pain Therapy"; The Journal of Neuroscience, Aug. 6, 2003 • 23(18):7227-7236 • 7227.

Richte, et al; "Antidystonic effects of Kv7 (KCNQ) channel openers in the dtsz mutant, an animal model of primary paroxysmal dystonia"; British Journal of Pharmacology (2006) 149, 747-753.

Streng, et al; "Urodynamic effects of the K+ channel (KCNQ) opener retigabine in freely moving, conscious rats"; The Journal of Urology, vol. 172, 2054-2058, Nov. 2004.

Wickenden et al; "KCNQ potassium channels: drug targets for the treatment of epilepsy and pain"; Expert Opinion, Ther. Patents (2004) 14(4): 457-469.

Wermuth, Camille G., "Molecular Variations Based on Isosteric Replacements", The Practice of Medicinal Chemistry, (1996) 203-237.

Yoo et al, "Beckmann rearrangement using indium (III) chloride: synthesis of substituted oxazoloquinolines from the corresponding ketoximes of 3-acyl-1H-quinolin-4-ones"; Synthesis (2006), No. 10, pp. 1599-1612.

CAPLUS 1972:59403.

F. A. Carey, R. J. Sundberg, Advanced Organic Chemistry, Parts A and B, Springer, 5th edition, 2007, Tables of Contents only.

D'Amour and Smith (J. Pharm. Exp. Ther. 72, 74 79 (1941).

J. March, Advanced Organic Chemistry, Wiley & Sons, 6th edition, 2007, Table of Contents only.

Dorwald, F. Zargaoza, Side reactions in Organic Synthesis, A guide to successful synthesis design; Wiley-VCH, Weinheim, Preface, p. IS (2005).

Hewawasam, Piyasena et al, The synthesis and structure-activity relationships of 3-amino-4-benzylquinolin-2-ones: discovery of novel KCNQ2 channel openers; Bioorganic & Medicinal Chemistry Letters 14 (2004) 1615-1618.

Martin, Yvonne C., et al, Do Structurally similar molecules have similar biological activity?; J. Med. Chem. 2002, 45, 4350-4358.

* cited by examiner

SUBSTITUTED NICOTINAMIDES AS KCNQ2/3 MODULATORS

This application is a non-provisional utility patent application claiming priority of U.S. Provisional Application No. 61/159,552 filed Mar. 12, 2009; and European Patent Application No. 09003598.1.5 filed Mar. 12, 2009.

The invention relates to substituted nicotinamides, to processes for their preparation, to medicaments comprising these compounds and to the use of these compounds in the preparation of medicaments.

The treatment of pain, in particular of neuropathic pain, is of great importance in medicine. There is a worldwide need for effective pain therapies. The urgent need for action for a target-orientated treatment of chronic and non-chronic states of pain appropriate for the patient, by which is to be understood the successful and satisfactory treatment of pain for the patient, is also documented in the large number of scientific works which have recently been published in the field of applied analgesics and of fundamental research into nociception.

A pathophysiological feature of chronic pain is the over-excitability of neurons. Neuronal excitability is influenced decisively by the activity of $K^+$ channels, since these determine decisively the resting membrane potential of the cell and therefore the excitability threshold. Heteromeric $K^+$ channels of the molecular subtype KCNQ2/3 (Kv7.2/7.3) are expressed in neurons of various regions of the central (hippocampus, amygdala) and peripheral (dorsal root ganglia) nervous system and regulate the excitability thereof. Activation of KCNQ2/3 $K^+$ channels leads to a hyperpolarization of the cell membrane and, accompanying this, to a decrease in the electrical excitability of these neurons. KCNQ2/3-expressing neurons of the dorsal root ganglia are involved in the transmission of nociceptive stimuli from the periphery into the spinal marrow (Passmore et al., J. Neurosci. 2003; 23(18): 7227-36).

It has accordingly been possible to detect an analgesic activity in preclinical neuropathy and inflammatory pain models for the KCNQ2/3 agonist retigabine (Blackburn-Munro and Jensen, Eur J. Pharmacol. 2003; 460(2-3); 109-16; post et al., Naunyn Schmiedebergs Arch Pharmacol 2004; 369(4): 382-390).

The KCNQ2/3 $K^+$ channel thus represents a suitable starting point for the treatment of pain; in particular of pain selected from the group consisting of chronic pain, neuropathic pain, inflammatory pain and muscular pain (Nielsen et al., Eur J. Pharmacol. 2004; 487(1-3): 93-103), in particular of neuropathic and inflammatory pain.

Moreover, the KCNQ2/3 $K^+$ channel is a suitable target for therapy of a large number of further diseases, such as, for example, migraine (US2002/0128277), cognitive diseases (Gribkoff, Expert Opin Ther Targets 2003; 7(6): 737-748), anxiety (Korsgaard et al., J Pharmacol Exp Ther. 2005, 14(1): 282-92), epilepsy (Wickenden et al., Expert Opin Ther Pat 2004; 14(4): 457-469; Gribkoff, Expert Opin Ther Targets 2008, 12(5): 565-81; Miceli et al., Curr Opin Pharmacol 2008, 8(1): 65-74), urinary incontinence (Streng et al., J Urol 2004; 172: 2054-2058), dependency (Hansen et al., Eur J Pharmacol 2007, 570(1-3): 77-88), mania/bipolar disorders (Dencker et al., Epilepsy Behav 2008, 12(1): 49-53), dystonia-associated dyskinesias (Richter et al., Br J Pharmacol 2006, 149(6): 747-53).

There is a need for further compounds with comparable or better properties, not only in respect of affinity for KCNQ2/3 as such (potency, efficacy).

For example, it can be advantageous to improve the metabolic stability, the solubility in aqueous media or the permeability of the compounds. These factors can have a positive effect on the oral bioavailability or can change the PK/PD (pharmacokinetic/pharmacodynamic) profile, which can lead, for example, to a more advantageous duration of action.

A weak or non-existent interaction with transporter molecules, which are involved in the uptake and excretion of medicaments, is also to be categorized as an indication of improved bioavailability and low medicament interactions. Further, interactions with the enzymes that are involved in the degradation and excretion of medicaments should also be as low as possible, because such test results likewise indicate that low or no medicament interactions at all are to be expected.

It can also be advantageous for the compounds to exhibit a high selectivity in respect of other receptors of the KCNQ family (specificity), for example in respect of KCNQ1, KCNQ3/5 or KCNQ4. A high selectivity can have a positive effect on the side-effect profile. For example, it is known that compounds which (also) bind to KCNQ1 involve a high risk of cardiac side-effects, for which reason high selectivity in respect of KCNQ1 can be desirable. However, a high selectivity in respect of other receptors can also be advantageous. A low affinity for the hERG ion channel or for the L-type calcium ion channel (phenylalkylamine, benzothiazepine, dihydropyridine binding sites) can be advantageous because those receptors are associated with the occurrence of cardiac side-effects. Overall, an improved selectivity in respect of the binding to other endogenous proteins (i.e. e.g. receptors or enzymes) can lead to an improvement in the side-effect profile and hence to improved tolerability.

An object of the invention was, therefore, to provide novel compounds which have advantages over the compounds of the prior art. The compounds should be suitable in particular as pharmacological active ingredients in medicaments, especially in medicaments for the treatment of disorders or diseases that are mediated at least in part by KCNQ2/3 $K^+$ channels.

That object is achieved by the subject-matter of the patent claims.

Substituted aryl- or heteroaryl-amides which are suitable as antagonists of the $EP_4$ receptor are known from the prior art (WO 2005/105733). Also known are compounds which are suitable as inhibitors of the DPP-IV enzyme (WO 2007/015767) and of the 11-β-HSD1 enzyme (WO 2008/012532).

It has been found, surprisingly, that substituted nicotinamides of the general formula (1) below are suitable for the treatment of pain. It has further been found, surprisingly, that substituted nicotinamides of the general formula (1) below also have an excellent affinity for the KCNQ2/3 $K^+$ channel and are therefore suitable for the treatment of disorders or diseases that are mediated at least in part by KCNQ2/3 $K^+$ channels. The substituted nicotinamides thereby act as modulators, that is to say agonists or antagonists, of the KCNQ2/3 K+ channel.

The invention provides substituted nicotinamides of the general formula (1)

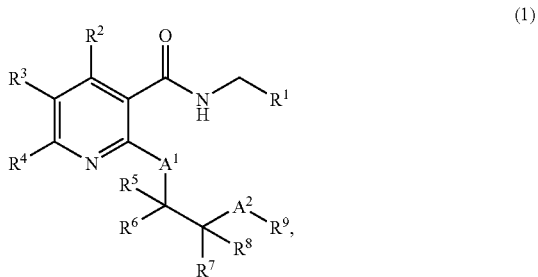

wherein
$A^1$ represents $CR^{10}R^{11}$ or S;
$A^2$ represents $CR^{12}R^{13}$, C(=O), O, S, S(=O) or S(=O)$_2$;
$R^1$ represents $C_{1-10}$-alkyl or $C_{2-10}$-heteroalkyl, in each case saturated or unsaturated, branched or unbranched, unsubstituted or mono- or poly-substituted; $C_{3-10}$-cycloalkyl or heterocyclyl, in each case saturated or unsaturated, unsubstituted or mono- or poly-substituted; aryl or heteroaryl, in each case unsubstituted or mono- or poly-substituted; $C_{1-8}$-alkyl- or $C_{2-8}$-heteroalkyl-bridged $C_{3-10}$-cycloalkyl or heterocyclyl, in each case saturated or unsaturated, unsubstituted or mono- or poly-substituted, wherein the alkyl or heteroalkyl chain can in each case be branched or unbranched, saturated or unsaturated, unsubstituted or mono- or poly-substituted; or $C_{1-8}$-alkyl- or $C_{2-8}$-heteroalkyl-bridged aryl or heteroaryl, in each case unsubstituted or mono- or poly-substituted, wherein the alkyl or heteroalkyl chain can in each case be branched or unbranched, saturated or unsaturated, unsubstituted or mono- or poly-substituted;
$R^2$, $R^3$ and $R^4$ each independently of the others represents H; F; Cl; Br; I; NO$_2$; CF$_3$; CN; OH; OCF$_3$; SH; SCF$_3$; methyl; CH$_2$—O-methyl; CH$_2$—OH; $C_{2-6}$-alkyl, O—$C_{1-6}$-alkyl, S—$C_{1-6}$-alkyl, in each case saturated or unsaturated, branched or unbranched, unsubstituted or mono- or poly-substituted; $C_{3-7}$-cycloalkyl, saturated or unsaturated, branched or unbranched, unsubstituted or mono- or poly-substituted; NR$^a$R$^b$, wherein R$^a$ and R$^b$ each independently of the other represents H or $C_{1-4}$-alkyl, saturated or unsaturated, branched or unbranched, unsubstituted or mono- or poly-substituted, or R$^a$ and R$^b$, together with the nitrogen atom joining them, form a heterocyclyl, saturated or unsaturated, branched or unbranched, unsubstituted or mono- or poly-substituted;
$R^5$, $R^6$, $R^7$, $R^8$, $R^{10}$, $R^{11}$, $R^{12}$ and $R^{13}$ each independently of the others represents H; F; Cl; Br; I; NO$_2$; CF$_3$; CN; OH; OCF$_3$; SH; SCF$_3$; $C_{1-10}$-alkyl, $C_{2-10}$-heteroalkyl, O—$C_{1-10}$-alkyl or S—$C_{1-10}$-alkyl, in each case saturated or unsaturated, branched or unbranched, unsubstituted or mono- or poly-substituted; $C_{3-10}$-cycloalkyl, saturated or unsaturated, branched or unbranched, unsubstituted or mono- or poly-substituted;
  with the proviso that when $R^5$, $R^6$, $R^7$ and $R^8$ each denotes H and $A^1$ represents S, $A^2$ may not denote S, S(=O) or S(=O)$_2$;
or $R^5$ and $R^6$ or $R^7$ and $R^8$ or $R^{10}$ and $R^{11}$ or $R^{12}$ and $R^{13}$ or $R^5$ and $R^{11}$ or $R^5$ and $R^7$ or $R^5$ and $R^{13}$ or $R^7$ and $R^{13}$ or $R^7$ and $R^{11}$ or $R^{11}$ and $R^{13}$, together with the carbon atom(s) joining them, form a $C_{3-8}$-cycloalkyl or a heterocyclyl having from three to eight ring members, in each case saturated or unsaturated, unsubstituted or mono- or poly-substituted; wherein the remaining substituents $R^5$, $R^6$, $R^7$, $R^8$, $R^{10}$, $R^{11}$, $R^{12}$ and $R^{13}$ in each case have the meaning given above;
$R^9$ represents $C_{3-10}$-cycloalkyl or heterocyclyl, in each case saturated or unsaturated, unsubstituted or mono- or poly-substituted; aryl or heteroaryl, in each case unsubstituted or mono- or poly-substituted; or represents CR$^c$R$^d$, wherein R$^c$ and R$^d$ each independently of the other denotes $C_{1-4}$-alkyl, in each case saturated or unsaturated, branched or unbranched, unsubstituted or mono- or poly-substituted;
  with the proviso that when $A^2$ represents O or S and $R^9$ represents heterocyclyl, saturated or unsaturated, unsubstituted or mono- or poly-substituted; or heteroaryl, unsubstituted or mono- or poly-substituted, the bonding of the heteroaryl or heterocyclyl takes place via a carbon atom of the heteroaryl or heterocyclyl;
wherein "alkyl substituted", "heteroalkyl substituted", "heterocyclyl substituted" and "cycloalkyl substituted" denote the substitution of one or more hydrogen atoms, in each case independently of one another, by F; Cl; Br; I; NO$_2$; CF$_3$; CN; =O; $C_{1-8}$-alkyl; $C_{2-8}$-heteroalkyl; aryl; heteroaryl; $C_{3-10}$-cycloalkyl; heterocyclyl; $C_{1-8}$-alkyl- or $C_{2-8}$-heteroalkyl-bridged aryl, heteroaryl, $C_{3-10}$-cycloalkyl or heterocyclyl; CHO; C(=O)$C_{1-8}$-alkyl; C(=O)aryl; C(=O)heteroaryl; CO$_2$H; C(=O)O—$C_{1-8}$-alkyl; C(=O)O-aryl; C(=O)O-heteroaryl; CONH$_2$; C(=O)NH—$C_{1-8}$-alkyl; C(=O)N($C_{1-8}$-alkyl)$_2$; C(=O)NH-aryl; C(=O)N(aryl)$_2$; C(=O)NH-heteroaryl; C(=O)N(heteroaryl)$_2$; C(=O)N($C_{1-8}$-alkyl)(aryl); C(=O)N($C_{1-8}$-alkyl)(heteroaryl); C(=O)N(heteroaryl)(aryl); OH; O—$C_{1-8}$-alkyl; OCF$_3$; O—($C_{1-8}$-alkyl)-OH; O—($C_{1-8}$-alkyl)-O—$C_{1-8}$-alkyl; O-benzyl; O-aryl; O-heteroaryl; O—C(=O)$C_{1-8}$-alkyl; O—C(=O)aryl; O—C(=O)heteroaryl; NH$_2$, NH—$C_{1-8}$-alkyl; N($C_{1-8}$-alkyl)$_2$; NH—C(=O)$C_{1-8}$-alkyl; N($C_{1-8}$-alkyl)-O(=O)$C_{1-8}$-alkyl; N(C(=O)$C_{1-8}$-alkyl)$_2$; NH—C(=O)-aryl; NH—C(=O)-heteroaryl; SH; S—$C_{1-8}$-alkyl; SCF$_3$; S-benzyl; S-aryl; S-heteroaryl; S(=O)$_2$$C_{1-8}$-alkyl; S(=O)$_2$aryl; S(=O)$_2$heteroaryl; S(=O)$_2$OH; S(=O)$_2$O—$C_{1-8}$-alkyl; S(=O)$_2$O-aryl; S(=O)$_2$O-heteroaryl; S(=O)$_2$—NH—$C_{1-8}$-alkyl; S(=O)$_2$—NH-aryl; and S(=O)$_2$—NH—$C_{1-8}$-heteroaryl;
wherein "aryl substituted" and "heteroaryl substituted" denote the substitution of one or more hydrogen atoms, in each case independently of one another, by F; Cl; Br; I; NO$_2$; CF$_3$; CN; $C_{1-8}$-alkyl; $C_{2-8}$-heteroalkyl; aryl; heteroaryl; $C_{3-10}$-cycloalkyl; heterocyclyl; $C_{1-8}$-alkyl- or $C_{2-8}$-heteroalkyl-bridged aryl, heteroaryl, $C_{3-10}$-cycloalkyl or heterocyclyl; CHO; C(=O)$C_{1-8}$-alkyl; C(=O)aryl; C(=O)heteroaryl; CO$_2$H; C(=O)O—$C_{1-8}$-alkyl; C(=O)O-aryl; C(=O)O-heteroaryl; CONH$_2$; C(=O)NH—$C_{1-8}$-alkyl; C(=O)N($C_{1-8}$-alkyl)$_2$; C(=O)NH-aryl; C(=O)N(aryl)$_2$; C(=O)NH-heteroaryl; C(=O)N(heteroaryl)$_2$; C(=O)N($C_{1-8}$-alkyl)(aryl); C(=O)N($C_{1-8}$-alkyl)(heteroaryl); C(=O)N(heteroaryl)(aryl); OH; O—$C_{1-8}$-alkyl; OCF$_3$; O—($C_{1-8}$-alkyl)-OH; O—($C_{1-8}$-alkyl)-O—$C_{1-8}$-alkyl; O-benzyl; O-aryl; O-heteroaryl; O—C(=O)$C_{1-8}$-alkyl; O—C(=O)aryl; O—C(=O)heteroaryl; NH$_2$, NH—$C_{1-8}$-alkyl; N($C_{1-8}$-alkyl)$_2$; NH—C(=O)$C_{1-8}$-alkyl; N($C_{1-8}$-alkyl)-O(=O)$C_{1-8}$-alkyl; N(C(=O)$C_{1-8}$-alkyl)$_2$; NH—C(=O)-aryl; NH—O(=O)-heteroaryl; SH; S—$C_{1-8}$-alkyl; SCF$_3$; S-benzyl; S-aryl; S-heteroaryl; S(=O)$_2$$C_{1-8}$-alkyl; S(=O)$_2$aryl; S(=O)$_2$heteroaryl; S(=O)$_2$OH; S(=O)$_2$O—$C_{1-8}$-alkyl; S(=O)$_2$O-aryl; S(=O)$_2$O-heteroaryl; S(=O)$_2$—NH—$C_{1-8}$-alkyl; S(=O)$_2$—NH-aryl; S(=O)$_2$—NH—$C_{1-8}$-heteroaryl;

in the form of the free compounds or salts of physiologically acceptable acids or bases.

Within the scope of this invention, the terms "alkyl" or "$C_{1-10}$-alkyl", "$C_{1-8}$-alkyl", "$C_{1-6}$-alkyl", "$C_{1-4}$-alkyl", "$C_{1-2}$-alkyl" and "$C_{2-6}$-alkyl" include acyclic saturated or unsaturated aliphatic hydrocarbon radicals, which can be branched or unbranched as well as unsubstituted or mono- or poly-substituted, having from 1 to 10 or from 1 to 8 or from 1 to 6 or from 1 to 4 or from 1 to 2 or from 2 to 6 carbon atoms, that is to say $C_{1-10}$-alkanyls, $C_{2-10}$-alkenyls and $C_{2-10}$-alkynyls or $C_{1-8}$-alkanyls, $C_{2-8}$-alkenyls and $C_{2-8}$-alkynyls or $C_{1-6}$-alkanyls, $C_{2-6}$-alkenyls and $C_{2-6}$-alkynyls or $C_{1-4}$-alkanyls, $C_{2-4}$-alkenyls and $C_{2-4}$-alkynyls or $C_{1-2}$-alkanyls, $C_2$-alkenyls and $C_2$-alkynyls or $C_{2-6}$-alkanyls, $C_{2-6}$-alkenyls and $C_{2-6}$-alkynyls. Alkenyls contain at least one C—C double bond and alkynyls contain at least one C—C triple bond. Alkyl is preferably selected from the group comprising methyl, ethyl, n-propyl, 2-propyl, n-butyl, isobutyl, sec-butyl, tert-butyl, n-pentyl, isopentyl, neopentyl, n-hexyl, n-heptyl, n-octyl, n-nonyl, n-decyl, ethenyl (vinyl), ethynyl, propenyl (—$CH_2CH=CH_2$, —$CH=CH-CH_3$, —$C(=CH_2)$—$CH_3$), propynyl (—CH—C≡CH, —C≡C—$CH_3$), butenyl, butynyl, pentenyl, pentynyl, hexenyl and hexynyl, heptenyl, heptynyl, octenyl, octynyl, nonenyl, nonynyl, decenyl and decynyl.

Within the scope of this invention, the terms "heteroalkyl" or "$C_{2-10}$-heteroalkyl" and "$C_{2-8}$-heteroalkyl" include acyclic aliphatic saturated or unsaturated hydrocarbon radicals having from 2 to 10 carbon atoms, that is to say $C_{2-10}$-heteroalkanyls, $C_{2-10}$-heteroalkenyls and $C_{2-10}$-heteroalkynyls, or having from 2 to 8 carbon atoms, that is to say $C_{2-8}$-heteroalkanyls, $C_{2-8}$-heteroalkenyls and $C_{2-8}$-heteroalkynyls, which in each case can be branched or unbranched as well as unsubstituted or mono- or poly-substituted and in which at least one carbon atom, optionally also two or three carbon atoms, have been replaced by a heteroatom or heteroatom group in each case selected independently of one another from the group consisting of O, N, NH and N($C_{1-8}$-alkyl), preferably N($CH_3$), wherein the initial carbon atom of a $C_{2-10}$-heteroalkyl or of a $C_{2-8}$-heteroalkyl, via which the $C_{2-10}$-heteroalkyl or $C_{2-8}$-heteroalkyl is bonded to the respective general structure of higher order, cannot be replaced by a heteroatom or heteroatom group and adjacent carbon atoms cannot simultaneously be replaced by a heteroatom or heteroatom group. The heteroatom groups NH and N($C_{1-8}$-alkyl) of the heteroalkyl can optionally be mono- or poly-substituted. $C_{2-10}$-Heteroalkenyls and $C_{2-8}$-heteroalkenyls contain at least one C—C or C—N double bond and $C_{2-10}$-heteroalkynyls and $C_{2-8}$-heteroalkynyls contain at least one C—C triple bond. Heteroalkyl is preferably selected from the group comprising —$CH_2$—O—$CH_3$, —$CH_2$—$CH_2$—O—$CH_3$, —$CH_2$—$CH_2$—O—$CH_2$—$CH_3$, —$CH_2$—$CH_2$—O—$CH_2$—$CH_2$—O—$CH_3$, —CH=CH—O—$CH_3$, —CH=CH—O—$CH_2$—$CH_3$, =CH—O—$CH_3$, =CH—O—$CH_2$—$CH_3$, =CH—$CH_2$—O—$CH_2$—$CH_3$, =CH—$CH_2$—O—$CH_3$, —$CH_2$—NH—$CH_3$, —$CH_2$—$CH_2$—NH—$CH_3$, —$CH_2$—$CH_2$—NH—$CH_2$—$CH_3$, —$CH_2$—$CH_2$—NH—$CH_2$—$CH_2$—NH—$CH_3$, —CH=CH—NH—$CH_3$, —CH=CH—NH—$CH_2$—$CH_3$, —CH=CH—N($CH_3$)—$CH_2$—$CH_3$, =CH—NH—$CH_3$, =CH—NH—$CH_2$—$CH_3$, =CH—$CH_2$—NH—$CH_2$—$CH_3$, =CH—$CH_2$—NH—$CH_3$, —$CH_2$—N($CH_3$)—$CH_3$, —$CH_2$—$CH_2$—N($CH_3$)—$CH_3$, —$CH_2$—$CH_2$—N($CH_3$)—$CH_2$—$CH_3$, —$CH_2$—$CH_2$—N($CH_3$)—$CH_2$—$CH_2$—N($CH_3$)—$CH_3$, —$CH_2$—$CH_2$—NH—$CH_2$—$CH_2$—O—$CH_3$, —$CH_2$—O—$CH_2$—$CH_2$—NH—$CH_3$, —$CH_2$—$CH_2$—N($CH_3$)—$CH_2$—$CH_2$—O—$CH_3$, —$CH_2$—$CH_2$—O—$CH_2$—$CH_2$—N($CH_3$)—$CH_3$, $CH_2$—N($CH_3$)—$CH_3$, $CH_2$—NH—$CH_2$—O—$CH_3$, $CH_2$—O—$CH_2$—NH—$CH_3$, $CH_2$—N($CH_3$)—$CH_2$—O—$CH_3$, $CH_2$—O—$CH_2$—N($CH_3$)—$CH_3$, —CH=CH—N($CH_3$)—$CH_3$, =CH—N($CH_3$)—$CH_3$, =CH—N($CH_3$)—$CH_2$—$CH_3$, =CH—$CH_2$—N($CH_3$)—$CH_2$—$CH_3$, =CH—$CH_2$—N($CH_3$)—$CH_3$, —$CH_2$—$CH_2$=N($CH_3$) and —$CH_2$=N($CH_3$).

For the purposes of this invention, the terms "cycloalkyl" or "$C_{3-10}$-cycloalkyl", "$C_{3-7}$-cycloalkyl" and "$C_{3-8}$-cycloalkyl" denote cyclic aliphatic hydrocarbons having 3, 4, 5, 6, 7, 8, 9 or 10 carbon atoms or having 3, 4, 5, 6 or 7 carbon atoms or having 3, 4, 5, 6, 7 or 8 carbon atoms, wherein the hydrocarbons can be saturated or unsaturated (but not aromatic), unsubstituted or mono- or poly-substituted. The bonding of the cycloalkyl to the general structure of higher order can take place via any desired and possible ring member of the cycloalkyl radical. The cycloalkyl radicals can also be fused with further saturated, (partially) unsaturated, (hetero) cyclic, aromatic or heteroaromatic ring systems, that is to say with cycloalkyl, heterocyclyl, aryl or heteroaryl, which can themselves be unsubstituted or mono- or poly-substituted. The cycloalkyl radicals can further be bridged one or more times, as, for example, in the case of adamantyl, bicyclo[2.2.1]heptyl or bicyclo[2.2.2]octyl. Cycloalkyl is preferably selected from the group comprising cyclopropyl, cyclobutyl, cyclopentyl, cyclohexyl, cycloheptyl, cyclooctyl, cyclononyl, cyclodecyl, adamantyl,

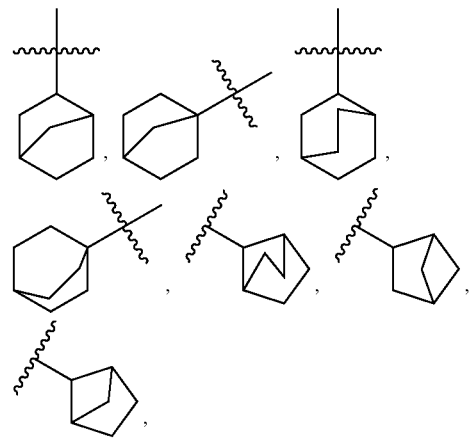

cyclopentenyl, cyclohexenyl, cycloheptenyl and cyclooctenyl.

The term "heterocyclyl" or "heterocycloalkyl" includes aliphatic saturated or unsaturated (but not aromatic) cycloalkyls having from three to ten, that is to say 3, 4, 5, 6, 7, 8, 9 or 10, ring members, in which at least one carbon atom, optionally also two or three carbon atoms, has been replaced by a heteroatom or heteroatom group in each case selected independently of one another from the group consisting of O, S, N, NH and N($C_{1-8}$-alkyl), preferably N($CH_3$), wherein the ring members can be unsubstituted or mono- or poly-substituted. The bonding of the heterocyclyl to the general structure of higher order can take place via any desired and possible ring member of the heterocyclyl radical. The heterocyclyl radicals can also be fused with further saturated, (partially) unsaturated (hetero)cyclic or aromatic or heteroaromatic ring systems, that is to say with cycloalkyl, heterocyclyl, aryl or heteroaryl, which can themselves be unsubstituted or mono- or poly-substituted. Heterocyclyl radicals are preferably selected from the group comprising azetidinyl, aziridinyl, azepanyl, azocanyl, diazepanyl, dithiolanyl, dihydroquinolinyl, dihydropyrrolyl, dioxanyl, dioxolanyl, dihydroindenyl, dihydropyridinyl, dihydrofuranyl, dihydroisoquinolinyl, dihydroindolinyl, dihydroisoindolyl, imidazolidinyl, isoxazolidinyl, morpholinyl, oxiranyl, oxetanyl, pyrrolidinyl, piperazinyl, piperidinyl, pyrazolidinyl, pyranyl, tetrahydropyrrolyl, tetrahydropyranyl, tetrahydroquinolinyl, tetrahydroisoquinolinyl, tetrahydro-indolinyl, tetrahydrofuranyl, tetrahydropyridinyl, tetrahydrothiophenyl, tetrahydro-pyridoindolyl, tetrahydronaphthyl, tetrahydrocarbolinyl, tetrahydroisoxazolopyridinyl, thiazolidinyl and thiomorpholinyl.

Within the scope of this invention, the term "aryl" denotes aromatic hydrocarbons having up to 14 ring members, inter alia phenyls and naphthyls. Each aryl radical can be unsubstituted or mono- or poly-substituted, it being possible for the aryl substituents to be identical or different and to be in any desired and possible position of the aryl. The aryl can be bonded to the general structure of higher order via any desired and possible ring member of the aryl radical. The aryl radicals can also be fused with further saturated, (partially) unsaturated, (hetero)cyclic, aromatic or heteroaromatic ring systems, that is to say with cycloalkyl, heterocyclyl, aryl or heteroaryl, which can themselves be unsubstituted or mono- or poly-substituted. Examples of fused aryl radicals are benzodioxolanyl and benzodioxanyl. Aryl is preferably selected from the group containing phenyl, 1-naphthyl and 2-naphthyl, each of which can be unsubstituted or mono- or poly-substituted. A particularly preferred aryl is phenyl, unsubstituted or mono- or poly-substituted.

The term "heteroaryl" denotes a 5- or 6-membered cyclic aromatic radical which contains at least 1 heteroatom, optionally also 2, 3, 4 or 5 heteroatoms, wherein the heteroatoms are in each case selected independently of one another from the group S, N and O and the heteroaryl radical can be unsubstituted or mono- or poly-substituted; in the case of substitution on the heteroaryl, the substituents can be identical or different and can be in any desired and possible position of the heteroaryl. Bonding to the general structure of higher order can take place via any desired and possible ring member of the heteroaryl radical. The heteroaryl can also be part of a bi- or poly-cyclic system having up to 14 ring members, wherein the ring system can be formed with further saturated, (partially) unsaturated, (hetero)cyclic or aromatic or heteroaromatic rings, that is to say with cycloalkyl, heterocyclyl, aryl or heteroaryl, which can themselves be unsubstituted or mono- or poly-substituted. It is preferred for the heteroaryl radical to be selected from the group comprising benzo-furanyl, benzoimidazolyl, benzothienyl, benzothiadiazolyl, benzothiazolyl, benzo-triazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazolyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl. Furyl, pyridyl and thienyl are particularly preferred.

Within the scope of the invention, the expressions "$C_{1-4}$- alkyl- or $C_{1-8}$-alkyl-bridged aryl, heteroaryl, heterocyclyl or cycloalkyl" mean that $C_{1-4}$-alkyl or $C_{1-8}$-alkyl and aryl or heteroaryl or heterocyclyl or cycloalkyl have the meanings defined above and the aryl or heteroaryl or heterocyclyl or cycloalkyl radical is bonded to the general structure of higher order via a $C_{1-4}$-alkyl or $C_{1-8}$-alkyl group. The alkyl chain can in all cases be saturated or unsaturated, branched or unbranched, unsubstituted or mono- or poly-substituted. $C_{1-4}$-Alkyl or $C_{1-8}$-alkyl is preferably selected from the group comprising —CH$_2$—, —CH$_2$—CH$_2$—, —CH(CH$_3$)—, —CH$_2$—CH$_2$—CH$_2$—, —CH(CH$_3$)—CH$_2$—, —CH(CH$_2$CH$_3$)—, —CH$_2$—(CH$_2$)$_2$—CH$_2$—, —CH(CH$_3$)—CH$_2$—CH$_2$—, —CH$_2$—CH(CH$_3$)—CH$_2$—, —CH(CH$_3$)—CH(CH$_3$)—, —CH(CH$_2$CH$_3$)—CH$_2$—, —C(CH$_3$)$_2$—CH$_2$—, —CH(CH$_2$CH$_2$CH$_3$)—, —C(CH$_3$)(CH$_2$CH$_3$)—, —CH$_2$—(CH$_2$)$_3$—CH$_2$—, —CH(CH$_3$)—CH$_2$—CH$_2$—CH$_2$—, —CH$_2$—CH(CH$_3$)—CH$_2$—CH$_2$—, —CH(CH$_3$)—CH$_2$—CH(CH$_3$)—, —CH(CH$_3$)—CH(CH$_3$)—CH$_2$—, —C(CH$_3$)$_2$—CH$_2$—CH$_2$—, —CH$_2$—C(CH$_3$)$_2$—CH$_2$—, —CH(CH$_2$CH$_3$)—CH$_2$—CH$_2$—, —CH$_2$—CH(CH$_2$CH$_3$)—CH$_2$—, —O(CH$_3$)$_2$—CH(CH$_3$)—, —CH(CH$_2$CH$_3$)—CH(CH$_3$)—, —C(CH$_3$)(CH$_2$CH$_3$)—CH$_2$—, —CH(CH$_2$CH$_2$CH$_3$)—CH$_2$—, —C(CH$_2$CH$_2$CH$_3$)—CH$_2$—, —CH(CH$_2$CH$_2$CH$_2$CH$_3$)—, —C(CH$_3$)(CH$_2$CH$_2$CH$_3$)—, —C(CH$_2$CH$_3$)$_2$—, —CH$_2$—(CH$_2$)$_4$—CH$_2$—, —CH=CH—, —CH=CH—CH$_2$—, —C(CH$_3$)=CH$_2$—, —CH=CH—CH$_2$—CH$_2$—, —CH$_2$—CH=CH—CH$_2$—, —CH=CH—CH=CH—, —C(CH$_3$)=CH—CH$_2$—, —CH=C(CH$_3$)—CH$_2$—, —C(CH$_3$)=C(CH$_3$)—, —C(CH$_2$CH$_3$)=CH—, —CH=CH—CH$_2$—CH$_2$—CH$_2$—, —CH$_2$—CH=CH—CH$_2$—CH$_2$—, —CH=CH=CH—CH$_2$—CH$_2$—, —CH=CH—CH$_2$—CH=CH$_2$—, —C≡O—, —C≡C—CH$_2$—, —C≡C—CH$_2$—CH$_2$—, —C≡C—CH(CH$_3$)—, —CH$_2$—C≡C—CH$_2$—, —C≡C—C≡C—, —C≡C—C(CH$_3$)$_2$—, —C≡C—CH$_2$—CH$_2$—CH$_2$—, —CH$_2$—C≡C—CH$_2$—CH$_2$—, —C≡C—C≡C—CH$_2$— and —C≡C—CH$_2$—C≡C—.

Within the scope of the invention, the expressions "$C_{2-8}$-heteroalkyl-bridged aryl, heteroaryl, heterocyclyl or cycloalkyl" mean that $C_{2-8}$-heteroalkyl and aryl or heteroaryl or heterocyclyl or cycloalkyl have the meanings defined above and the aryl or heteroaryl or heterocyclyl or cycloalkyl radical is bonded to the general structure of higher order via a $C_{2-8}$-heteroalkyl group. The heteroalkyl chain can in all cases be saturated or unsaturated, branched or unbranched, unsubstituted or mono- or poly-substituted. If a terminal carbon atom of the $C_{2-8}$-heteroalkyl group has been replaced by a heteroatom or heteroatom group, then the bonding of a heteroaryl or heterocyclyl to the heteroatom or heteroatom group of the $C_{2-8}$-heteroalkyl always takes place via a carbon atom of the heteroaryl or heterocyclyl. The terminal carbon atom is understood as being the carbon atom within the $C_{2-8}$-heteroalkyl that is furthest in the chain from the general structure of higher order. If the terminal carbon atom of a $C_{2-8}$-heteroalkyl has been replaced, for example, by an N(CH$_3$) group, that group is located within the $C_{2-8}$-heteroalkyl furthest from the general structure of higher order and is bonded to the aryl or heteroaryl or heterocyclyl or cycloalkyl radical. $C_{2-8}$-Heteroalkyl is preferably selected from the group comprising —CH$_2$—NH—, —CH$_2$—N(CH$_3$)—, —CH$_2$—O—, —CH$_2$—CH$_2$—NH—, —CH$_2$—CH$_2$—N(CH$_3$)—, —CH$_2$—CH$_2$—O—, —CH$_2$—CH$_2$—CH$_2$—NH—, —CH$_2$—CH$_2$—CH$_2$—N(CH$_3$)—, —CH$_2$—CH$_2$—CH$_2$—O—, —CH$_2$—O—CH$_2$—, —CH$_2$—CH$_2$—O—CH$_2$—, —CH$_2$—CH$_2$—O—CH$_2$—CH$_2$—, —CH$_2$—CH$_2$—O—CH$_2$—CH$_2$—O—CH$_2$—, —CH=CH—O—CH$_2$—, —CH=CH—O—CH$_2$—CH$_2$—, =CH—O—CH$_2$—, =CH—O—CH$_2$—CH$_2$—, =CH—CH$_2$—O—CH$_2$—CH$_2$—, =CH—CH$_2$—O—CH$_2$—, —CH$_2$—NH—CH$_2$—, —CH$_2$—CH$_2$—NH—CH$_2$—, —CH$_2$—CH$_2$—NH—CH$_2$—CH$_2$—, —CH$_2$—CH$_2$—NH—CH$_2$—NH—CH$_2$—, —CH=CH—NH—CH$_2$—, —CH=CH—NH—CH$_2$—CH$_2$—, —CH=CH—N(CH$_3$)—CH$_2$—CH$_2$—, =CH—

NH—CH$_2$—, =CH—NH—CH$_2$—CH$_2$—, =CH—CH$_2$—NH—CH$_2$—CH$_2$—, =CH—CH$_2$—NH—CH$_2$—, —CH$_2$—N(CH$_3$)—CH$_2$—, —CH$_2$—CH$_2$—N(CH$_3$)—CH$_2$—, —CH$_2$—CH$_2$—N(CH$_3$)—CH$_2$—CH$_2$—, —CH$_2$—CH$_2$—N(CH$_3$)—CH$_2$—CH$_2$—N(CH$_3$)—CH$_2$—CH$_2$—N(CH$_3$)—CH$_2$—, CH$_2$—CH$_2$—NH—CH$_2$—CH$_2$—O—CH$_2$—, CH$_2$—CH$_2$—O—CH$_2$—CH$_2$—NH—CH$_2$—, CH$_2$—CH$_2$—N(CH$_3$)—CH$_2$—CH$_2$—O—CH$_2$—, CH$_2$—CH$_2$—O—CH$_2$—CH$_2$—N(CH$_3$)—CH$_2$—, CH$_2$—NH—CH$_2$—O—CH$_2$—, CH$_2$—O—CH$_2$—NH—CH$_2$—, CH$_2$—N(CH$_3$)—CH$_2$—O—CH$_2$—, CH$_2$—O—CH$_2$—N(CH$_3$)—CH$_2$—, —CH=CH—N(CH$_3$)—CH$_2$—, =CH—N(CH$_3$)—CH$_2$—, =CH—N(CH$_3$)—CH$_2$—CH$_2$—, =CH—CH$_2$—N(CH$_3$)—CH$_2$—CH$_2$— and =CH—CH$_2$—N(CH$_3$)—CH$_2$—.

In connection with "alkyl", "heteroalkyl", "heterocyclyl" and "cycloalkyl", the expression "mono- or poly-substituted" is understood as meaning within the scope of this invention the substitution of one or more hydrogen atoms one or more times, for example two, three or four times, in each case independently of one another, by substituents selected from the group comprising F; Cl; Br; I; NO$_2$; CF$_3$; CN; =O; C$_{1-8}$-alkyl; C$_{2-8}$-heteroalkyl; aryl; heteroaryl; C$_{3-10}$-cycloalkyl; heterocyclyl; C$_{1-8}$-alkyl- or C$_{2-8}$-heteroalkyl-bridged aryl, heteroaryl, C$_{3-10}$-cycloalkyl or heterocyclyl; CHO; C(=O)C$_{1-8}$-alkyl; C(=O)aryl; C(=O)heteroaryl; CO$_2$H; C(=O)O—C$_{1-8}$-alkyl; C(=O)O-aryl; C(=O)O-heteroaryl; CONH$_2$; C(=O)NH—C$_{1-8}$-alkyl; C(=O)N(C$_{1-8}$-alkyl)$_2$; C(=O)NH-aryl; C(=O)N(aryl)$_2$; C(=O)NH-heteroaryl; C(=O)N(heteroaryl)$_2$; C(=O)N(C$_{1-8}$-alkyl)(aryl); C(=O)N(C$_{1-8}$-alkyl)(heteroaryl); C(=O)N(heteroaryl)(aryl); OH; O—C$_{1-8}$-alkyl; OCF$_3$; 0-(C$_{1-8}$-alkyl)-OH; O—(C$_{1-8}$-alkyl)-O—C$_{1-8}$-alkyl; O-benzyl; O-aryl; O-heteroaryl; O—C(=O)C$_{1-8}$-alkyl; O—C(=O)aryl; O—C(=O)heteroaryl; NH$_2$, NH—C$_{1-8}$-alkyl; N(C$_{1-8}$-alkyl)$_2$; NH—C(=O)C$_{1-8}$-alkyl; N(C$_{1-8}$-alkyl)-C(=O)C$_{1-8}$-alkyl; N(C(=O)C$_{1-8}$-alkyl)$_2$; NH—C(=O)-aryl; NH—C(=O)-heteroaryl; SH; S—C$_{1-8}$-alkyl; SCF$_3$; S-benzyl; S-aryl; S-heteroaryl; S(=O)$_2$C$_{1-8}$-alkyl; S(=O)$_2$aryl; S(=O)$_2$heteroaryl; S(=O)$_2$OH; S(=O)$_2$O—C$_{1-8}$-alkyl; S(=O)$_2$O-aryl; S(=O)$_2$O-heteroaryl; S(=O)$_2$—NH—C$_{1-8}$-alkyl; S(=O)$_2$—NH-aryl; and S(=O)$_2$—NH—C$_{1-8}$-heteroaryl; wherein polysubstituted radicals are to be understood as being radicals that are substituted several times, for example two, three or four times, either on different atoms or on the same atom, for example three times on the same carbon atom, as in the case of CF$_3$ or CH$_2$CF$_3$, or at different places, as in the case of CH(OH)—CH=CH—CHCl$_2$. A substituent can itself optionally be mono- or poly-substituted. Polysubstitution can take place with the same or with different substituents.

Preferred "alkyl", "heteroalkyl", "heterocyclyl" and "cycloalkyl" substituents are selected from the group comprising F; Cl; Br; I; NO$_2$; CH$_2$CF$_3$; CF$_3$; CN; C$_{1-8}$-alkyl; C$_{2-8}$-heteroalkyl; phenyl; naphthyl; pyridyl; thienyl; furyl; C$_{3-10}$-cycloalkyl; heterocyclyl; C$_{1-8}$-alkyl- or C$_{2-8}$-heteroalkyl-bridged phenyl, naphthyl, pyridyl, thienyl, furyl, cycloalkyl or heterocyclyl; CHO; C(=O)C$_{1-8}$-alkyl; CO$_2$H; C(=O)O—C$_{1-8}$-alkyl; CONH$_2$; C(=O)NH—C$_{1-8}$-alkyl; C(=O)N(C$_{1-8}$-alkyl)$_2$; OH; =O; O—C$_{1-8}$-alkyl; OCF$_3$; O—(C$_{1-8}$-alkyl)-OH; O—(C$_{1-8}$-alkyl)-O—C$_{1-8}$-alkyl; O-benzyl; O-phenyl; O-heteroaryl; O—C(=O)C$_{1-8}$-alkyl; NH$_2$, NH—C$_{1-8}$-alkyl; N(C$_{1-8}$-alkyl)$_2$; NH—C(=O)C$_{1-8}$-alkyl; N(C$_{1-8}$-alkyl)-O(=O)C$_{1-8}$-alkyl; N(C(=O)C$_{1-8}$-alkyl)$_2$; SH; S—C$_{1-8}$-alkyl; SCF$_3$; S-benzyl; S-phenyl; S-heteroaryl; S(=O)$_2$C$_{1-8}$-alkyl; S(=O)$_2$OH; S(=O)$_2$O—C$_{1-8}$-alkyl; S(=O)$_2$—NH—C$_{1-8}$-alkyl.

In connection with "aryl" and "heteroaryl", "mono- or poly-substituted" is understood within the scope of this invention as meaning the substitution of one or more hydrogen atoms of the ring system one or more times, for example two, three or four times, in each case independently of one another, by substituents selected from the group comprising F; Cl; Br; I; NO$_2$; CF$_3$; CN; C$_{1-8}$-alkyl; C$_{2-8}$-heteroalkyl; aryl; heteroaryl; C$_{3-10}$-cycloalkyl; heterocyclyl; C$_{1-8}$-alkyl- or C$_{2-8}$-heteroalkyl-bridged aryl, heteroaryl, C$_{3-10}$-cycloalkyl or heterocyclyl; CHO; C(=O)C$_{1-8}$-alkyl; C(=O)aryl; C(=O)heteroaryl; CO$_2$H; C(=O)O—C$_{1-8}$-alkyl; C(=O)O-aryl; C(=O)O-heteroaryl; CONH$_2$; C(=O)NH—C$_{1-8}$-alkyl; C(=O)N(C$_{1-8}$-alkyl)$_2$; C(=O)NH-aryl; C(=O)N(aryl)$_2$; C(=O)NH-heteroaryl; C(=O)N(heteroaryl)$_2$; C(=O)N(C$_{1-8}$-alkyl)(aryl); C(=O)N(C$_{1-8}$-alkyl)(heteroaryl); C(=O)N(heteroaryl)(aryl); OH; O—C$_{1-8}$-alkyl; OCF$_3$; O—(C$_{1-8}$-alkyl)-OH; O—(C$_{1-8}$-alkyl)-O—C$_{1-8}$-alkyl; O-benzyl; O-aryl; O-heteroaryl; O—C(=O)C$_{1-8}$-alkyl; O—C(=O)aryl; O—C(=O)heteroaryl; NH$_2$, NH—C$_{1-8}$-alkyl; N(C$_{1-8}$-alkyl)$_2$; NH—C(=O)C$_{1-8}$-alkyl; N(C$_{1-8}$-alkyl)-O(=O)C$_{1-8}$-alkyl; N(C(=O)C$_{1-8}$-alkyl)$_2$; NH—O(=O)-aryl; NH—C(=O)-heteroaryl; SH; S—C$_{1-8}$-alkyl; SCF$_3$; S-benzyl; S-aryl; S-heteroaryl; S(=O)$_2$C$_{1-8}$-alkyl; S(=O)$_2$aryl; S(=O)$_2$heteroaryl; S(=O)$_2$OH; S(=O)$_2$O—C$_{1-8}$-alkyl; S(=O)$_2$O-aryl; S(=O)$_2$O-heteroaryl; S(=O)$_2$—NH—C$_{1-8}$-alkyl; S(=O)$_2$—NH-aryl; S(=O)$_2$—NH—C$_{1-8}$-heteroaryl; on one atom or optionally on different atoms, wherein a substituent can itself optionally be mono- or poly-substituted. Polysubstitution is carried out with the same or with different substituents.

Preferred "aryl" and "heteroaryl" substituents are F; Cl; Br; I; NO$_2$; CH$_2$CF$_3$; CF$_3$; CN; C$_{1-8}$-alkyl; C$_{2-8}$-heteroalkyl; phenyl; naphthyl; pyridyl; thienyl; furyl; C$_{3-10}$-cycloalkyl; heterocyclyl; C$_{1-8}$-alkyl- or C$_{2-8}$-heteroalkyl-bridged phenyl, naphthyl, pyridyl, thienyl, furyl, C$_{3-10}$-cycloalkyl or heterocyclyl; CHO; C(=O)C$_{1-8}$-alkyl; CO$_2$H; C(=O)O—C$_{1-8}$-alkyl; CONH$_2$; C(=O)NH—C$_{1-8}$-alkyl; C(=O)N(C$_{1-8}$-alkyl)$_2$; OH; O—C$_{1-8}$-alkyl; OCF$_3$; O—(C$_{1-8}$-alkyl)-OH; O—(C$_{1-8}$-alkyl)-O—C$_{1-8}$-alkyl; O-benzyl; O-phenyl; O-heteroaryl; O—C(=O)C$_{1-8}$-alkyl; NH$_2$, NH—C$_{1-8}$-alkyl; N(C$_{1-8}$-alkyl)$_2$; NH—C(=O)C$_{1-8}$-alkyl; N(C$_{1-8}$-alkyl)-O(=O)C$_{1-8}$-alkyl; N(C(=O)C$_{1-8}$-alkyl)$_2$; SH; S—C$_{1-8}$-alkyl; SCF$_3$; S-benzyl; S-phenyl; S-heteroaryl; S(=O)$_2$C$_{1-8}$-alkyl; S(=O)$_2$OH; S(=O)$_2$O—C$_{1-8}$-alkyl; S(=O)$_2$—NH—C$_{1-8}$-alkyl.

The compounds according to the invention are defined by substituents, for example by R$^1$, R$^2$ and R$^3$ (1st generation substituents), which are themselves optionally substituted (2nd generation substituents). Depending on the definition, these substituents of the substituents can in turn themselves be substituted (3rd generation substituents). If, for example, R$^1$=aryl (1st generation substituent), aryl can itself be substituted, for example by C$_{1-8}$-alkyl (2nd generation substituent). This yields the functional group aryl-C$_{1-8}$-alkyl. C$_{1-8}$-Alkyl can then in turn itself be substituted, for example by Cl (3rd generation substituent). Overall, this then yields the functional group aryl-C$_{1-8}$-alkyl-Cl.

In a preferred embodiment, however, the 3rd generation substituents cannot themselves be substituted, that is to say there are no 4th generation substituents.

In another preferred embodiment, the 2nd generation substituents cannot themselves be substituted, that is to say there are not even any 3rd generation substituents. In other words, in this embodiment, for example in the case of the general formula (1), the functional groups for R$^1$ to R$^{13}$ can in each case optionally be substituted, but the substituents in each case cannot themselves be substituted.

In some cases, the compounds according to the invention are defined by substituents which are or carry an aryl or heteroaryl radical, in each case unsubstituted or mono- or poly-substituted, or which, together with the carbon atom(s) or heteroatom(s) joining them as ring member(s), form a ring, for example an aryl or heteroaryl, in each case unsubstituted or mono- or poly-substituted. Both these aryl or heteroaryl radicals and the aromatic ring systems so formed can optionally be fused with $C_{3-10}$-cycloalkyl or heterocyclyl, in each case saturated or unsaturated, that is to say with a $C_{3-10}$-cycloalkyl such as cyclopentyl or with a heterocyclyl such as morpholinyl, it being possible for the $C_{3-10}$-cycloalkyl or heterocyclyl radicals so fused to be unsubstituted or mono- or poly-substituted.

In some cases, the compounds according to the invention are defined by substituents which are or carry a $C_{3-10}$-cycloalkyl or heterocyclyl radical, in each case unsubstituted or mono- or poly-substituted, or which, together with the carbon atom(s) or heteroatom(s) joining them as ring member(s), form a ring, for example a $C_{3-10}$-cycloalkyl or heterocyclyl, in each case unsubstituted or mono- or poly-substituted. Both these $C_{3-10}$-cycloalkyl or heterocyclyl radicals and the aliphatic ring systems formed can optionally be fused with aryl or heteroaryl, that is to say with an aryl such as phenyl or with a heteroaryl such as pyridyl, it being possible for the aryl or heteroaryl radicals so fused to be unsubstituted or mono- or poly-substituted.

Within the scope of the present invention, the symbol

used in formulae denotes a linking of a corresponding radical to the general structure of higher order.

The expression "salt formed with a physiologically acceptable acid" is understood within the scope of this invention as meaning salts of the active ingredient in question with inorganic or organic acids that are physiologically acceptable—in particular when used in humans and/or mammals. The hydrochloride is particularly preferred. Examples of physiologically acceptable acids are: hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, saccharinic acid, monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, hippuric acid, phosphoric acid and/or aspartic acid. Citric acid and hydrochloric acid are particularly preferred.

Physiologically acceptable salts with cations or bases are salts of the compound in question—in the form of the anion with at least one, preferably inorganic cation—that are physiologically acceptable—in particular when used in humans and/or mammals. Particular preference is given to the salts of the alkali and alkaline earth metals but also to ammonium salts, but in particular to (mono-) or (di-)sodium, (mono-) or (di-)potassium, magnesium or calcium salts.

In preferred embodiments of the compounds of the general formula (1) according to the invention $A^1$ represents S and $A^2$ represents $CR^{12}R^{13}$, O, S or $S(=O)_2$, preferably $CR^{12}R^{13}$, S or $S(=O)_2$, particularly preferably $CR^{12}R^{13}$.

Further preferred embodiments of the compounds of the general formula (1) according to the invention have the general formula (1a), (1b), (1c), (1d), (1e) or (1f):

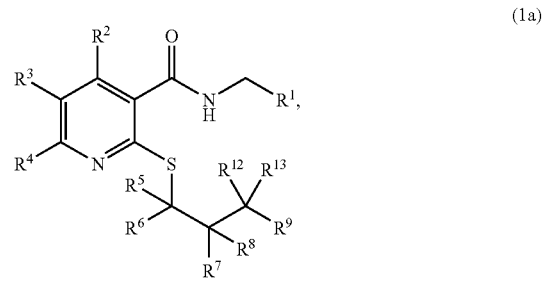
(1a)

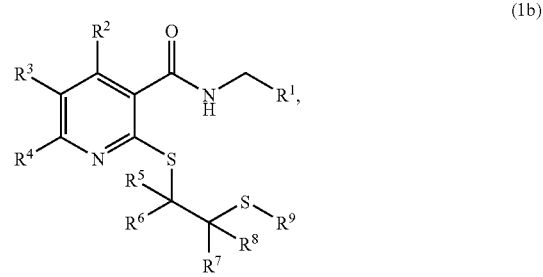
(1b)

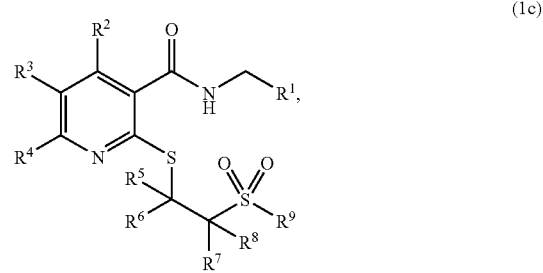
(1c)

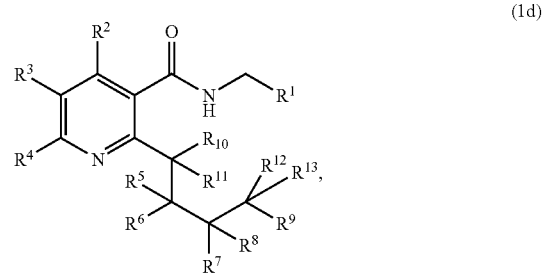
(1d)

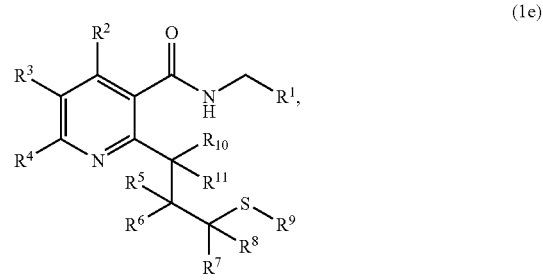
(1e)

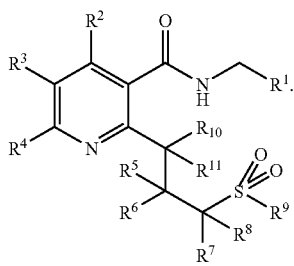

(1f)

Compounds of the general formulae (1a), (1 b) and (1c) are most particularly preferred.

Compounds of the general formula (1a) are especially preferred.

In a further preferred embodiment the radical $R^1$ represents $C_{1-10}$-alkyl or $C_{2-10}$-heteroalkyl, in each case saturated or unsaturated, branched or unbranched, unsubstituted or mono- or poly-substituted by one or more substituents each selected independently of one another from the group consisting of F, Cl, Br, I, $NO_2$, $CF_3$, CN, OH, =O, C(=O)—OH, $OCF_3$, $NH_2$, $S(=O)_2OH$, SH, $SCF_3$, $C_{1-8}$-alkyl, O—$C_{1-8}$-alkyl, S—$C_{1-8}$-alkyl, NH—$C_{1-8}$-alkyl, $N(C_{1-8}$-alkyl$)_2$, $C_{3-10}$-cycloalkyl and heterocyclyl, wherein the above alkyl radicals can in each case be saturated or unsaturated, branched or unbranched, unsubstituted or mono- or poly-substituted by one or more substituents each selected independently of one another from the group consisting of F, Cl, Br, I, O—$C_{1-8}$-alkyl, OH and $OCF_3$, and wherein $C_{3-10}$-cycloalkyl or heterocyclyl can in each case be saturated or unsaturated, unsubstituted or mono- or poly-substituted by one or more substituents each selected independently of one another from the group consisting of F, Cl, Br, I, $C_{1-8}$-alkyl, OH, =O, O—$C_{1-8}$-alkyl, $OCF_3$, $NH_2$, NH—$C_{1-8}$-alkyl and $N(C_{1-8}$-alkyl$)_2$;

$C_{3-10}$-cycloalkyl or heterocyclyl, in each case saturated or unsaturated, unsubstituted or mono- or poly-substituted by one or more substituents each selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$, $S(=O)_2OH$, benzyl, phenyl, pyridyl and thienyl, wherein benzyl, phenyl, pyridyl, thienyl can in each case be unsubstituted or mono- or poly-substituted by one or more substituents selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$ and $S(=O)_2OH$;

aryl or heteroaryl, in each case unsubstituted or mono- or poly-substituted by one or more substituents each selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$, $S(=O)_2OH$, benzyl, phenyl, pyridyl and thienyl, wherein benzyl, phenyl, pyridyl, thienyl can in each case be unsubstituted or mono- or poly-substituted by one or more substituents selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$ and $S(=O)_2OH$, $C_{1-8}$-alkyl- or $C_{2-8}$-heteroalkyl-bridged $C_{3-10}$-cycloalkyl or heterocyclyl, in each case saturated or unsaturated, unsubstituted or mono- or poly-substituted by one or more substituents each selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$, $S(=O)_2OH$, benzyl, phenyl, pyridyl and thienyl, wherein benzyl, phenyl, pyridyl, thienyl can in each case be unsubstituted or mono- or poly-substituted by one or more substituents selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$ and $S(=O)_2OH$;

wherein the alkyl or heteroalkyl chain can in each case be branched or unbranched, saturated or unsaturated, unsubstituted or mono- or poly-substituted by one or more substituents each selected independently of one another from the group consisting of F, Cl, Br, I, $NO_2$, $CF_3$, CN, OH, =O, C(=O)—OH, $OCF_3$, $NH_2$, $S(=O)_2OH$, SH, $SCF_3$, $C_{1-8}$-alkyl, 0-$C_{1-8}$-alkyl, S—$C_{1-8}$-alkyl, NH—$C_{1-8}$-alkyl, $N(C_{1-8}$-alkyl$)_2$, $C_{3-10}$-cycloalkyl and heterocyclyl, wherein the above alkyl radicals can in each case be saturated or unsaturated, branched or unbranched, unsubstituted or mono- or poly-substituted by one or more substituents each selected independently of one another from the group consisting of F, Cl, Br, I, O—$C_{1-8}$-alkyl, OH and $OCF_3$, and wherein $C_{3-10}$-cycloalkyl or heterocyclyl can in each case be saturated or unsaturated, unsubstituted or mono- or poly-substituted by one or more substituents each selected independently of one another from the group consisting of F, Cl, Br, I, $C_{1-8}$-alkyl, OH, =O, O—$C_{1-8}$-alkyl, $OCF_3$, $NH_2$, NH—$C_{1-8}$-alkyl and $N(C_{1-8}$-alkyl$)_2$;

or $C_{1-8}$-alkyl- or $C_{2-8}$-heteroalkyl-bridged aryl or heteroaryl, in each case unsubstituted or mono- or poly-substituted by one or more substituents each selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$, $S(=O)_2OH$, benzyl, phenyl, pyridyl and thienyl, wherein benzyl, phenyl, pyridyl, thienyl can in each case be unsubstituted or mono- or poly-substituted by one or more substituents selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$ and $S(=O)_2OH$;

wherein the alkyl or heteroalkyl chain can in each case be branched or unbranched, saturated or unsaturated, unsubstituted or mono- or poly-substituted by one or more substituents each selected independently of one another from the group consisting of F, Cl, Br, I, $NO_2$, $CF_3$, CN, OH, =O, C(=O)—OH, $OCF_3$, $NH_2$, $S(=O)_2OH$, SH, $SCF_3$, $C_{1-8}$-alkyl, 0-$C_{1-8}$-alkyl, S—$C_{1-8}$-alkyl, NH—$C_{1-8}$-alkyl, $N(C_{1-8}$-alkyl$)_2$, $C_{3-10}$-cycloalkyl and heterocyclyl, wherein the above alkyl radicals can in each case be saturated or unsaturated, branched or unbranched, unsubstituted or mono- or poly-substituted by one or more substituents each selected independently of one another from the group consisting of F, Cl, Br, I, O—$C_{1-8}$-alkyl, OH and $OCF_3$, and wherein $C_{3-10}$-cycloalkyl or heterocyclyl can in each case be saturated or unsaturated, unsubstituted or mono- or poly-substituted by one or more substituents each selected independently of one another from the group consisting of F, Cl, Br, I, $C_{1-8}$-alkyl, OH, =O, O—$C_{1-8}$-alkyl, $OCF_3$, $NH_2$, NH—$C_{1-8}$-alkyl and $N(C_{1-8}$-alkyl$)_2$.

In a further preferred embodiment the substituent $R^1$ represents the following partial structure (T1)

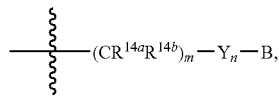
(T1)

wherein
$R^{14a}$ and $R^{14b}$ each independently of the other represents H; F; Cl; Br; I; $NO_2$; $CF_3$; CN; OH; $OCF_3$; $NH_2$; $C_{1-4}$-alkyl, O-$C_{1-4}$-alkyl, NH—$C_{1-4}$-alkyl, N($C_{1-4}$-alkyl)$_2$, in each case saturated or unsaturated, branched or unbranched, unsubstituted or mono- or poly-substituted by one or more substituents each selected independently of one another from the group consisting of F, Cl, Br, I, O—$C_{1-4}$-alkyl, OH and $OCF_3$; $C_{3-10}$-cycloalkyl or heterocyclyl, in each case saturated or unsaturated, unsubstituted or mono- or poly-substituted by one or more substituents each selected independently of one another from the group consisting of F, Cl, Br, I, $C_{1-4}$-alkyl, OH, =O, O—$C_{1-4}$-alkyl, $OCF_3$, $NH_2$, NH—$C_{1-4}$-alkyl and N($C_{1-4}$-alkyl)$_2$;

m represents 0, 1, 2 or 3;

Y represents O or $NR^{15}$,
wherein $R^{15}$ represents H; $C_{1-4}$-alkyl, saturated or unsaturated, branched or unbranched, unsubstituted or mono- or poly-substituted by one or more substituents each selected independently of one another from the group consisting of F, Cl, Br, I, $C_{1-4}$-alkyl, OH, O—$C_{1-4}$-alkyl, $OCF_3$, $NH_2$, NH—$C_{1-4}$-alkyl and N($C_{1-4}$-alkyl)$_2$; or represents $C_{3-10}$-cycloalkyl, saturated or unsaturated, unsubstituted or mono- or poly-substituted by one or more substituents each selected independently of one another from the group consisting of F, Cl, Br, I, $C_{1-4}$-alkyl, OH, O—$C_{1-4}$-alkyl, $OCF_3$, $NH_2$, NH—$C_{1-4}$-alkyl and N($C_{1-4}$-alkyl)$_2$;

n represents 0 or 1,

B represents $C_{1-8}$-alkyl, saturated or unsaturated, branched or unbranched, unsubstituted or mono- or poly-substituted by one or more substituents each selected independently of one another from the group consisting of F, Cl, Br, I, $NO_2$, CN, OH, =O, O—$C_{1-4}$-alkyl, $OCF_3$, C(=O)—OH, $CF_3$, $NH_2$, NH($C_{1-4}$-alkyl), N($C_{1-4}$-alkyl)$_2$, SH, S—$C_{1-4}$-alkyl, $SCF_3$ and S(=O)$_2$OH; $C_{3-10}$-cycloalkyl or heterocyclyl, in each case saturated or unsaturated, unsubstituted or mono- or poly-substituted by one or more substituents each selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, NH($C_{1-8}$-alkyl), N($C_{1-8}$-alkyl)$_2$, SH, S—$C_{1-8}$-alkyl, $SCF_3$, S(=O)$_2$OH; benzyl, phenyl, pyridyl and thienyl, wherein benzyl, phenyl, pyridyl, thienyl can in each case be unsubstituted or mono- or poly-substituted by one or more substituents selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, NH($C_{1-8}$-alkyl), N($C_{1-8}$-alkyl)$_2$, SH, S—$C_{1-8}$-alkyl, $SCF_3$ and S(=O)$_2$OH; aryl or heteroaryl, in each case unsubstituted or mono- or poly-substituted by one or more substituents each selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, NH($C_{1-8}$-alkyl), N($C_{1-8}$-alkyl)$_2$, SH, S—$C_{1-8}$-alkyl, $SCF_3$, S(=O)$_2$OH, benzyl, phenyl, pyridyl and thienyl, wherein benzyl, phenyl, pyridyl, thienyl can in each case be unsubstituted or mono- or poly-substituted by one or more substituents selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, NH($C_{1-8}$-alkyl), N($C_{1-8}$-alkyl)$_2$, SH, S—$C_{1-8}$-alkyl, $SCF_3$ and S(=O)$_2$OH.

Preferably, $R^{14a}$ and $R^{14b}$ each independently of the other represents H; F; Cl; Br; I; $NO_2$; $CF_3$; $CH_2CF_3$; CN; OH; $OCF_3$; $NH_2$; $C_{1-4}$-alkyl, O—$C_{1-4}$-alkyl, O—$C_{1-4}$-alkyl-OH, O—$C_{1-4}$-alkyl-OCH$_3$, NH—$C_{1-4}$-alkyl, N($C_{1-4}$-alkyl)$_2$, in each case saturated or unsaturated, branched or unbranched, unsubstituted; $C_{3-10}$-cycloalkyl, saturated or unsaturated, unsubstituted or mono- or poly-substituted by one or more substituents each selected independently of one another from the group consisting of F, Cl, Br, I, $C_{1-4}$-alkyl, OH, O—$C_{1-4}$-alkyl;

m represents 0, 1, 2 or 3;

Y represents O or $NR^{15}$;
wherein $R^{15}$ represents H; $C_{1-4}$-alkyl, saturated or unsaturated, unsubstituted; or represents $C_{3-10}$-cycloalkyl, saturated or unsaturated, unsubstituted;

n represents 0 or 1;

B represents $C_{1-8}$-alkyl, saturated or unsaturated, branched or unbranched, unsubstituted or mono- or poly-substituted by one or more substituents each selected independently of one another from the group consisting of F, Cl, Br, I, $NO_2$, CN, OH, O—$C_{1-4}$-alkyl, $OCF_3$, $CF_3$, $NH_2$, NH($C_{1-4}$-alkyl), N($C_{1-4}$-alkyl)$_2$, $SCF_3$; $C_{3-10}$-cycloalkyl or heterocyclyl, in each case saturated or unsaturated, unsubstituted or mono- or poly-substituted by one or more substituents each selected independently of one another from the group consisting of F, Cl, Br, I, $NO_2$, CN, OH, O—$C_{1-4}$-alkyl, $OCF_3$, $C_{1-4}$-alkyl, $CF_3$, $NH_2$, NH($C_{1-4}$-alkyl), N($C_{1-4}$-alkyl)$_2$, $SCF_3$; aryl or heteroaryl, in each case unsubstituted or mono- or poly-substituted by one or more substituents each selected independently of one another from the group consisting of F, Cl, Br, I, $NO_2$, CN, OH, O—$C_{1-4}$-alkyl, $OCF_3$, $C_{1-4}$-alkyl, C(=O)—OH, $CF_3$, $NH_2$, NH($C_{1-4}$-alkyl), N($C_{1-4}$-alkyl)$_2$, SH, S—$C_{1-4}$-alkyl, $SCF_3$, S(=O)$_2$OH, benzyl, phenyl and pyridyl, wherein benzyl, phenyl or pyridyl are in each case unsubstituted or mono- or poly-substituted by one or more substituents each selected independently of one another from the group consisting of F, Cl, Br, I, $NO_2$, CN, OH, O—$C_{1-4}$-alkyl, $OCF_3$, $C_{1-4}$-alkyl, C(=O)—OH, $CF_3$, $NH_2$, NH($C_{1-4}$-alkyl), N($C_{1-4}$-alkyl)$_2$, SH, S—$C_{1-4}$-alkyl, $SCF_3$ and S(=O)$_2$OH.

Particularly preferably, $R^{14a}$ and $R^{14b}$ each independently of the other represents H; F; Cl; Br; I; $NO_2$; $CF_3$; CN; methyl; ethyl; n-propyl; isopropyl; cyclopropyl; n-butyl; sec-butyl; tert-butyl; $CH_2CF_3$; OH; O-methyl; O-ethyl; O—(CH$_2$)$_2$—O—CH$_3$; O—(CH$_2$)$_2$—OH; $OCF_3$; $NH_2$; NH-methyl; N(methyl)$_2$; NH-ethyl; N(ethyl)$_2$; or N(methyl)(ethyl);

m represents 0, 1 or 2;

n represents 0; and

B represents $C_{1-4}$-alkyl, saturated, branched or unbranched, unsubstituted or mono- or poly-substituted by one or more substituents each selected independently of one another from the group consisting of F, Cl, Br, I, OH, O—$C_{1-4}$-alkyl, $OCF_3$ and $CF_3$; $C_{3-10}$-cycloalkyl, saturated, unsubstituted; phenyl, naphthyl, pyridyl, thienyl, in each case unsubstituted or mono- or di- or tri-substituted by one, two or three substituents each selected independently of one another from the group consisting of F, Cl, Br, I, $NO_2$, CN, OH, O—$C_{1-4}$-alkyl, $OCF_3$, $C_{1-4}$-alkyl, C(=O)—OH, $CF_3$, $NH_2$, NH($C_{1-4}$-alkyl), N($C_{1-4}$-alkyl)$_2$, SH, S—$C_{1-4}$-alkyl, $SCF_3$, S(=O)$_2$OH.

Most particularly preferably, $R^{14a}$ and $R^{14b}$ each independently of the other represents H; F; Cl; Br; I; methyl; ethyl;

n-propyl; isopropyl; n-butyl; sec-butyl; tert-butyl; OH; O-methyl; O-ethyl; O—(CH$_2$)$_2$—O—CH$_3$; or O—(CH$_2$)$_2$—OH;

m represents 0, 1 or 2;

n represents 0; and

B represents methyl; ethyl; n-propyl; isopropyl; n-butyl; sec-butyl; tert-butyl;

cyclopropyl; cyclobutyl; cyclopentyl; cyclohexyl; cycloheptyl; adamantyl; bicyclo[2.2.1]heptyl; bicyclo[2.2.2]octyl; phenyl, pyridyl, thienyl, in each case unsubstituted or mono-, di- or tri-substituted by one, two or three substituents each selected independently of one another from the group consisting of F, Cl, Br, I, NO$_2$, CN, OH, O—C$_{1-4}$-alkyl, OCF$_3$, C$_{1-4}$-alkyl, C(=O)—OH, CF$_3$, NH$_2$, NH(C$_{1-4}$-alkyl), N(C$_{1-4}$-alkyl)$_2$, SH, S—C$_{1-4}$-alkyl, SCF$_3$ and S(=O)$_2$OH.

For n=0, the partial structure (T-1) for R$^1$ yields the partial structure (T1-1):

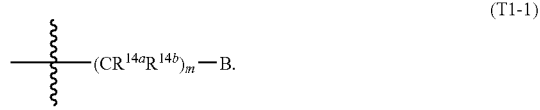

(T1-1)

In a preferred embodiment for n=0, R$^{14a}$ and R$^{14b}$ each independently of the other represents H; F; Cl; Br; I; methyl; ethyl; n-propyl; isopropyl; n-butyl; sec-butyl; tert-butyl; OH; O-methyl; O-ethyl; O—(CH$_2$)$_2$—O—CH$_3$; or O—(CH$_2$)$_2$—OH.

In a preferred embodiment for m=0, B represents phenyl, pyridyl or thienyl, mono- or di- or tri-substituted by one, two or three substituents each selected independently of one another from the group consisting of F, Cl, Br, I, NO$_2$, CN, OH, O—C$_{1-4}$-alkyl, OCF$_3$, C$_{1-4}$-alkyl, C(=O)—OH, CF$_3$, NH$_2$, NH(C$_{1-4}$-alkyl), N(C$_{1-4}$-alkyl)$_2$, SH, S—C$_{1-4}$-alkyl, SCF$_3$, S(=O)$_2$OH.

In a preferred embodiment for m=1 or 2, B represents cyclopropyl; cyclobutyl; cyclopentyl; cyclohexyl; cycloheptyl; adamantyl; bicyclo[2.2.1]heptyl; bicyclo[2.2.2]octyl.

In a preferred embodiment for m=0, 1 or 2, B represents methyl; ethyl; n-propyl; isopropyl; n-butyl; sec-butyl or tert-butyl.

A further particularly preferred embodiment of the compounds of the general formula (1) according to the invention has the general formula (2):

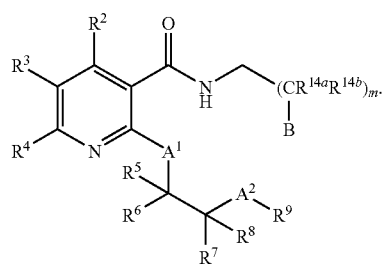

(2)

In a further preferred embodiment, the radicals R$^2$, R$^3$ and R$^4$ each independently of the others represents H; F; Cl; Br; I; NO$_2$; CF$_3$; CN; OH; OCF$_3$; SH; SCF$_3$; methyl; CH$_2$—O-methyl; CH$_2$—OH; C$_{2-6}$-alkyl, O—C$_{1-6}$-alkyl or S—C$_{1-6}$-alkyl, in each case saturated or unsaturated, branched or unbranched, unsubstituted or mono- or poly-substituted by one or more substituents each selected independently of one another from the group consisting of F, Cl, Br, I, OH, =O and O—C$_{1-4}$-alkyl; C$_{3-7}$-cycloalkyl, saturated or unsaturated, branched or unbranched, unsubstituted; NR$^a$R$^b$, wherein R$^a$ and R$^b$ each independently of the other represents H or C$_{1-4}$-alkyl, saturated or unsaturated, branched or unbranched, unsubstituted or mono- or poly-substituted by one or more substituents each selected independently of one another from the group consisting of OH, =O and O—C$_{1-4}$-alkyl, or R$^a$ and R$^b$, together with the nitrogen atom joining them, form a heterocyclyl, saturated or unsaturated, unsubstituted or mono- or poly-substituted by C$_{1-4}$-alkyl.

Preferably, the radicals R$^2$, R$^3$ and R$^4$ each independently of the others represents H; F; Cl; Br; I; NO$_2$; CF$_3$; CN; OH; OCF$_3$; SH; SCF$_3$; methyl; ethyl; n-propyl; isopropyl; butyl; sec-butyl; tert-butyl; CH$_2$CF$_3$; O-methyl; O-ethyl; O-n-propyl; O-isopropyl; O-butyl; O-sec-butyl; O-tert-butyl; O—(CH$_2$)$_2$—O-methyl; 0-(CH$_2$)$_2$—OH; O—(C=O)-methyl; O—(C=O)-ethyl; S-methyl; S-ethyl; cyclopropyl; cyclobutyl; NR$^a$R$^b$, wherein R$^a$ and R$^b$ each independently of the other is selected from the group consisting of H, methyl, ethyl, (CH$_2$)$_2$—O-methyl, (CH$_2$)$_2$—OH, (C=O)-methyl, (C=O)-ethyl, or R$^a$ and R$^b$, together with the nitrogen atom joining them, form a pyrrolidinyl, piperidinyl, 4-methyl-piperazinyl or morpholinyl.

Particularly preferably, the radicals R$^2$, R$^3$ and R$^4$ each independently of the others represents H; F; Cl; Br; I; methyl; ethyl; n-propyl, isopropyl; cyclopropyl; CN; CF$_3$; O-methyl; OCF$_3$; S-methyl; SCF$_3$, pyrrolidinyl, N(methyl)$_2$.

Most particularly preferably, the radicals R$^2$, R$^3$ and R$^4$ each independently of the others represents H; F; Cl; methyl; ethyl; O-methyl; CF$_3$; in particular H.

In a further preferred embodiment, the radicals R$^5$, R$^6$, R$^7$, R$^8$, R$^{10}$, R$^{11}$, R$^{12}$ and R$^{13}$ each independently of the others represents H; F; Cl; Br; I; NO$_2$; CF$_3$; CN; OH; OCF$_3$; SH; SCF$_3$; C$_{1-6}$-alkyl; O—C$_{1-6}$-alkyl or S—C$_{1-6}$-alkyl, in each case saturated or unsaturated, branched or unbranched, unsubstituted or mono- or poly-substituted by one or more substituents each selected independently of one another from the group consisting of F, Cl, Br, I, OH and O—C$_{1-4}$-alkyl; C$_{3-7}$-cycloalkyl, saturated or unsaturated, branched or unbranched, unsubstituted or mono- or poly-substituted by one or more substituents each selected independently of one another from the group consisting of F, Cl, Br, I, OH, =O and O—C$_{1-4}$-alkyl;

or R$^5$ and R$^6$ or R$^7$ and R$^8$ or R$^{10}$ and R$^{11}$ or R$^{12}$ and R$^{13}$ or R$^5$ and R$^{11}$ or R$^5$ and R$^7$ or R$^5$ and R$^{13}$ or R$^7$ and R$^{13}$ or R$^7$ and R$^{11}$ or R$^{11}$ and R$^{13}$, together with the carbon atom(s) joining them, form a cyclopropyl, cyclobutyl, cyclopentyl, cyclohexyl, pyrrolidinyl or piperidinyl, in each case unsubstituted or mono- or poly-substituted by one or more substituents each selected independently of one another from the group consisting of F, Cl, Br, I, OH, =O and O—C$_{1-4}$-alkyl; wherein the remaining substituents R$^5$, R$^6$, R$^7$, R$^8$, R$^{10}$, R$^{11}$, R$^{12}$ and R$^{13}$ in each case have the meaning given above.

Preferably, the radicals R$^5$, R$^6$, R$^7$, R$^8$, R$^{10}$, R$^{11}$, R$^{12}$ and R$^{13}$ each independently of the others represents H; F; Cl; Br; I; NO$_2$; CF$_3$; CN; OH; OCF$_3$; SH; SCF$_3$; methyl; ethyl; n-propyl; isopropyl; n-butyl; sec-butyl; tert-butyl; O-methyl; O-ethyl; O—(CH$_2$)$_2$—O—CH$_3$; O—(CH$_2$)$_2$—OH; S-methyl; S-ethyl; cyclopropyl; cyclobutyl; cyclopentyl; cyclohexyl;

or R$^5$ and R$^6$ or R$^7$ and R$^8$ or R$^{10}$ and R$^{11}$ or R$^{12}$ and R$^{13}$ or R$^5$ and R$^{11}$ or R$^5$ and R$^7$ or R$^5$ and R$^{13}$ or R$^7$ and R$^{13}$ or R$^7$ and R$^{11}$ or R$^{11}$ and R$^{13}$, together with the carbon atom(s) joining them, form a cyclopropyl, cyclobutyl, cyclopentyl or cyclohexyl, in each case unsubstituted; wherein the remaining substituents $R^5$, $R^6$, $R^7$, $R^8$, $R^{10}$, $R^{11}$, $R^{12}$ and $R^{13}$ in each case have the meaning given above.

Particularly preferably, the radicals $R^5$, $R^6$, $R^7$, $R^8$, $R^{10}$, $R^{11}$, $R^{12}$ and $R^{13}$ each independently of the others represents H; F; Cl; Br; I; CN; $CF_3$; $OCF_3$; $SCF_3$; methyl; ethyl; n-propyl, isopropyl; cyclopropyl; O-methyl; S-methyl; or $R^5$ and $R^7$ form a cyclopropyl, cyclobutyl, cyclopentyl or cyclohexyl ring substituted as desired by H, F, Cl, Me, Et, OMe, preferably an unsubstituted cyclopentyl or cyclohexyl ring.

Most particularly preferably, the radicals $R^5$, $R^6$, $R^7$, $R^8$, $R^{10}$, $R^{11}$, $R^{12}$ and $R^{13}$ each independently of the others represents F; Cl; H; methyl; ethyl; n-propyl, isopropyl; cyclopropyl; in particular F; H; methyl; or ethyl.

In particular, the radicals $R^{12}$ and $R^{13}$ each independently of the other represents H, F or methyl.

In a further preferred embodiment, the radical $R^9$ represents $C_{3-10}$-cycloalkyl or heterocyclyl, in each case saturated or unsaturated, unsubstituted or mono- or poly-substituted by one or more substituents each selected independently of one another from the group consisting of F, Cl, Br, I, $NO_2$, ON, OH, =O, O—$C_{1-4}$-alkyl, $OCF_3$, $C_{1-4}$-alkyl, $CF_3$, SH, S—$C_{1-4}$-alkyl and $SCF_3$; aryl or heteroaryl, in each case unsubstituted or mono- or poly-substituted by one or more substituents each selected independently of one another from the group consisting of F, Cl, Br, I, $NO_2$, ON, OH, O—$C_{1-4}$-alkyl, $OCF_3$, $C_{1-4}$-alkyl, $CF_3$, $NH_2$, $NH(C_{1-4}$-alkyl), $N(C_{1-4}$-alkyl)$_2$, SH, S—$C_{1-4}$-alkyl and $SCF_3$; or represents $CR^c R^d$, wherein $R^c$ and $R^d$ each independently of the other denotes $C_{1-4}$-alkyl, saturated or unsaturated, branched or unbranched, unsubstituted or mono- or poly-substituted by one or more substituents each selected independently of one another from the group consisting of F, Cl, Br, I, OH, O—$C_{1-4}$-alkyl, $CF_3$, $OCF_3$ and $SCF_3$.

Preferably, $R^9$ represents $C_{3-7}$-cycloalkyl, saturated or unsaturated, pyrrolidinyl, piperazinyl, 4-methylpiperazinyl, piperidinyl, morpholinyl, in each case unsubstituted or mono- or poly-substituted by one or more substituents each selected independently of one another from the group consisting of F, Cl, Br, I, OH, O—$C_{1-4}$-alkyl, $OCF_3$, $C_{1-4}$-alkyl, $CF_3$, SH, S—$C_{1-4}$-alkyl and $SCF_3$; phenyl, naphthyl, pyridyl or thienyl, in each case unsubstituted or mono- or poly-substituted by one or more substituents each selected independently of one another from the group consisting of F, Cl, Br, I, $NO_2$, ON, OH, O—$C_{1-4}$-alkyl, $OCF_3$, $C_{1-4}$-alkyl, $CF_3$, SH, S—$C_{1-4}$-alkyl and $SCF_3$; or represents $CR^c R^d$, wherein $R^c$ and $R^d$ each independently of the other denotes $C_{1-4}$-alkyl, saturated or unsaturated, branched or unbranched, unsubstituted or mono- or poly-substituted by one or more substituents each selected independently of one another from the group consisting of F, Cl, Br, I, OH and O—$C_{1-4}$-alkyl.

Particularly preferably, the radical $R^9$ is selected from the group consisting of phenyl, pyridyl or thienyl, in each case unsubstituted or mono- or poly-substituted by one or more substituents each selected independently of one another from the group consisting of F, Cl, Br, I, CN, OH, O—$C_{1-4}$-alkyl, $OCF_3$, $C_{1-4}$-alkyl, $CF_3$, SH, S—$C_{1-4}$-alkyl and $SCF_3$.

Most particularly preferably, $R^9$ represents phenyl, pyridyl and thienyl, unsubstituted or mono- or poly-substituted by one or more substituents each selected independently of one another from the group consisting of F, Cl, Br, I, CN, methyl, ethyl, n-propyl, isopropyl, n-butyl, sec-butyl, tert-butyl, O-methyl, O-ethyl, O-n-propyl, O-isopropyl, O-butyl, O-sec-butyl, O-tert-butyl, OH, $OCF_3$, $CF_3$, SH, S—$C_{1-4}$-alkyl and $SCF_3$.

In particular, $R^9$ represents phenyl, unsubstituted or mono- or poly-substituted by one or more substituents each selected independently of one another from the group consisting of F, Cl, Br, I, methyl, ethyl, n-propyl, isopropyl, n-butyl, sec-butyl, tert-butyl, O-methyl, O-ethyl, $OCF_3$, $CF_3$ and $SCF_3$.

In a further, particularly preferred embodiment
$A^1$ represents S;
$A^2$ represents $CR^{12}R^{13}$;
$R^1$ represents the partial structure (T1-1)

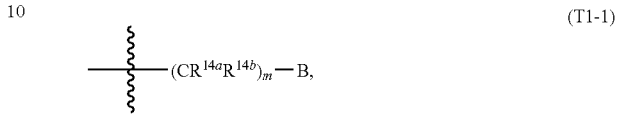

wherein
$R^{14a}$ and $R^{14b}$ each independently of the other represents H; F; Cl; Br; I; methyl; ethyl; n-propyl; isopropyl; n-butyl; sec-butyl; tert-butyl; OH; O-methyl; O-ethyl; O—$(CH_2)_2$—O—$CH_3$; or O—$(CH_2)_2$—OH;
m represents 0, 1 or 2;
B represents methyl; ethyl; n-propyl; isopropyl; n-butyl; sec-butyl; tert-butyl; cyclopropyl; cyclobutyl; cyclopentyl; cyclohexyl; cycloheptyl; adamantyl; bicyclo[2.2.1]heptyl; bicyclo[2.2.2]octyl; phenyl, pyridyl, thienyl, in each case unsubstituted or mono-, di- or tri-substituted by one, two or three substituents each selected independently of one another from the group consisting of F, Cl, Br, I, $NO_2$, CN, OH, O—$C_{1-4}$-alkyl, $OCF_3$, $C_{1-4}$-alkyl, C(=O)—OH, $CF_3$, $NH_2$, $NH(C_{1-4}$-alkyl), $N(C_{1-4}$-alkyl)$_2$, SH, S—$C_{1-4}$-alkyl, $SCF_3$ and S(=O)$_2$OH;
$R^2$, $R^3$ and $R^4$ each independently of the others represents H; F; Cl; Br; I; methyl; ethyl; n-propyl, isopropyl; cyclopropyl; CN; $CF_3$; O-methyl; $OCF_3$; S-methyl; $SCF_3$;
$R^5$, $R^6$, $R^7$, $R^8$, $R^{10}$, $R^{11}$, $R^{12}$ and $R^{13}$ each independently of the others represents H; F; Cl; Br; I; CN; $CF_3$; $OCF_3$; $SCF_3$; methyl; ethyl; n-propyl, isopropyl; cyclopropyl; O-methyl; S-methyl; and
$R^9$ represents cyclopentyl or cyclohexyl, in each case unsubstituted or mono- or poly-substituted by one or more substituents each selected independently of one another from the group consisting of F, Cl, Br, I, OH, O-methyl, $OCF_3$, methyl, ethyl and $CF_3$; phenyl, unsubstituted or mono- or poly-substituted by one or more substituents each selected independently of one another from the group consisting of F, Cl, Br, I, CN, methyl, ethyl, n-propyl, isopropyl, n-butyl, sec-butyl, tert-butyl, O-methyl, O-ethyl, O-n-propyl, O-isopropyl, O-butyl, O-sec-butyl, O-tert-butyl, OH, $OCF_3$, $CF_3$, SH, S—$C_{1-4}$-alkyl and $SCF_3$; or represents methyl, ethyl, n-propyl, isopropyl.

Particular preference is given to compounds from the group 1    2-(3-Phenyl-propylsulfanyl)-N-(thiophen-2-yl-methyl)-pyridine-3-carboxylic acid amide;

2    2-(3-Cyclohexyl-propylsulfanyl)-N-(thiophen-2-yl-methyl)-pyridine-3-carboxylic acid amide;

3    2-[(3-Oxo-3-phenyl-propyl)sulfanyl]-N-(thiophen-2-yl-methyl)-pyridine-3-carboxylic acid amide;

4    N-(Thiophen-2-yl-methyl)-2-[2-[3-(trifluoromethyl)-phenoxy]-ethylsulfanyl]-pyridine-3-carboxylic acid amide;

5    2-(4-Methyl-pentylsulfanyl)-N-(thiophen-2-yl-methyl)-pyridine-3-carboxylic acid amide;

7    2-(4-Phenyl-butyl)-N-(thiophen-2-yl-methyl)-pyridine-3-carboxylic acid amide;

8    2-[3-(Benzenesulfonyl)-propyl]-N-(cyclohexyl-methyl)-pyridine-3-carboxylic acid amide;

9 N-(Cyclohexyl-methyl)-2-(4-phenyl-butyl)-pyridine-3-carboxylic acid amide;
10 2-[3-(Benzenesulfonyl)-propyl]-N-(thiophen-2-yl-methyl)-pyridine-3-carboxylic acid amide;
12 N-(Thiophen-2-yl-methyl)-2-[3-[[3-(trifluoromethyl)phenyl]sulfonyl]-propyl]-pyridine-3-carboxylic acid amide;
13 N-(Thiophen-2-yl-methyl)-2-[3-[[3-(trifluoromethyl)phenyl]sulfanyl]-propyl]-pyridine-3-carboxylic acid amide;
16 2-(2-Phenylsulfanyl-propylsulfanyl)-N-(thiophen-2-yl-methyl)-pyridine-3-carboxylic acid amide;
17 2-[3-(4-Fluorophenyl)-propylsulfanyl]-N-(thiophen-2-yl-methyl)-pyridine-3-carboxylic acid amide;
18 N-(Thiophen-2-yl-methyl)-2-[3-[3-(trifluoromethyl)phenyl]-propylsulfanyl]-pyridine-3-carboxylic acid amide;
19 2-[2-[(4-Fluorophenyl)sulfanyl]-propylsulfanyl]-N-(thiophen-2-yl-methyl) -pyridine-3-carboxylic acid amide;
20 N-(Thiophen-2-yl-methyl)-2-[2-[[3-(trifluoromethyl)phenyl]sulfanyl]-propylsulfanyl]-pyridine-3-carboxylic acid amide;
21 N-(Thiophen-2-yl-methyl)-2-[4-[3-(trifluoromethyl)phenyl]-butyl]-pyridine-3-carboxylic acid amide;
22 2-[4-(4-Fluorophenyl)-butyl]-N-(thiophen-2-yl-methyl)-pyridine-3-carboxylic acid amide;
23 2-(3-Phenylsulfanyl-propyl)-N-(thiophen-2-yl-methyl)-pyridine-3-carboxylic acid amide;
24 2-[(1-Methyl-2-phenylsulfanyl-ethyl)sulfanyl]-N-(thiophen-2-yl-methyl) -pyridine-3-carboxylic acid amide;
25 N-(Cycloheptyl-methyl)-2-[4-[3-(trifluoromethyl)phenyl]-butyl]-pyridine-3-carboxylic acid amide
26 N-(5-Bicyclo[2.2.1]heptanyl-methyl)-2-[4-[3-(trifluoromethyl)phenyl]-butyl]-pyridine-3-carboxylic acid amide
27 N-(5-Bicyclo[2.2.1]heptanyl-methyl)-2-[3-[3-(trifluoromethyl)phenyl]-propylsulfanyl]-pyridine-3-carboxylic acid amide
28 N-(5-Bicyclo[2.2.1]heptanyl-methyl)-2-(4-methyl-pentylsulfanyl)-pyridine-3-carboxylic acid amide
29 N-(Cycloheptyl-methyl)-2-[3-[(4-fluorophenyl)sulfanyl]-propyl]-pyridine-3-carboxylic acid amide
30 N-(5-Bicyclo[2.2.1]heptanyl-methyl)-2-[3-[(4-fluorophenyl)sulfanyl]-propyl]-pyridine-3-carboxylic acid amide
31 N-(Cycloheptyl-methyl)-2-[3-[[3-(trifluoromethyl)phenyl]sulfonyl]-propyl]-pyridine-3-carboxylic acid amide
32 N-(5-Bicyclo[2.2.1]heptanyl-methyl)-2-[3-[[3-(trifluoromethyl)phenyl]sulfonyl]-propyl]-pyridine-3-carboxylic acid amide
33 N-(5-Bicyclo[2.2.1]heptanyl-methyl)-2-(3-phenyl-propylsulfanyl)-pyridine-3-carboxylic acid amide
34 N-(5-Bicyclo[2.2.1]heptanyl-methyl)-2-[3-[4-(trifluoromethyl)-phenyl]-propylsulfanyl]-pyridine-3-carboxylic acid amide
35 N-(5-Bicyclo[2.2.1]heptanyl-methyl)-2-[3-(4-chlorophenyl)-propylsulfanyl]-pyridine-3-carboxylic acid amide
36 N-[(3,5-Difluoro-phenyl)-methyl]-2-[3-(4-fluorophenyl)-propylsulfanyl]-pyridine-3-carboxylic acid amide
37 N-[(5-Chloro-thiophen-2-yl)-methyl]-2-[3-(4-fluorophenyl)-propylsulfanyl]-pyridine-3-carboxylic acid amide
38 N-[(2,2-Dimethyl-cyclopropyl)-methyl]-2-[3-(4-fluorophenyl)-propylsulfanyl]-pyridine-3-carboxylic acid amide
39 N-(5-Bicyclo[2.2.1]heptanyl-methyl)-2-[3-(3-fluorophenyl)-propylsulfanyl]-pyridine-3-carboxylic acid amide
40 N-(Cyclohexyl-methyl)-2-[3-(4-fluorophenyl)-propylsulfanyl]-pyridine-3-carboxylic acid amide
41 N-(Cycloheptyl-methyl)-2-[3-(4-fluorophenyl)-propylsulfanyl]-pyridine-3-carboxylic acid amide
43 N-(5-Bicyclo[2.2.1]heptanyl-methyl)-2-[[3-(4-fluorophenyl)-3-oxo-propyl]sulfanyl]-pyridine-3-carboxylic acid amide
44 N-(5-Bicyclo[2.2.1]heptanyl-methyl)-2-[(3-oxo-3-phenyl-propyl)sulfanyl]-pyridine-3-carboxylic acid amide
45 N-(5-Bicyclo[2.2.1]heptanyl-methyl)-2-(hexylsulfanyl)-pyridine-3-carboxylic acid amide
46 N-(5-Bicyclo[2.2.1]heptanyl-methyl)-2-(2-phenoxy-ethylsulfanyl)-pyridine-3-carboxylic acid amide
47 N-(5-Bicyclo[2.2.1]heptanyl-methyl)-2-[2-[3-(trifluoromethyl)-phenoxy]-ethylsulfanyl]-pyridine-3-carboxylic acid amide
48 2-[3-(4-Fluorophenyl)-propylsulfanyl]-N-(3,3,3-trifluoro-propyl)-pyridine-3-carboxylic acid amide
49 N-(5-Bicyclo[2.2.1]heptanyl-methyl)-2-[2-(4-fluorophenoxy)-ethylsulfanyl]-pyridine-3-carboxylic acid amide
52 N-(5-Bicyclo[2.2.1]heptanyl-methyl)-2-(3-naphthalen-1-yl-propylsulfanyl) -pyridine-3-carboxylic acid amide
53 N-(5-Bicyclo[2.2.1]heptanyl-methyl)-2-[3-[3-fluoro-4-(trifluoromethyl)-phenyl]-propylsulfanyl]-pyridine-3-carboxylic acid amide
54 N-(5-Bicyclo[2.2.1]heptanyl-methyl)-2-[3-[4-fluoro-3-(trifluoromethyl)-phenyl]-propylsulfanyl]-pyridine-3-carboxylic acid amide
55 N-(Cyclooctyl-methyl)-2-[3-(4-fluorophenyl)-propylsulfanyl]-pyridine-3-carboxylic acid amide
56 N-(5-Bicyclo[2.2.1]heptanyl-methyl)-2-[3-(4-methoxyphenyl)-propylsulfanyl]-pyridine-3-carboxylic acid amide
57 2-[3-(4-Fluorophenyl)-propylsulfanyl]-N-[(4-methoxyphenyl)-methyl]-pyridine-3-carboxylic acid amide
59 2-[3-(4-Fluorophenyl)-propylsulfanyl]-N-[[3-(trifluoromethyl)phenyl]-methyl]-pyridine-3-carboxylic acid amide
60 N-(5-Bicyclo[2.2.1]heptanyl-methyl)-2-[3-(3,4-difluorophenyl)-propylsulfanyl]-pyridine-3-carboxylic acid amide
61 N-(5-Bicyclo[2.2.1]heptanyl-methyl)-2-[3-(3,5-difluorophenyl)-propylsulfanyl]-pyridine-3-carboxylic acid amide
62 N-(5-Bicyclo[2.2.1]heptanyl-methyl)-2-[3-(2,4-difluorophenyl)-propylsulfanyl]-pyridine-3-carboxylic acid amide
63 N-[(2-Fluorophenyl)-methyl]-2-[3-(4-fluorophenyl)-propylsulfanyl]-pyridine-3-carboxylic acid amide
64 N-[(3-Fluorophenyl)-methyl]-2-[3-(4-fluorophenyl)-propylsulfanyl]-pyridine-3-carboxylic acid amide
65 N-[(4-Fluorophenyl)-methyl]-2-[3-(4-fluorophenyl)-propylsulfanyl]-pyridine-3-carboxylic acid amide
66 N-Benzyl-2-[3-(4-fluorophenyl)-propylsulfanyl]-pyridine-3-carboxylic acid amide
67 N-(5-Bicyclo[2.2.1]heptanyl-methyl)-2-[(1-methyl-3-phenyl-propyl)sulfanyl]-pyridine-3-carboxylic acid amide
68 N-(5-Bicyclo[2.2.1]heptanyl-methyl)-2-[3-(3,4,5-trifluoro-phenyl)-propylsulfanyl]-pyridine-3-carboxylic acid amide
69 N-(5-Bicyclo[2.2.1]heptanyl-methyl)-2-[3-[3-fluoro-5-(trifluoromethyl)-phenyl]-propylsulfanyl]-pyridine-3-carboxylic acid amide
70 N-(5-Bicyclo[2.2.1]heptanyl-methyl)-2-[3-(3-methoxyphenyl)-propylsulfanyl]-pyridine-3-carboxylic acid amide
71 N-[(3,4-Difluoro-phenyl)-methyl]-2-[3-(4-fluorophenyl)-propylsulfanyl]-pyridine-3-carboxylic acid amide 72  N-(2,3-Dihydro-benzofuran-5-yl-methyl)-2-[3-(4-fluorophenyl)-propylsulfanyl]-pyridine-3-carboxylic acid amide
73  N-(5-Bicyclo[2.2.1]heptanyl-methyl)-2-[3-(3-hydroxyphenyl)-propylsulfanyl]-pyridine-3-carboxylic acid amide
74  N-(5-Bicyclo[2.2.1]heptanyl-methyl)-2-[[3-(4-fluorophenyl)-1-methyl-propyl]sulfanyl]-pyridine-3-carboxylic acid amide
75  N-(5-Bicyclo[2.2.1]heptanyl-methyl)-2-[[3-(4-fluorophenyl)-2-methyl-propyl]sulfanyl]-pyridine-3-carboxylic acid amide
76  2-[3-(4-Fluorophenyl)-propylsulfanyl]-N-[(2-methoxyphenyl)-methyl]-pyridine-3-carboxylic acid amide
77  2-[3-(4-Fluorophenyl)-propylsulfanyl]-N-[(3-methoxyphenyl)-methyl]-pyridine-3-carboxylic acid amide
78  2-[3-(4-Fluorophenyl)-propylsulfanyl]-N-phenethyl-pyridine-3-carboxylic acid amide
79  2-[3-(4-Fluorophenyl)-propylsulfanyl]-N-[[4-(trifluoromethyloxy)-phenyl]-methyl]-pyridine-3-carboxylic acid amide
80  2-[3-(4-Fluorophenyl)-propylsulfanyl]-N-[[4-(trifluoromethyl)-phenyl]-methyl]-pyridine-3-carboxylic acid amide
81  2-[3-(4-Fluorophenyl)-propylsulfanyl]-N-(2-pyridine-3-yl-ethyl)-pyridine-3-carboxylic acid amide
82  2-[3-(4-Fluorophenyl)-propylsulfanyl]-N-(2-pyridine-2-yl-ethyl)-pyridine-3-carboxylic acid amide
83  2-[3-(4-Fluorophenyl)-propylsulfanyl]-N-[(2-hydroxyphenyl)-methyl]-pyridine-3-carboxylic acid amide
84  2-[3-(4-Fluorophenyl)-propylsulfanyl]-N-[(3-hydroxyphenyl)-methyl]-pyridine-3-carboxylic acid amide
85  2-[3-(4-Fluorophenyl)-propylsulfanyl]-N-[2-(m-tolyl)-ethyl]-pyridine-3-carboxylic acid amide
86  2-[3-(4-Fluorophenyl)-propylsulfanyl]-N-[2-(o-tolyl)-ethyl]-pyridine-3-carboxylic acid amide
87  2-[3-(4-Fluorophenyl)-propylsulfanyl]-N-[[3-(trifluoromethyloxy)-phenyl]-methyl]-pyridine-3-carboxylic acid amide
88  2-[3-(4-Fluorophenyl)-propylsulfanyl]-N-[(4-hydroxyphenyl)-methyl]-pyridine-3-carboxylic acid amide
89  2-[3-(4-Fluorophenyl)-propylsulfanyl]-N-(2-pyridine-4-yl-ethyl)-pyridine-3-carboxylic acid amide
90  2-[3-(4-Fluorophenyl)-propylsulfanyl]-N-[2-(p-tolyl)-ethyl]-pyridine-3-carboxylic acid amide
91  N-(5-Bicyclo[2.2.1]heptanyl-methyl)-2-[3-(4-fluorophenyl)-butylsulfanyl]-pyridine-3-carboxylic acid amide
92  N-(5-Bicyclo[2.2.1]heptanyl-methyl)-2-[3-(2,4,5-trifluoro-phenyl)-propylsulfanyl]-pyridine-3-carboxylic acid amide
93  2-[3-(4-Fluorophenyl)-propylsulfanyl]-N-(3-pyridine-2-yl-propyl)-pyridine-3-carboxylic acid amide
94  2-[3-(4-Fluorophenyl)-propylsulfanyl]-N-(3-pyridine-3-yl-propyl)-pyridine-3-carboxylic acid amide
95  2-[3-(4-Fluorophenyl)-propylsulfanyl]-N-(3-pyridine-4-yl-propyl)-pyridine-3-carboxylic acid amide
96  2-[3-(4-Fluorophenyl)-propylsulfanyl]-N-propyl-pyridine-3-carboxylic acid amide
97  N-Butyl-2-[3-(4-fluorophenyl)-propylsulfanyl]-pyridine-3-carboxylic acid amide
98  2-(3-Pyridin-3-yl-propylsulfanyl)-N-(thiophen-2-yl-methyl)-pyridine-3-carboxylic acid amide
99  2-[3-(p-Tolyl)-propylsulfanyl]-N-(thiophen-2-yl-methyl)-pyridine-3-carboxylic acid amide
100  2-(4-Phenyl-butylsulfanyl)-N-(thiophen-2-yl-methyl)-pyridine-3-carboxylic acid amide
101  2-(3-Pyridin-4-yl-propylsulfanyl)-N-(thiophen-2-yl-methyl)-pyridine-3-carboxylic acid amide
102  2-(3-Naphthalen-2-yl-propylsulfanyl)-N-(thiophen-2-yl-methyl)-pyridine-3-carboxylic acid amide
103  2-[3-(m-Tolyl)-propylsulfanyl]-N-(thiophen-2-yl-methyl)-pyridine-3-carboxylic acid amide
104  N-(Thiophen-2-yl-methyl)-2-(3-thiophen-2-yl-propylsulfanyl)-pyridine-3-carboxylic acid amide
105  2-[(1-Methyl-3-phenyl-propyl)sulfanyl]-N-(thiophen-2-yl-methyl)-pyridine-3-carboxylic acid amide
106  N-(Thiophen-2-yl-methyl)-2-(3-thiophen-3-yl-propylsulfanyl)-pyridine-3-carboxylic acid amide
107  2-[[1-Methyl-3-[3-(trifluoromethyl)phenyl]-propyl]sulfanyl]-N-(thiophen-2-yl-methyl) -pyridine-3-carboxylic acid amide
108  2-[(2-Benzyl-cyclohexyl)sulfanyl]-N-(thiophen-2-yl-methyl)-pyridine-3-carboxylic acid amide
109  2-[3-[3-Methyl-5-(trifluoromethyl)-phenyl]-propylsulfanyl]-N-(thiophen-2-yl-methyl) -pyridine-3-carboxylic acid amide
110  2-[4-(3,4-Difluoro-phenyl)-butylsulfanyl]-N-(thiophen-2-yl-methyl)-pyridine-3-carboxylic acid amide
111  2-(3-Pyridin-2-yl-propylsulfanyl)-N-(thiophen-2-yl-methyl)-pyridine-3-carboxylic acid amide
113  2-[3-[4-Methyl-3-(trifluoromethyl)-phenyl]-propylsulfanyl]-N-(thiophen-2-yl-methyl) -pyridine-3-carboxylic acid amide
114  2-[(3-Phenyl-cyclohexyl)sulfanyl]-N-(thiophen-2-yl-methyl)-pyridine-3-carboxylic acid amide
116  2-[[3,3-Difluoro-3-(4-fluorophenyl)-propyl]sulfanyl]-N-(3,3-dimethyl-butyl) -pyridine-3-carboxylic acid amide
117  N-(Cycloheptyl-methyl)-2-[[3,3-difluoro-3-(4-fluorophenyl)-propyl]sulfanyl]-pyridine-3-carboxylic acid amide
118  2-[[3,3-Difluoro-3-(4-fluorophenyl)-propyl]sulfanyl]-N-(thiophen-2-yl-methyl) -pyridine-3-carboxylic acid amide
119  2-[3-(4-Fluorophenyl)-propylsulfanyl]-N-(1,2,3,4-tetrahydro-naphthalen-2-yl-methyl) -pyridine-3-carboxylic acid amide
120  N-(2,3-Dihydro-1H-inden-2-yl-methyl)-2-[3-(4-fluorophenyl)-propylsulfanyl]-pyridine-3-carboxylic acid amide
121  N-(1,3-Benzodioxol-5-yl-methyl)-2-[3-(4-fluorophenyl)-propylsulfanyl]-pyridine-3-carboxylic acid amide
122  2-[3-(4-Fluorophenyl)-propylsulfanyl]-N-[(3-phenyl-phenyl)-methyl]-pyridine-3-carboxylic acid amide
123  2-[3-(4-Fluorophenyl)-propylsulfanyl]-N-[(3-methyl-cyclohexyl)-methyl]-pyridine-3-carboxylic acid amide
124  2-[[3,3-Difluoro-3-(4-fluorophenyl)-propyl]sulfanyl]-N-[(4-fluorophenyl)-methyl]-pyridine-3-carboxylic acid amide
125  N-(3,3-Dimethyl-2-oxo-butyl)-2-[3-(4-fluorophenyl)-propylsulfanyl]-pyridine-3-carboxylic acid amide
127  2-[3-(4-Fluorophenyl)-propylsulfanyl]-N-(pyridin-3-yl-methyl)-pyridine-3-carboxylic acid amide
128  2-[3-(4-Fluorophenyl)-propylsulfanyl]-N-(pyridin-4-yl-methyl)-pyridine-3-carboxylic acid amide
129  3-[[[2-[3-(4-Fluorophenyl)-propylsulfanyl]-pyridine-3-carbonyl]amino]-methyl]-benzoic acid methyl ester
130  2-[3-(4-Fluorophenyl)-propylsulfanyl]-N-[3-(2-methoxyphenyl)-propyl]-pyridine-3-carboxylic acid amide
132  N-[(4-Fluorophenyl)-methyl]-2-[[1-methyl-3-[3-(trifluoromethyl)phenyl]-propyl]sulfanyl]-pyridine-3-carboxylic acid amide
133  2-[3-(4-Fluorophenyl)-propylsulfanyl]-N-(3-methyl-butyl)-pyridine-3-carboxylic acid amide 134 2-[3-(4-Fluorophenyl)-propylsulfanyl]-N-(tetrahydro-pyran-2-yl-methyl)-pyridine-3-carboxylic acid amide
135 2-[3-(4-Fluorophenyl)-propylsulfanyl]-N-[3-(1H-pyrazol-1-yl)-propyl]-pyridine-3-carboxylic acid amide
136 2-[3-(4-Fluorophenyl)-propylsulfanyl]-N-(naphthalen-2-yl-methyl)-pyridine-3-carboxylic acid amide
137 N-(2,3-Dihydro-[1,4]benzodioxin-6-yl-methyl)-2-[3-(4-fluorophenyl)-propylsulfanyl]-pyridine-3-carboxylic acid amide
138 2-[3-(4-Fluorophenyl)-propylsulfanyl]-N-[(3-morpholin-4-yl-phenyl)-methyl]-pyridine-3-carboxylic acid amide
139 N-(2,3-Dihydro-benzofuran-6-yl-methyl)-2-[3-(4-fluorophenyl)-propylsulfanyl]-pyridine-3-carboxylic acid amide
140 2-[3-(4-Fluorophenyl)-propylsulfanyl]-N-[[3-(1H-pyrazol-1-yl)-phenyl]-methyl]-pyridine-3-carboxylic acid amide
141 2-[3-(4-Fluorophenyl)-propylsulfanyl]-N-[3-(1H-[1,2,3]triazol-1-yl)-propyl]-pyridine-3-carboxylic acid amide
142 N-(7-Bicyclo[2.2.1]heptanyl-methyl)-2-[3-(4-fluorophenyl)-propylsulfanyl]-pyridine-3-carboxylic acid amide
144 2-[3-(4-Fluorophenyl)-propylsulfanyl]-N-(thiazol-2-yl-methyl)-pyridine-3-carboxylic acid amide
145 2-[3-(4-Fluorophenyl)-propylsulfanyl]-N-(thiazol-5-yl-methyl)-pyridine-3-carboxylic acid amide
146 2-[3-(4-Fluorophenyl)-propylsulfanyl]-N-(oxazol-2-yl-methyl)-pyridine-3-carboxylic acid amide
148 N-(3,3-Dimethyl-butyl)-2-[3-(4-fluorophenyl)-propylsulfanyl]-4-methyl-pyridine-3-carboxylic acid amide
149 N-(3,3-Dimethyl-butyl)-2-[[1-methyl-3-[3-(trifluoromethyl)phenyl]-propyl]sulfanyl]-pyridine-3-carboxylic acid amide
150 2-[3-(4-Fluorophenyl)-propylsulfanyl]-N-(quinolin-7-yl-methyl)-pyridine-3-carboxylic acid amide
151 2-[3-(4-Fluorophenyl)-propylsulfanyl]-N-[(3-pyridin-2-yl-phenyl)-methyl]-pyridine-3-carboxylic acid amide
152 2-[3-(4-Fluorophenyl)-propylsulfanyl]-N-[(3-pyridin-3-yl-phenyl)-methyl]-pyridine-3-carboxylic acid amide
153 N-(3,3-Dimethyl-butyl)-2-[[(1R)-1-methyl-3-phenyl-propyl]sulfanyl]-pyridine-3-carboxylic acid amide
154 N-(3,3-Dimethyl-butyl)-2-[[(1S)-1-methyl-3-phenyl-propyl]sulfanyl]-pyridine-3-carboxylic acid amide
155 2-[(2-Benzyl-cyclopentyl)sulfanyl]-(3,3-dimethyl-butyl)-pyridine-3-carboxylic acid amide
156 N-(7-Bicyclo[2.2.1]heptanyl-methyl)-2-[3-[3-(trifluoromethyl)phenyl]-propylsulfanyl]-pyridine-3-carboxylic acid amide
157 2-[3-(4-Fluorophenyl)-propylsulfanyl]-N-[3-(1H-[1,2,4]triazol-1-yl)-propyl]-pyridine-3-carboxylic acid amide
158 2-[3-(4-Fluorophenyl)-propylsulfanyl]-N-([1,3,4]oxadiazol-2-yl-methyl)-pyridine-3-carboxylic acid amide
159 2-[3-(4-Fluorophenyl)-propylsulfanyl]-N-[(3-pyridin-4-yl-phenyl)-methyl]-pyridine-3-carboxylic acid amide
160 N-[[4-(Cyclopropyl-methyl)-3,4-dihydro-2H-[1,4]benzoxazin-6-yl]-methyl]-2-[3-(4-fluorophenyl)-propylsulfanyl]-pyridine-3-carboxylic acid amide
161 N-[(4-Ethyl-3,4-dihydro-2H-[1,4]benzoxazin-6-yl)-methyl]-2-[3-(4-fluorophenyl)-propylsulfanyl]-pyridine-3-carboxylic acid amide
162 2-[3-(4-Fluorophenyl)-propylsulfanyl]-N-[(4-methyl-3,4-dihydro-2H-[1,4]benzoxazin-6-yl)-methyl]-pyridine-3-carboxylic acid amide
163 2-[3-(4-Fluorophenyl)-propylsulfanyl]-N-(3-methyl-3-phenyl-butyl)-pyridine-3-carboxylic acid amide
164 N-(7-Bicyclo[2.2.1]heptanyl-methyl)-2-[[3,3-difluoro-3-(4-fluorophenyl)-propyl]sulfanyl]-pyridine-3-carboxylic acid amide
165 2-[[3,3-Difluoro-3-[3-(trifluoromethyl)phenyl]-propyl]sulfanyl]-N-[(4-fluorophenyl)-methyl]-pyridine-3-carboxylic acid amide
166 2-[[3,3-Difluoro-3-[3-(trifluoromethyl)phenyl]-propyl]sulfanyl]-N-(3,3-dimethyl-butyl)-pyridine-3-carboxylic acid amide
168 2-[[3,3-Difluoro-3-(4-fluorophenyl)-propyl]sulfanyl]-N-[(3-fluorophenyl)-methyl]-pyridine-3-carboxylic acid amide
170 N-Butyl-2-[[3,3-difluoro-3-(4-fluorophenyl)-propyl]sulfanyl]-pyridine-3-carboxylic acid amide
171 2-[[3,3-Difluoro-3-(4-fluorophenyl)-propyl]sulfanyl]-N-(2-methoxy-ethyl)-pyridine-3-carboxylic acid amide
172 2-[3-(4-Fluorophenyl)-propylsulfanyl]-N-(2-methoxy-ethyl)-pyridine-3-carboxylic acid amide
173 N-[(4-Fluoro-2-hydroxy-phenyl)-methyl]-2-[3-(4-fluorophenyl)-propylsulfanyl]-pyridine-3-carboxylic acid amide
174 2-[3-(4-Fluorophenyl)-propylsulfanyl]-N-(furan-2-yl-methyl)-pyridine-3-carboxylic acid amide
175 2-[3-(4-Fluorophenyl)-propylsulfanyl]-N-[(5-methyl-furan-2-yl)-methyl]-pyridine-3-carboxylic acid amide
176 N-[(4-Fluorophenyl)-methyl]-2-[[3-(4-fluorophenyl)-1-methyl-propyl]sulfanyl]-pyridine-3-carboxylic acid amide
177 2-[[3-(4-Fluorophenyl)-1-methyl-propyl]sulfanyl]-N-(3-methyl-butyl)-pyridine-3-carboxylic acid amide
178 N-(7-Bicyclo[2.2.1]heptanyl-methyl)-2-[[3-(4-fluorophenyl)-1-methyl-propyl]sulfanyl]-pyridine-3-carboxylic acid amide
179 2-[[3,3-Difluoro-3-(4-fluorophenyl)-propyl]sulfanyl]-N-(tetrahydro-furan-2-yl-methyl)-pyridine-3-carboxylic acid amide
180 2-[[3,3-Difluoro-3-(4-fluorophenyl)-propyl]sulfanyl]-N-(tetrahydro-pyran-2-yl-methyl)-pyridine-3-carboxylic acid amide
181 2-[3-(4-Fluorophenyl)-propylsulfanyl]-N-(tetrahydro-furan-2-yl-methyl)-pyridine-3-carboxylic acid amide
182 2-[3-(4-Fluorophenyl)-propylsulfanyl]-N-(2-methoxy-3,3-dimethyl-butyl)-pyridine-3-carboxylic acid amide
183 2-[[3,3-Difluoro-3-(4-fluorophenyl)-propyl]sulfanyl]-N-(m-tolyl-methyl)-pyridine-3-carboxylic acid amide
184 2-[[3,3-Difluoro-3-(4-fluorophenyl)-propyl]sulfanyl]-N-[(3,5-dimethyl-phenyl)-methyl]-pyridine-3-carboxylic acid amide
185 2-[[3,3-Difluoro-3-(4-fluorophenyl)-propyl]sulfanyl]-N-propyl-pyridine-3-carboxylic acid amide
186 2-[[3,3-Difluoro-3-(4-fluorophenyl)-propyl]sulfanyl]-N-hexyl-pyridine-3-carboxylic acid amide
187 2-[[3,3-Difluoro-3-(4-fluorophenyl)-propyl]sulfanyl]-N-(tetrahydro-furan-3-yl-methyl)-pyridine-3-carboxylic acid amide
188 2-[[3,3-Difluoro-3-(4-fluorophenyl)-propyl]sulfanyl]-N-(tetrahydro-pyran-3-yl-methyl)-pyridine-3-carboxylic acid amide
189 2-[[3,3-Difluoro-3-(4-fluorophenyl)-propyl]sulfanyl]-N-(tetrahydro-pyran-4-yl-methyl)-pyridine-3-carboxylic acid amide
190 2-[[3,3-Difluoro-3-(4-fluorophenyl)-propyl]sulfanyl]-N-(furan-2-yl-methyl)-pyridine-3-carboxylic acid amide
191 2-[[3,3-Difluoro-3-(4-fluorophenyl)-propyl]sulfanyl]-N-[(5-methyl-furan-2-yl)-methyl]-pyridine-3-carboxylic acid amide 192  2-[[3,3-Difluoro-3-(4-fluorophenyl)-propyl]sulfanyl]-N-pentyl-pyridine-3-carboxylic acid amide
193  2-[[3,3-Difluoro-3-(4-fluorophenyl)-propyl]sulfanyl]-N-(3-methoxy-butyl) -pyridine-3-carboxylic acid amide
194  2-[[3,3-Difluoro-3-(4-fluorophenyl)-propyl]sulfanyl]-N-(2-methoxy-propyl) -pyridine-3-carboxylic acid amide
195  2-[[3,3-Difluoro-3-(4-fluorophenyl)-propyl]sulfanyl]-N-(2-methoxy-butyl) -pyridine-3-carboxylic acid amide
196  3-[[2-[[3,3-Difluoro-3-(4-fluorophenyl)-propyl]sulfanyl]-pyridine-3-carbonyl]amino]-propionic acid methyl ester
197  3-[[2-[[3,3-Difluoro-3-(4-fluorophenyl)-propyl]sulfanyl]-pyridine-3-carbonyl]amino]-propionic acid
198  2-[[3,3-Difluoro-3-(4-fluorophenyl)-propyl]sulfanyl]-N-(2-dimethylaminoethyl) -pyridine-3-carboxylic acid amide
199  2-[[3-(3,4-Difluoro-phenyl)-1-methyl-propyl]sulfanyl]-N-[(4-fluorophenyl)-methyl]-pyridine-3-carboxylic acid amide
200  2-[[3-(3,4-Difluoro-phenyl)-1-methyl-propyl]sulfanyl]-N-(3-methyl-butyl) -pyridine-3-carboxylic acid amide
201  N-[(4-Fluorophenyl)-methyl]-2-[[3-(3-fluorophenyl)-1-methyl-propyl]sulfanyl]-pyridine-3-carboxylic acid amide
202  2-[[3-(3-Fluorophenyl)-1-methyl-propyl]sulfanyl]-N-(3-methyl-butyl)-pyridine-3-carboxylic acid amide
203  N-(3-Methyl-butyl)-2-[[1-methyl-3-[3-(trifluoromethyl)phenyl]-propyl]sulfanyl]-pyridine-3-carboxylic acid amide
204  2-[[3-(3,4-Difluoro-phenyl)-3,3-difluoro-propyl]sulfanyl]-N-[(4-fluorophenyl)-methyl]-pyridine-3-carboxylic acid amide
205  N-(1-Bicyclo[2.2.1]heptanyl-methyl)-2-[[3,3-difluoro-3-(4-fluorophenyl)-propyl]sulfanyl]-pyridine-3-carboxylic acid amide
206  N-(1-Bicyclo[2.2.1]heptanyl-methyl)-2-[3-(4-fluorophenyl)-propylsulfanyl]-pyridine-3-carboxylic acid amide
207  N-[(4-Fluorophenyl)-methyl]-2-[3-[3-(trifluoromethyl)phenyl]-propylsulfanyl]-pyridine-3-carboxylic acid amide
208  N-(3-Methyl-butyl)-2-[3-[3-(trifluoromethyl)phenyl]-propylsulfanyl]-pyridine-3-carboxylic acid amide
209  2-[[3-(3,4-Difluoro-phenyl)-3,3-difluoro-propyl]sulfanyl]-N-(3-methyl-butyl) -pyridine-3-carboxylic acid amide
210  N-(7-Bicyclo[2.2.1]heptanyl-methyl)-2-[[3-(3,4-difluoro-phenyl)-3,3-difluoro-propyl]sulfanyl]-pyridine-3-carboxylic acid amide
211  2-[[3,3-Difluoro-3-(4-fluorophenyl)-propyl]sulfanyl]-N-(2-hydroxy-ethyl)-pyridine-3-carboxylic acid amide
224  N-[(4-Fluoro-2-methoxy-phenyl)-methyl]-2-[3-(4-fluorophenyl)-propylsulfanyl]-pyridine-3-carboxylic acid amide or physiologically acceptable salts thereof.

The substituted nicotinamides according to the invention and in each case the corresponding acids, bases, salts and solvates are suitable as pharmaceutical active ingredients in medicaments.

The invention therefore further provides a medicament comprising at least one substituted nicotinamide of the general formula (1) according to the invention wherein the radicals $R^1$ to $R^{13}$ have the meaning given above and, optionally, one or more pharmaceutically acceptable auxiliary substances.

In addition to at least one compound according to the invention, the medicaments according to the invention optionally comprise suitable additives and/or auxiliary substances, that is to say also carriers, fillers, solvents, diluents, colorings and/or binders, and can be administered as liquid medicament forms in the form of injection solutions, drops or juices, as semi-solid medicament forms in the form of granules, tablets, pellets, patches, capsules, plasters/spray-on plasters or aerosols. The choice of auxiliary substances etc. and the amounts thereof to be used are dependent on whether the medicament is to be administered orally, perorally, parenterally, intravenously, intraperitoneally, intradermally, intramuscularly, intranasally, buccally, rectally or locally, for example to the skin, the mucosa or into the eyes. Preparations in the form of tablets, dragées, capsules, granules, drops, juices and syrups are suitable for oral administration, and solutions, suspensions, readily reconstitutable dry preparations and sprays are suitable for parenteral, topical and inhalatory administration. Compounds according to the invention in a depot, in dissolved form or in a plaster, optionally with the addition of agents that promote penetration through the skin, are suitable percutaneous forms of administration. Forms of preparation for administration orally or percutaneously can release the compounds according to the invention in a delayed manner. The compounds according to the invention can also be administered in parenteral long-term depot forms such as, for example, implants or implanted pumps. In principle, other further active ingredients known to the person skilled in the art can be added to the medicaments according to the invention.

The medicaments according to the invention are suitable for influencing KCNQ2/3 channels and exert an agonistic or antagonistic action, in particular an agonistic action.

The medicaments according to the invention are preferably suitable for the treatment of disorders or diseases that are mediated at least in part by KCNQ2/3 channels.

The medicaments according to the invention are suitable preferably for the treatment of one or more diseases selected from the group consisting of pain, especially pain selected from the group consisting of acute pain, chronic pain, neuropathic pain, muscular pain and inflammatory pain; epilepsy, urinary incontinence, anxiety, dependency, mania, bipolar disorders, migraine, cognitive diseases, dystonia-associated dyskinesias and/or urinary incontinence.

The medicaments according to the invention are suitable particularly preferably for the treatment of pain, most particularly preferably of chronic pain, neuropathic pain, inflammatory pain and muscular pain.

The medicaments according to the invention are also particularly preferably suitable for the treatment of epilepsy.

The invention further provides the use of at least one substituted nicotinamide according to the invention, and optionally one or more pharmaceutically acceptable auxiliary substances, in the preparation of a medicament for the treatment of disorders or diseases that are mediated at least in part by KCNQ2/3 channels.

Preference is given to the use of at least one substituted nicotinamide according to the invention, and optionally one or more pharmaceutically acceptable auxiliary substances, in the preparation of a medicament for the treatment of pain, especially pain selected from the group consisting of acute pain, chronic pain, neuropathic pain, muscular pain and inflammatory pain; epilepsy, urinary incontinence, anxiety, dependency, mania, bipolar disorders, migraine, cognitive diseases, dystonia-associated dyskinesias and/or urinary incontinence.

Particular preference is given to the use of at least one substituted nicotinamide according to the invention, and optionally one or more pharmaceutically acceptable auxiliary substances, in the preparation of a medicament for the treatment of pain, most particularly preferably chronic pain, neuropathic pain, inflammatory pain and muscular pain.

Particular preference is given also to the use of at least one substituted nicotinamide according to the invention, and optionally one or more pharmaceutically acceptable auxiliary substances, in the preparation of a medicament for the treatment of epilepsy.

The invention further provides at least one substituted nicotinamide according to the invention, and optionally one or more pharmaceutically acceptable auxiliary substances, for the treatment of disorders or diseases that are mediated at least in part by KCNQ2/3 channels.

The invention further provides at least one substituted nicotinamide according to the invention, and optionally one or more pharmaceutically acceptable auxiliary substances, for the treatment of pain, especially pain selected from the group consisting of acute pain, chronic pain, neuropathic pain, muscular pain and inflammatory pain; epilepsy, urinary incontinence, anxiety, dependency, mania, bipolar disorders, migraine, cognitive diseases, dystonia-associated dyskinesias and/or urinary incontinence.

Particular preference is given to at least one substituted nicotinamide according to the invention, and optionally one or more pharmaceutically acceptable auxiliary substances, for the treatment of pain, most particularly preferably of chronic pain, neuropathic pain, inflammatory pain and muscular pain.

Particular preference is given also to at least one substituted nicotinamide according to the invention, and optionally one or more pharmaceutically acceptable auxiliary substances, for the treatment of epilepsy.

The effectiveness against pain can be shown, for example, in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363). The effectiveness against epilepsy can be demonstrated, for example, in the DBA/2 mouse model (De Sarro et al., Naunyn-Schmiedeberg's Arch. Pharmacol. 2001, 363, 330-336).

The substituted nicotinamides according to the invention preferably have an $EC_{50}$ value of not more than 5 μM or not more than 3 μM, more preferably not more than 2 μM or not more than 1 μM, yet more preferably not more than 0.9 μM or not more than 0.6 μM, most preferably not more than 0.5 μM or not more than 0.3 μM and especially not more than 0.2 μM or not more than 0.1 μM. Methods for determining the $EC_{50}$ value are known to the person skilled in the art. The $EC_{50}$ value is preferably determined by fluorimetry, particularly preferably as described under "Pharmacological Experiments".

The invention further provides processes for the preparation of the substituted nicotinamides according to the invention.

The chemicals and reaction components used in the reactions described hereinbelow are available commercially or can in each case be prepared by conventional methods known to the person skilled in the art.

General Reaction Schemes

Scheme 1:

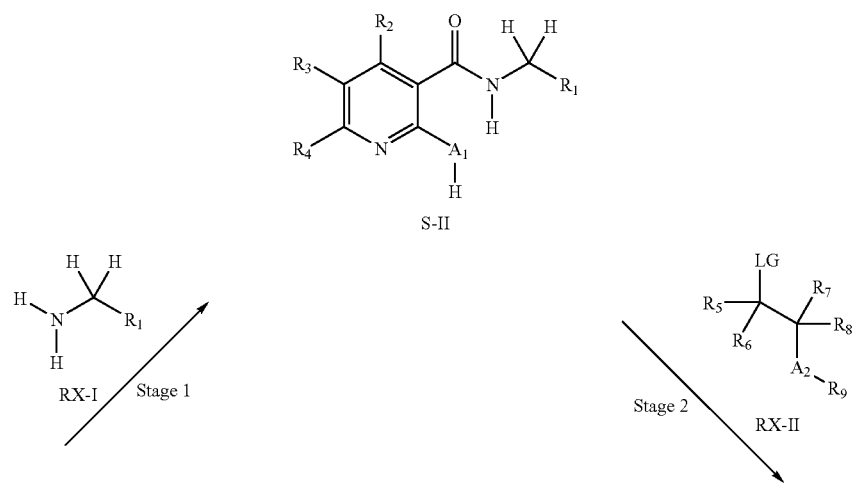

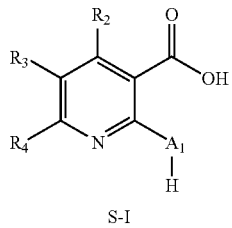

S-I

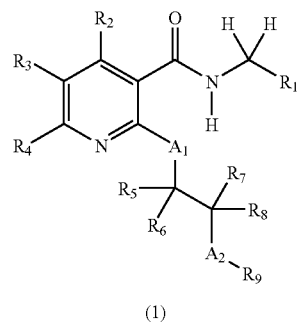

(1)

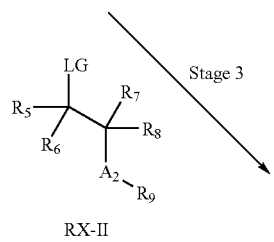

RX-II

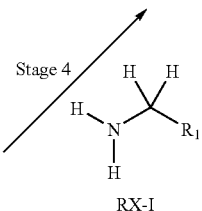

RX-I

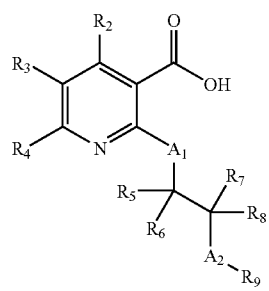

S-III

In stage 1, acids of the general formula S-I are reacted with amines of the general formula RX-I in a reaction medium, preferably selected from the group consisting of ether, THF, MeCN, MeOH, EtOH, DMF and DCM, optionally in the presence of at least one coupling reagent, preferably selected from the group consisting of BOP, DCC, EDC, HATU, HBTU and HOAt, optionally in the presence of at least one inorganic base, preferably selected from the group consisting of potassium carbonate and caesium carbonate, or organic base, preferably selected from the group consisting of $NEt_3$, pyridine, DMAP and DIPEA, preferably at temperatures of from −70° C. to 100° C., optionally in the presence of microwave radiation, to give amides of the general formula S-II.

Alternatively, according to stage 1 the acids of the general formula S-I are first converted into the corresponding acid chlorides using reagents, for example selected from the group $(COCl)_2$, $PCl_3$, $POCl_3$ and $SOCl_2$, in a reaction medium, preferably selected from the group consisting of toluene, DMF, DCM and pyridine, at temperatures of from −70° C. to 100° C., optionally in the presence of microwave radiation, and then reacted with amines of the general formula RX-I in a reaction medium, preferably selected from the group consisting of ether, THF, MeCN, MeOH, EtOH, DMF and DCM, with or without the addition of at least one organic or inorganic base, for example $NEt_3$, DMAP, pyridine or DIPEA, optionally in the presence of at least one organic base, preferably selected from the group consisting of $NEt_3$, DMAP, pyridine and DIPEA, or inorganic base, at temperatures of preferably from −70° C. to 100° C., optionally in the presence of microwave radiation, to give amides of the general formula S-II.

In stage 2, compounds of the general formula S-II are reacted with compounds of the general formula RX-II, wherein LG represents a leaving group, preferably chlorine, bromine or iodine, in a reaction medium, preferably selected from the group consisting of acetone, ethanol, ether, methanol, THF, MeCN, toluene and DMF, optionally in the presence of at least one inorganic base, preferably selected from the group consisting of potassium carbonate, butyllithium, sodium hydride, sodium methylate or potassium tert-butylate, or organic base, preferably selected from the group consisting of $NEt_3$, pyridine, DMAP and DIPEA, preferably at temperatures of from −70° C. to 100° C., optionally in the presence of microwave radiation, to give compounds of the general formula (1).

In stage 3, acids of the general formula S-I are reacted with compounds of the general formula RX-II, wherein LG represents a leaving group, preferably chlorine, bromine or iodine, according to the process described in stage 2 to give compounds of the general formula S-III.

In stage 4, acids of the general formula S-III are reacted with amines of the general formula RX-I according to the process described in stage 1 to give compounds of the general formula (1).

Scheme 2 (only for $A_1$ = S or O):
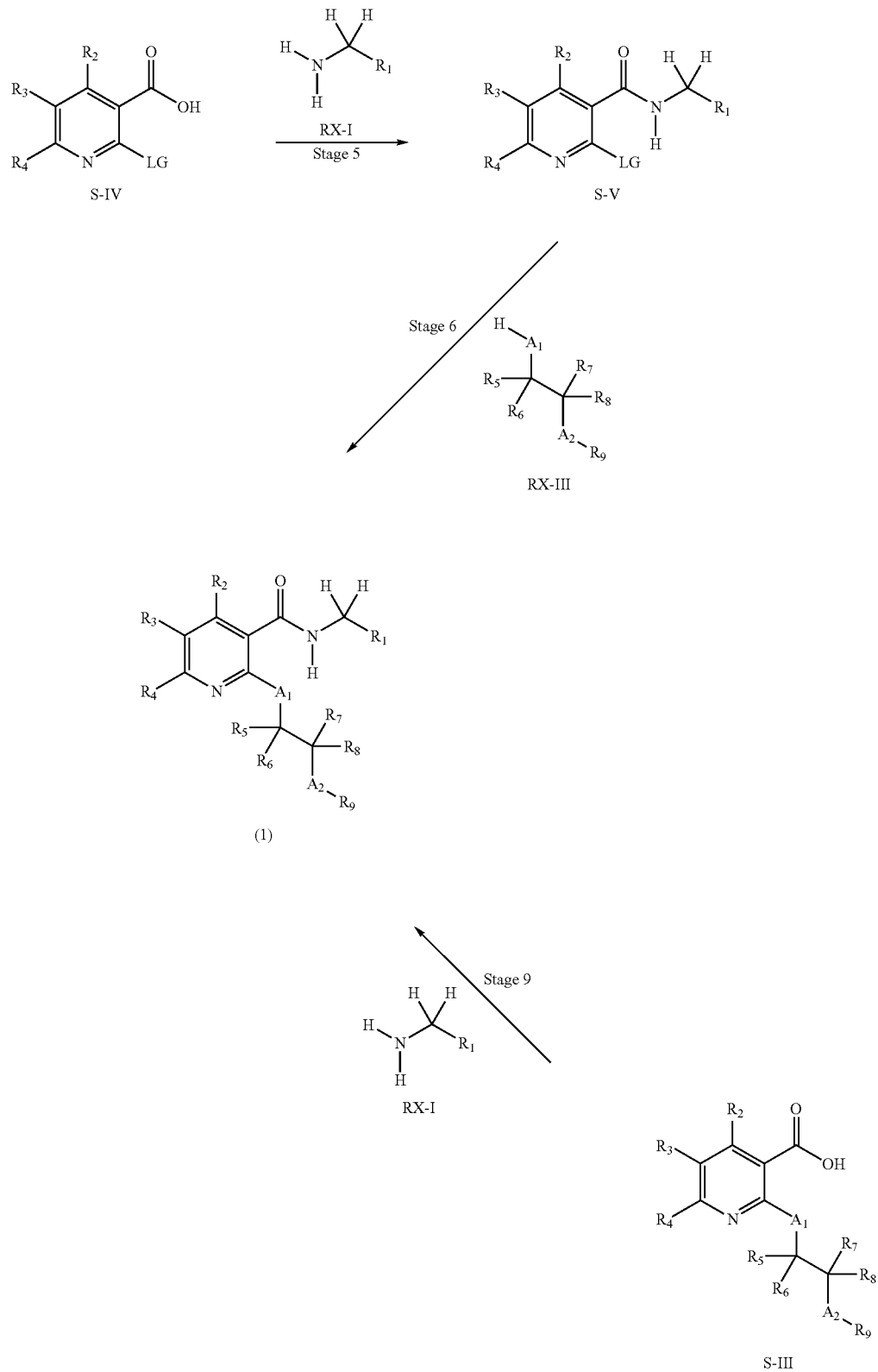

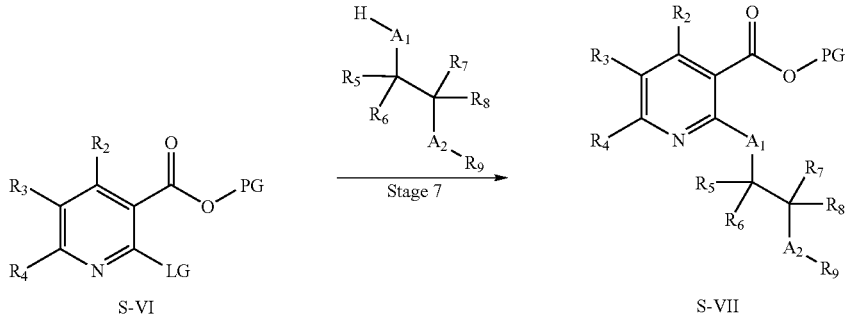

In stage 5, acids of the general formula S-IV, wherein LG represents a leaving group, preferably a halide or methanesulfonate, particularly preferably chlorine, are reacted with amines of the general formula RX-I according to the processes described in stage 1 to give compounds of the general formula S-V.

In stage 6, compounds of the general formula S-V are reacted with compounds of the general formula RX-III, wherein $A_1$ represents O or S, in a reaction medium, preferably ether, THF, MeCN, toluene or DMF, optionally in the presence of at least one inorganic base, preferably selected from the group consisting of potassium carbonate, sodium hydride, sodium methylate or potassium tert-butylate, at temperatures of from −70° C. to 100° C., optionally in the presence of microwave radiation, to give compounds of the general formula (1).

In stage 7, compounds of the general formula S-VI, wherein LG represents a leaving group, preferably a halide or methanesulfonate, particularly preferably chlorine, and PG represents a protecting group, preferably methyl or ethyl, are reacted with compounds of the general formula RX-III, wherein $A_1$ represents S or O, according to the processes described in stage 6 to give compounds of the formula S-VII.

In stage 8, esters of the general formula S-VII, wherein PG represents a protecting group, preferably methyl or ethyl, are cleaved in a reaction medium, preferably selected from the group consisting of ethanol, methanol, MeCN, THF and water, or arbitrary mixtures thereof, optionally with the addition of an inorganic base, preferably potassium hydroxide, sodium hydroxide or lithium hydroxide, at a temperature of from 0° C. to 120° C., to give acids of the general formula S-III.

The reaction at stage 9 corresponds to stage 1 in Scheme 1.

Description of the Syntheses

Abbreviations

AcOH acetic acid
aq. aqueous
d days
BOP 1-benzotriazolyloxy-tris-(dimethylamino)-phosphonium hexafluorophosphate
brine saturated sodium chloride solution DCC N,N'-dicyclohexylcarbodiimide
DCM dichloromethane
DIPEA N,N-diisopropylethylamine
DMF N,N-dimethylformamide
DMAP 4-dimethylamino-pyridine
EDC N-(3-dimethylaminopropyl)-N'-ethyl-carbodiimide
EA ethyl acetate
ether diethyl ether
EtOH ethanol
sat. saturated
h hour(s)
HATU O-(7-aza-benzotriazol-1-yl)-N,N,N',N'-tetramethyluronium hexafluorophosphate
HBTU 0-(benzotriazol-1-yl)-N,N,N',N'-tetramethyluronium hexafluorophosphate
HOAt 1-hydroxy-7-azabenzotriazole
sol. solution
LG leaving group
m/z mass-to-charge ratio
MeCN acetonitrile
MeOH methanol
min minutes
MS mass spectrometry
N/A not available
$NEt_3$ triethylamine
RG retigabine
RT room temperature 23±7° C.
CC column chromatography on silica gel
TBTU 0-(benzotriazol-1-yl)-N,N,N',N'-tetramethyluronium tetrafluoroborate
THF tetrahydrofuran
vv ratio by volume All starting materials not described explicitly were either available commercially (suppliers can be found, for example, in the Symyx® Available Chemicals database of MDL, San Ramon, US) or their synthesis has already been described exactly in the specialist literature (experimental procedures can be found, for example, in the Reaxys® database of Elsevier, Amsterdam, NL) or can be prepared by methods known to the person skilled in the art.

Silica gel 60 (0.040-0.063 mm) was used as the stationary phase for column chromatography (CC).

The analytical characterization of all intermediates and exemplary compounds was carried out by means of $^1$H-NMR spectroscopy. Investigations by mass spectrometry (MS, m/z indicated for [M+H]$^+$) were additionally carried out for all exemplary compounds and chosen intermediates.

Synthesis of the Intermediates

Synthesis of intermediate VB006:
2-(4-(4-Fluorophenyl)butyl)-nicotinic acid 4.4 ml (11.0 mmol, 2.5M in hexane) of BuLi solution were added dropwise at −10° C. to a solution of 1.54 ml (11.0 mmol) of diisopropylamine in THF (10 ml). Stirring was then carried out for a further 30 min at −10° C. This solution was added dropwise at −75° C. to a solution of 685 mg (5.0 mmol) of 2-methyl-nicotinic acid in THF (2 ml). Stirring was then carried out for 30 min at −75° C. and for 60 min at 0° C., followed by cooling to −55° C. At that temperature, 1.62 g (7.5 mmol) of 1-(3-bromopropyl)-4-fluorobenzene were added and the reaction solution was stirred for 1 h at −55° C. After warming to RT and stirring for a further 16 h at RT, water (30 ml) and conc. hydrochloric acid (3 ml) were added. Extraction with EA (2×30 ml) was then carried out. The combined organic phases were dried over MgSO$_4$, filtered and concentrated in vacuo. The residue was purified by means of CC (EA), yielding 1.28 g (4.7 mmol, 93%) of 2-(4-(4-fluorophenyl)butyl)-nicotinic acid.

Synthesis of intermediate VB007:
2-(4-Phenylbutyl)nicotinic acid

Starting from 2.1 g (15.0 mmol) of 2-methyl-nicotinic acid and 5.5 g (22.5 mmol) of 1-iodo-3-phenyl-propane, 2.9 g (11.3 mmol, 75%) of 2-(4-phenylbutyl)nicotinic acid were obtained according to the process described in precursor VB006.

Synthesis of intermediate VB008:
2-(3-(Phenylsulfonyl)propyl)-nicotinic acid

Starting from 2.1 g (15.0 mmol) of 2-methyl-nicotinic acid and 4.6 g (22.5 mmol) of (2-chloroethyl)-phenylsulfone, 0.7 g (2.4 mmol, 16%) of 2-(3-(phenylsulfonyl)propyl)-nicotinic acid was obtained according to the process described in precursor VB006.

Synthesis of intermediate VC001: (2-Chloro-propan-1-yl)-(phenyl)sulfane/ (1-Chloropropan-2-yl)(phenyl)sulfane (5:4 mixture)

a) Synthesis of 1-(phenylthio)propan-2-one
13.8 g (100.0 mmol) of K$_2$CO$_3$ were added to a solution of 5.1 ml (50.0 mmol) of thiophenol and 4.22 ml (52.5 mmol) of chloroacetone in DMF (30 ml), and the mixture was stirred for 2 h at RT. Concentration in vacuo was then carried out. The residue was purified by means of CC (EA/hex 15:85), yielding 7.7 g (46.3 mmol, 93%) of 1-(phenylthio)propan-2-one.
b) Synthesis of 1-(phenylthio)propan-2-ol
732 mg (19.2 mmol) of NaBH$_4$ were added in portions, while cooling (ice bath), to a solution of 2.46 g (14.8 mmol) of 1-(phenylthio)propan-2-one in methanol (18 ml). Stirring was then carried out for a further 2 h while cooling (ice bath). The mixture was then quenched with AcOH (17 ml) and then concentrated in vacuo. The residue was taken up in an ether/water mixture and neutralized with NaHCO$_3$. The phases were separated and the organic phase was dried over MgSO$_4$, filtered and concentrated in vacuo. The residue was purified by means of CC (EA/hex 15:85), yielding 1.3 g (7.7 mmol, 52%) of 1-(phenylthio)propan-2-ol.

c) Synthesis of a (2-chloro-propan-1-yl)-(phenyl)sulfane/(1-chloropropan-2-yl)(phenyl)sulfane 5:4 mixture
A solution of 1.7 ml (23.0 mmol) of thionyl chloride in toluene (20 ml) was added dropwise, while cooling (ice bath), to a solution of 1.29 g (7.7 mmol) of 1-(phenyl-thio)propan-2-ol and 92 μl (1.2 mmol) of pyridine in toluene (30 ml). The mixture was then heated for 3 h under reflux. After cooling to RT, quenching with an ice/water mixture was carried out. The phases were separated and the aqueous phase was extracted again with toluene. The combined organic phases were dried over MgSO$_4$, filtered and concentrated in vacuo. The residue was purified by means of CC (EA/hex 1:9), yielding 1.13 g (6.1 mmol, 79%) of a (2-chloro-propan-1-yl)-(phenyl)sulfane/(1-chloropropan-2-yl)(phenyl)sulfane (5:4) mixture. This mixture was used in subsequent reactions without being purified further.

Synthesis of intermediate VC005:
1-(3-Bromo-1,1-difluoropropyl)-4-fluoro-benzene a) Synthesis of 2-(2-(4-fluorophenyl)-1,3-dithiolan-2-yl) ethyl acetate
1.79 g (19.0 mol) of ethane-1,2-dithiol and 680 mg (4.76 mmol) of boron trifluoride etherate were added in succession at 0° C. to a solution of 2.0 g (9.5 mmol) of 3-(4-fluorophenyl)-3-oxopropyl acetate in DCM (40 ml). The mixture was then stirred for 16 h at RT and subsequently neutralized with a 10M aq. NaOH sol. Extraction with DCM (3×100 ml) was then carried out and the combined organic phases were washed with water and brine, dried over Na$_2$SO$_4$, filtered and concentrated in vacuo. CC (hexane/EA 24:1) of the residue yielded 1.8 g (6.3 mmol, 66%) of 2-(2-(4-fluoro-phenyl)-1,3-dithiolan-2-yl)ethyl acetate.
b) Synthesis of 3,3-difluoro-3-(4-fluorophenyl)propyl acetate
A 30% HF-pyridine solution (7 ml) and a solution of 500 mg (1.75 mmol) of 2-(2-(4-fluorophenyl)-1,3-dithiolan-2-yl) ethyl acetate in DCM (2 ml) were added in succession at −78° C. to a solution of 2.0 g (7.0 mmol) of 1,3-dibromo-5,5-dimethylhydantoin in DCM (4 ml) in a plastics reaction vessel. The mixture was warmed to 0° C. in the course of 2 h, with stirring, and then neutralized with a sat. aq. NaHCO$_3$ sol. Extraction with DCM (3×60 ml) was then carried out. The combined organic phases were washed with water and brine, dried over Na$_2$SO$_4$, filtered and concentrated in vacuo. There were obtained as residue 250 mg (1.08 mmol, 62%) of 3,3-difluoro-3-(4-fluorophenyl)propyl acetate, which was reacted further without additional purification.
c) Synthesis of 3,3-difluoro-3-(4-fluorophenyl)propan-1-ol
A 35% aq. NaOH sol. (6 ml) was added to a solution of 1.9 g (8.2 mmol) of 3,3-difluoro-3-(4-fluorophenyl)propyl acetate in EtOH (25 ml), and the mixture was stirred for 2 h at RT. Concentration in vacuo was then carried out and the residue was taken up in water (80 ml). The solution was extracted with EA (3×80 ml) and the combined organic phases were washed with water and brine, dried over Na$_2$SO$_4$, filtered and concentrated in vacuo. CC (hexane/EA 9:1) of the residue yielded 1.1 g (5.8 mmol, 71%) of 3,3-difluoro-3-(4-fluorophenyl)propan-1-ol.
d) Synthesis of 1-(3-bromo-1,1-difluoropropyl)-4-fluorobenzene
3.1 g (9.5 mmol) of tetrabromomethane were added to a solution of 1.0 g (5.3 mmol) of 3,3-difluoro-3-(4-fluorophenyl)propan-1-ol in DCM (20 ml) and cooled to 0° C. At that temperature, 2.48 g (9.5 mmol) of triphenylphosphine were added in portions. Stirring was then carried out for 3 h at RT. The mixture was then diluted with water (50 ml) and extracted with EA (3×60 ml). The combined organic phases were washed with water and brine, dried over Na$_2$SO$_4$, filtered and concentrated in vacuo. CC (hexane/EA 24:1) of the residue yielded 1.25 g (5.0 mmol, 94%) of 1-(3-bromo-1,1-difluoropropyl)-4-fluorobenzene.

Synthesis of intermediate VC006:
1-(3-Bromobutyl)-3-(trifluoromethyl)benzene a) Synthesis of 4-(3-(trifluoromethyl)phenyl)butan-2-ol 590 mg (15.4 mmol) of LiAlH$_4$ were added in portions at 0° C. to a solution of 2.2 g (10.3 mmol) of 4-(3-(trifluoromethyl)phenyl)but-3-en-2-one in THF (20 ml), and stirring was then carried out for 1 h at RT. The mixture was then quenched at 0° C. with a sat. aq. Na$_2$SO$_4$ sol. and the reaction solution was filtered over kieselguhr. The filtrate was extracted with EA (3×60 ml) and the combined organic phases were washed with water, dried over Na$_2$SO$_4$, filtered and concentrated in vacuo. There were obtained as residue 2.0 g (9.2 mmol, 89%) of 4-(3-(trifluoromethyl)phenyl)-butan-2-ol, which was reacted further without additional purification.

b) Synthesis of 1-(3-bromobutyl)-3-(trifluoromethyl)benzene 750 mg (11.0 mmol) of imidazole and 2.88 g (11.0 mmol) of triphenylphosphine were added to a solution of 2.0 g (9.2 mmol) of 4-(3-(trifluoromethyl)phenyl)butan-2-ol in DCM (10 ml). 570 μl (11.0 mmol) of bromine were added dropwise at 0° C., and stirring was carried out for 1 h at RT. The mixture was then concentrated in vacuo. CC (hexane) of the residue yielded 2.0 g (7.1 mmol, 78%) of 1-(3-bromobutyl)-3-(trifluoromethyl)benzene.

Synthesis of Further Intermediates

The synthesis of further intermediates was carried out according to the processes already described. Table 1 shows which compound was prepared by which process. It will be clear to the person skilled in the art which starting materials and reagents were used in each case.

TABLE 1

| Intermediate | Chemical name | Preparation analogous to intermediate |
| --- | --- | --- |
| VB003 | 2-(3-(Phenylthio)propyl)nicotinic acid | VB006 |
| VB004 | 2-(3-(3-(Trifluoromethyl)phenyl-thio)propyl)nicotinic acid | VB006 |
| VB005 | 2-(4-(3-Trifluoromethyl-phenyl)butyl)nicotinic acid | VB006 |
| VB009 | 2-(3-(3-(Trifluoromethyl)-phenylsulfonyl)propyl)nicotinic acid | VB006 |
| VC002 | (2-Chloro-propan-1-yl)(4-fluoro-phenyl)sulfane/(1-Chloropropan-2-yl)(4-fluoro-phenyl)sulfane (3:2 mixture) | VC001 |
| VC003 | (2-Chloro-propan-1-yl)(3-trifluoro-methyl-phenyl)sulfane/(1-Chloro-propan-2-yl)(3-trifluoromethyl-phenyl)-sulfane (5:4 mixture) | VC001 |
| VC004 | (2-Chloro-propan-1-yl)(phenyl)sulfane/(1-Chloropropan-2-yl)(phenyl)sulfane (5:13 mixture) | see Example 16 |

Synthesis of the Exemplary Compounds

Synthesis of exemplary compound 1: 2-(3-Phenyl-propylsulfanyl)-N-(thiophen-2-yl-methyl)-pyridine-3-carboxylic acid amide

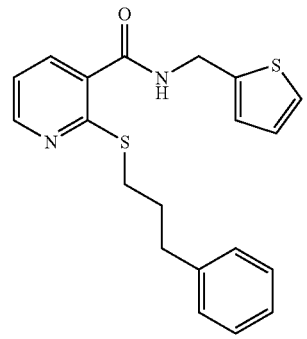

227 mg (1.65 mmol) of K$_2$CO$_3$ were added to a solution of 375 mg (1.5 mmol) of 2-mercapto-N-(thiophen-2-ylmethyl)nicotinamide in DMF (3.5 ml), and stirring was carried out for 30 min at RT. 369 mg (1.5 mmol) of 1-iodo-3-phenylpropane were then added and stirring was carried out for a further 3 d at RT. The mixture was then concentrated in vacuo and the residue was taken up in an EA/water mixture. The organic phase was separated off and the aqueous phase was extracted again with EA. The combined organic phases were dried over MgSO$_4$, filtered and concentrated in vacuo. The residue was purified by means of CC (EA/hex 1:1), yielding 382 mg (1.0 mmol, 69%) of 2-(3-phenyl-propylsulfanyl)-N-(thiophen-2-yl-methyl)-pyridine-3-carboxylic acid amide. MS: m/z 369.1 [M+H]$^+$.

Synthesis of exemplary compound 3: 2-[(3-Oxo-3-phenyl-propyl)sulfanyl]-N-(thiophen-2-yl-methyl)-pyridine-3-carboxylic acid amide

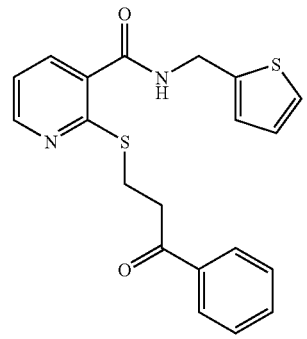

227 mg (1.65 mmol) of K$_2$CO$_3$ were added to a solution of 375 mg (1.5 mmol) of 2-mercapto-N-(thiophen-2-ylmethyl)nicotinamide in DMF (3.5 ml), and stirring was carried out for 30 min at RT. 252 mg (1.5 mmol) of 3-chloro-1-phenylpropan-1-one were then added and stirring was carried out for a further 2 d at RT. The mixture was then concentrated in vacuo and the residue was taken up in a mixture of EA and a 1N aq. NaHCO$_3$ sol. The organic phase was separated off and the aqueous phase was extracted again with EA. The combined organic phases were dried over MgSO$_4$, filtered and concentrated in vacuo. The residue was purified by means of CC (EA/hex 1:1), and subsequent crystallization (EA/hexane) yielded 73 mg (0.2 mmol, 13%) of 2-[(3-oxo-3-phenyl-propyl)sulfanyl]-N-(thiophen-2-yl-methyl)-pyridine-3-carboxylic acid amide. MS: m/z 383.1 [M+H]⁺.

Synthesis of exemplary compound 13: N-(Thiophen-2-yl-methyl)-2-[3-[[3-(trifluoromethyl)phenyl]sulfanyl]-propyl]-pyridine-3-carboxylic acid amide

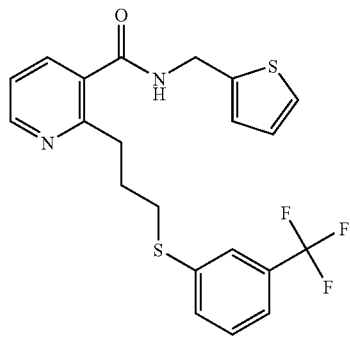

91 mg (0.6 mmol) of CDI were added to a solution of 240 mg (0.7 mmol) of 2-(3-(3-(trifluoromethyl)phenylthio)propyl)nicotinic acid (VB004) in DCM (7 ml), and stirring was carried out for 30 min at RT. 79 mg (0.7 mmol) of 2-(aminomethyl)thiophene were then added and stirring was carried out for a further 5 d at RT. The mixture was then washed with a 4M aq. NH₄Cl sol. (2×10 ml) and a 1M NaHCO₃ sol. (2×10 ml). The organic phase was dried over MgSO₄, filtered and concentrated in vacuo. The residue was purified by means of CC (EA), yielding 134 mg (0.3 mmol, 44%). MS: m/z 437.1 [m+H]⁺.

Synthesis of exemplary compound 16: 2-(2-Phenylsulfanyl-propylsulfanyl)-N-(thiophen-2-yl-methyl)-pyridine-3-carboxylic acid amide

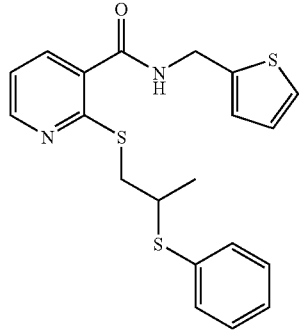

1.51 g (11.0 mmol) of K₂CO₃ were added to a solution of 1.25 g (5.0 mmol) of 2-mercapto-N-(thiophen-2-ylmethyl)nicotinamide in DMF (12 ml) and stirring was carried out for 1 h at RT. 930 mg (5.0 mmol) of a (2-chloro-propan-1-yl)(phenyl)-sulfane/ (1-chloropropan-2-yl)(phenyl)sulfane 5:4 mixture (VC001) were then added and stirring was carried out for a further 18 h at RT. The mixture was then concentrated in vacuo. The residue was taken up in an EA/water mixture and the phases were separated. The aqueous phase was extracted again with EA and the combined organic phases were dried over MgSO₄, filtered and concentrated in vacuo. By means of CC (EA/hex 3:7→1:1) there were recovered 400 mg (2.1 mmol, 43%) of a (2-chloro-propan-1-yl)-(phenyl)sulfane/(1-chloropropan-2-yl)(phenyl)-sulfane 5:13 mixture (VC004) and a mixed fraction containing 2-(2-phenylsulfanyl-propylsulfanyl) -N-(thiophen-2-yl-methyl)-pyridine-3-carboxylic acid amide. From the latter there were isolated by crystallization (EA) 255 mg (0.6 mmol, 13%) of 2-(2-phenylsulfanyl-propylsulfanyl)-N-(thiophen-2-yl-methyl)-pyridine-3-carboxylic acid amide. MS: m/z 401.1 [M+H]⁺.

Synthesis of exemplary compound 17: 2-[3-(4-Fluorophenyl)-propylsulfanyl]-N-(thiophen-2-yl-methyl)-pyridine-3-carboxylic acid amide

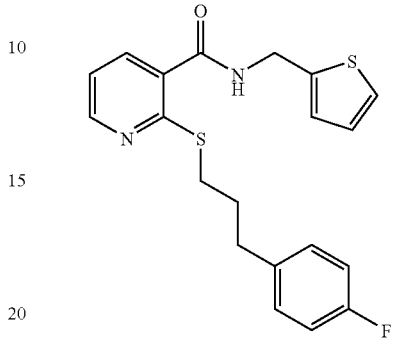

227 mg (1.65 mmol) of K₂CO₃ were added to a solution of 375 mg (1.5 mmol) of 2-mercapto-N-(thiophen-2-ylmethyl)nicotinamide in DMF (6 ml) and stirring was carried out for 1 h at RT. 325 mg (1.5 mmol) of 1-(3-bromopropyl)-4-fluorobenzene were then added and stirring was carried out for a further 16 h at RT. The mixture was then concentrated in vacuo and the residue was taken up in an EA/water mixture. The organic phase was separated off and the aqueous phase was extracted again with EA. The combined organic phases were dried over MgSO₄, filtered and concentrated in vacuo. The residue was purified by means of CC (EA/hex 1:2), yielding 428 mg (1.1 mmol, 74%) of 2-[3-(4-fluorophenyl)-propylsulfanyl]-N-(thiophen-2-yl-methyl) -pyridine-3-carboxylic acid amide. MS: m/z 3871 [M+H]⁺.

Synthesis of exemplary compound 21: N-(Thiophen-2-yl-methyl)-2-[4-[3-(trifluoromethyl)-phenyl]-butyl]-pyridine-3-carboxylic acid amide

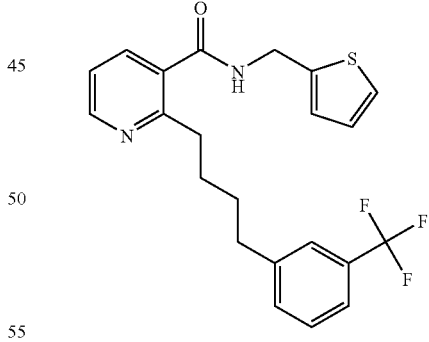

NEt₃ was added to a solution of 323 mg (1.0 mmol) of 2-(4-(3-trifluoromethyl-phenyl)butyl)nicotinic acid (VB005), 113 mg (1.0 mmol) of 2-(aminomethyl)-thiophene and 381 mg (1.0 mmol) of HATU in THF (8 ml) and stirring was carried out for 4 d at RT. The mixture was then concentrated in vacuo. The residue was taken up in EA and washed with a 1M aq. NH₄Cl sol. and a 1M aq. NaHCO₃ sol. The organic phase was dried over MgSO₄, filtered and concentrated in vacuo. The residue was purified by means of CC (EA/hex 3:1), yielding 221 mg (0.5 mmol, 53%). MS: m/z 419.1 [M+H]⁺.

Synthesis of exemplary compound 42: N-(3,3-Dimethyl-butyl)-2-[3-(4-fluorophenyl)-propylsulfanyl]-pyridine-3-carboxylic acid amide

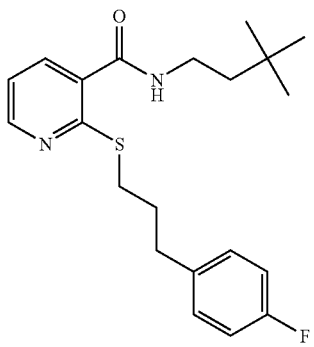

a) Synthesis of 2-(3-(4-fluorophenyl)propylthio)nicotinic acid 4.9 g (35.8 mmol) of K₂CO₃ were added to a solution of 2.5 g (16.3 mmol) of 2-mercapto-nicotinic acid in DMF (40 ml), and the mixture was stirred for 30 min at RT. 3.5 g (16.3 mmol) of 1-(3-bromopropyl)-4-fluorobenzene were then added and stirring was carried out for a further 72 h at RT. The mixture was then diluted with water and EA and adjusted to pH 5-6 with 5M acetic acid. The organic phase was separated off, washed with water, dried over MgSO₄, filtered and concentrated in vacuo. CC (EA/hexane 1:2→5:1) of the residue yielded 2.2 g (7.6 mmol, 47%) of 2-(3-(4-fluoro-phenyl)propylthio)nicotinic acid.

b) Synthesis of N-(3,3-dimethyl-butyl)-2-[3-(4-fluorophenyl)-propylsulfanyl]-pyridine-3-carboxylic acid amide 274 mg (0.72 mmol) of HATU and 100 ml (0.72 mmol) of NEt₃ were added to a solution of 200 mg (0.69 mmol) of 2-(3-(4-fluorophenyl)propylthio)nicotinic acid and 92 ml (0.69 mmol) of 3,3-dimethyl-butylamine in THF (11 ml), and the mixture was stirred for 16 h at RT. Dilution with EA was then carried out. The organic phase was separated off, washed with a 1M aq. Na₂CO₃ sol. and a 4M aq. NH₄Cl sol., dried over MgSO₄, filtered and concentrated in vacuo. CC (hexane/EA 2:1) of the residue yielded 173 mg (0.46 mmol, 67%) of N-(3,3-dimethyl-butyl)-2-[3-(4-fluorophenyl)-propylsulfanyl]-pyridine-3-carboxylic acid amide. MS: m/z 375.2 [M+H]⁺.

Synthesis of exemplary compound 50: N-(5-Bicyclo[2.2.1]heptanyl-methyl)-2-[[3-(4-fluorophenyl)-3-hydroxy-propyl]sulfanyl]-pyridine-3-carboxylic acid amide

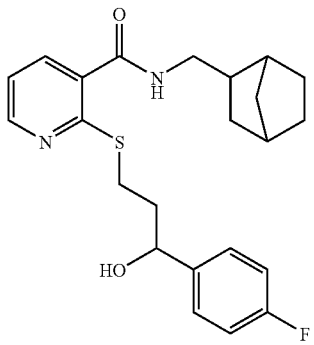

A solution of 400 mg (0.97 mmol) of N-(5-bicyclo[2.2.1]heptanyl-methyl)-2-[[3-(4-fluorophenyl)-3-oxo-propyl]sulfanyl]-pyridine-3-carboxylic acid amide (exemplary compound 43) in MeOH (10 ml) was cooled to 0° C., and 18 mg (0.49 mmol) of NaBH₄ were added in portions. Stirring was then carried out for 2 h at 0° C. and for 1 h at RT. The reaction solution was then poured onto ice-water and extraction with DCM was carried out. The organic phase was dried over MgSO₄, filtered and concentrated in vacuo. CC (hexane/EA 2:1→1:1) of the residue yielded 180 mg (0.43 mmol, 45%) of N-(5-bicyclo[2.2.1]heptanyl-methyl)-2-[[3-(4-fluorophenyl)-3-hydroxy-propyl]sulfanyl]-pyridine-3-carboxylic acid amide. MS: m/z 415.2 [m+H]⁺.

Synthesis of exemplary compound 51: N-(5-Bicyclo[2.2.1]heptanyl-methyl)-2-[3-(4-fluorophenyl)-propylsulfanyl]-pyridine-3-carboxylic acid amide

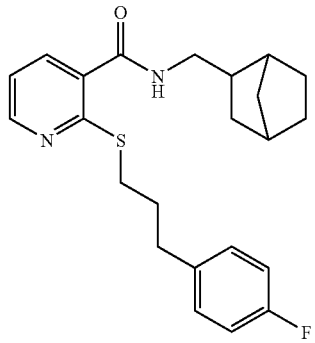

a) Synthesis of N-(bicyclo[2.2.1]heptan-2-ylmethyl)-2-mercapto-nicotinamide 5.0 g (40.0 mmol) of bicyclo[2.2.1]heptan-2-ylmethanamine, 16.0 g (42.0 mmol) of HATU and 5.8 ml (42.0 mmol) of NEt₃ were added in succession to a solution of 6.2 g (40.0 mmol) of 2-mercapto-nicotinic acid in THF (320 ml), and the mixture was stirred for 4 d at RT. Dilution with EA was then carried out. The organic phase was separated off, washed with a 1M aq. Na₂CO₃ sol. and a 4M aq. NH₄Cl sol., dried over MgSO₄, filtered and concentrated in vacuo. CC (hexane/EA 7:3→1:1→3:7) was carried out with the residue. The resulting prepurified product was dissolved in 1N aq. NaOH (100 ml) and the solution was washed with ether. The aqueous phase was adjusted to pH ~2 with 2M hydrochloric acid. The resulting precipitate was filtered off and then washed with pentane and dried in vacuo. 5.3 g (20.2 mmol, 50%) of N-(bicyclo[2.2.1]heptan-2-ylmethyl)-2-mercapto-nicotinamide were obtained.

b) Synthesis of N-(5-bicyclo[2.2.1]heptanyl-methyl)-2-[3-(4-fluorophenyl)-propyl-sulfanyl]-pyridine-3-carboxylic acid amide 178 mg (1.29 mmol) of K₂CO₃ were added to a solution of 308 mg (1.18 mmol) of N-(bicyclo[2.2.1]heptan-2-ylmethyl)-2-mercapto-nicotinamide in DMF (5 ml), and the mixture was stirred for 60 min at RT. 255 mg (1.18 mmol) of 1-(3-bromopropyl)-4-fluorobenzene were then added and the mixture was stirred for a further 16 h at RT. Dilution with water and extraction with EA were then carried out. The organic phase was washed with water, dried over MgSO₄, filtered and concentrated in vacuo. CC (hexane/EA 2:1) of the residue yielded 333 mg (0.83 mmol, 71%) of N-(5-bicyclo[2.2.1]heptanyl-methyl)-2-[3-(4-fluorophenyl)-propyl-sulfanyl]-pyridine-3-carboxylic acid amide. MS: m/z 399.2 [M+H]⁺.

Synthesis of exemplary compound 58: N-(5-Bicyclo[2.2.1]heptanyl-methyl)-2-[3-(4-hydroxyphenyl)-propylsulfanyl]-pyridine-3-carboxylic acid amide

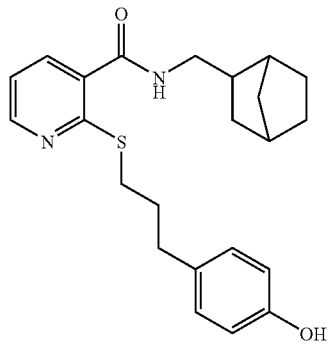

A solution of 483 mg (1.18 mmol) of N-(5-bicyclo[2.2.1]heptanyl-methyl)-2-[3-(4-methoxyphenyl)-propylsulfanyl]-pyridine-3-carboxylic acid amide (exemplary compound 56) in DCM (50 ml) was cooled to −60° C.; 11.8 ml (11.8 mmol, 1M in DCM) of boron tribromide were added at that temperature and stirring was carried out for 90 min at −60° C. After warming to RT, the mixture was quenched with a 1M aq. NaHCO$_3$ sol. and the phases were separated. The aqueous phase was extracted with EA and the organic phases were combined, washed with water, dried over MgSO$_4$, filtered and concentrated in vacuo. Crystallization (hexane/EA 2:1) of the residue yielded 393 mg (0.99 mmol, 84%) of N-(5-bicyclo[2.2.1]heptanyl-methyl)-2-[3-(4-hydroxy-phenyl)-propylsulfanyl]-pyridine-3-carboxylic acid amide. MS: m/z 397.2 [M+H]$^+$.

Synthesis of exemplary compound 112: 2-(3-Phenyl-propylsulfanyl)-6-pyrrolidin-1-yl-N-(thiophen-2-yl-methyl)-pyridine-3-carboxylic acid amide

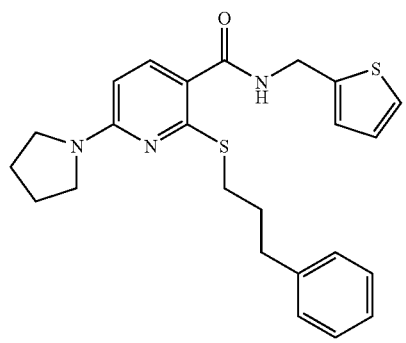

153 mg of K$_2$CO$_3$ and 71 mg (1.0 mmol) of pyrrolidine were added to a solution of 387 mg (1.0 mmol) of 6-fluoro-2-(3-phenylpropylthio)-N-(thiophen-2-ylmethyl)-pyridine-3-carboxylic acid amide (exemplary compound 225) in DMF (10 ml), and the mixture was stirred for 2 h at RT. Dilution with water and extraction with EA were then carried out. The organic phase was washed with water and brine, dried over Na$_2$SO$_4$, filtered and concentrated in vacuo. CC (hexane/EA 7:3) of the residue yielded 308 mg (0.7 mmol, 71%) of 2-(3-phenyl-propylsulfanyl)-6-pyrrolidin-1-yl -N-(thiophen-2-yl-methyl)-pyridine-3-carboxylic acid amide. MS: m/z 438.2 [M+H]$^+$.

Synthesis of exemplary compound 115: N-(5-Bicyclo[2.2.1]heptanyl-methyl)-2-[[3,3-difluoro-3-(4-fluorophenyl)-propyl]sulfanyl]-pyridine-3-carboxylic acid amide

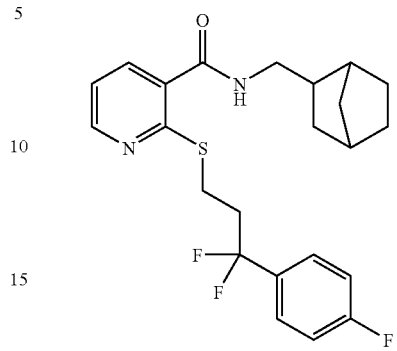

a) Synthesis of N-(bicyclo[2.2.1]heptan-2-ylmethyl)-2-mercapto-nicotinamide 4.82 g (15.0 mmol) of TBTU and 3.54 g (35 mmol) of N-methyl-morpholine were added to a solution of 1.55 g (10.0 mmol) of 2-mercapto-nicotinic acid in DMF (30 ml), and the mixture was stirred for 30 min at RT. 1.25 g (10.0 mmol) of bicyclo-[2.2.1]heptan-2-ylmethanamine were then added, and stirring was carried out for 16 h at RT. The mixture was then diluted with EA and washed with sat. aq. NH$_4$Cl sol., a 1N aq. NaHCO$_3$ sol. and brine. The organic phase was dried over Na$_2$SO$_4$, filtered and concentrated in vacuo. CC (DCM/MeOH 99:1) of the residue yielded 308 mg 1.39 g (5.3 mmol, 53%) of N-(bicyclo[2.2.1]heptan-2-ylmethyl)-2-mercapto-nicotinamide.

b) Synthesis of N-(5-bicyclo[2.2.1]heptanyl-methyl)-2-[[3,3-difluoro-3-(4-fluorophenyl)-propyl]sulfanyl]-pyridine-3-carboxylic acid 553 mg (4 mmol) of K$_2$CO$_3$ and 268 mg (1.0 mmol) of 3,3-difluoro-3-(4-fluorophenyl)-propyl methanesulfonate were added in succession to a solution of 262 mg (1.0 mmol) of N-(bicyclo[2.2.1]heptan-2-ylmethyl)-2-mercapto-nicotinamide in DMF (3 ml), and the mixture was heated for 3 h at 60° C. Dilution with water and extraction with EA were then carried out. The organic phase was washed with brine, dried over Na$_2$SO$_4$, filtered and concentrated in vacuo. CC (hexane/EA 7:3) of the residue yielded 229 mg (0.5 mmol, 53%) of N-(5-bicyclo[2.2.1]heptanyl-methyl)-2-[[3,3-difluoro-3-(4-fluoro-phenyl)-propyl]sulfanyl]-pyridine-3-carboxylic acid amide. MS: m/z 435.2 [M+H]$^+$.

Synthesis of exemplary compound 126: 2-[3-(4-Fluorophenyl)-propylsulfanyl]-N-(2-hydroxy-3,3-dimethyl-butyl)-pyridine-3-carboxylic acid amide

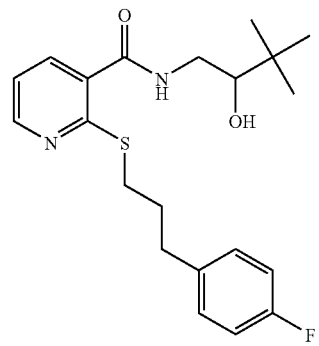

70 mg (1.8 mmol) of NaBH$_4$ were added in portions at 0° C. to a solution of 350 mg (0.9 mmol) of N-(3,3-dimethyl-2-oxo-butyl)-2-[3-(4-fluoro-phenyl)-propylsulfanyl]-pyridine-3-carboxylic acid amide (exemplary compound 125) in EtOH (7 ml). Stirring was then carried out for 2 h at RT. The mixture was then cooled to 0° C., quenched with a sat. aq. NH$_4$Cl sol. (20 ml) and concentrated in vacuo. The residue was taken up in EA and the solution was washed with a 1M aq. NaHCO$_3$ sol., water and brine, dried over Na$_2$SO$_4$, filtered and concentrated in vacuo. CC (hexane/EA 3:2) of the residue yielded 320 mg (0.82 mmol, 91%) of 2-[3-(4-fluorophenyl)-propylsulfanyl]-N-(2-hydroxy-3,3-dimethyl-butyl)-pyridine-3-carboxylic acid amide. MS: m/z 391.2 [M+H]$^+$.

Synthesis of exemplary compound 131: 3-[[[2-[3-(4-Fluorophenyl)-propylsulfanyl]-pyridine-3-carbonyl] amino]-methyl]-benzoic acid

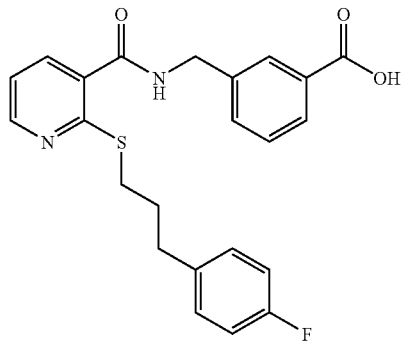

A solution of 120 mg (2.92 mmol) of lithium hydroxide monohydrate in water (4 ml) was added to a solution of 320 mg (0.73 mmol) of 3-[[[2-[3-(4-fluorophenyl)-propylsulfanyl]-pyridine-3-carbonyl]amino]-methyl]-benzoic acid methyl ester (exemplary compound 129) in a MeOH/THF mixture (2:1 vv, 9 ml), and the mixture was stirred for 16 h at RT. Concentration in vacuo was then carried out. The residue was taken up in water and washed with EA. The aqueous phase was then adjusted to pH ~2 with 2M hydrochloric acid at 0° C. The resulting precipitate was filtered off, taken up in toluene and concentrated in vacuo. The residue was washed with an ether/pentane mixture (1:4 vv), yielding 170 mg (0.4 mmol, 55%) of 3-[[[2-[3-(4-fluorophenyl)-propylsulfanyl]-pyridine-3-carbonyl]amino]-methyl]-benzoic acid. MS: m/z 425.1 [m+H]$^+$.

Synthesis of exemplary compound 143: 2-[3-(4-Fluorophenyl)-propylsulfanyl]-N-(pyridin-2-yl-methyl)-pyridine-3-carboxylic acid amide

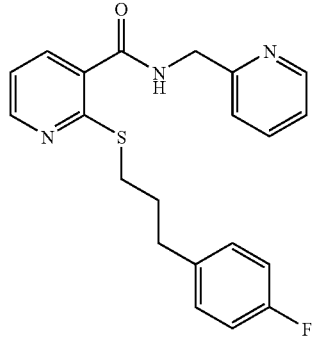

a) Synthesis of 2-(3-(4-fluorophenyl)propylthio)nicotinic acid 2-(3-(4-Fluorophenyl)propylthio)nicotinic acid was prepared according to the process described in exemplary compound 169 section a).

b) Synthesis of 2-[3-(4-fluorophenyl)-propylsulfanyl]-N-(pyridin-2-yl-methyl)-pyridine-3-carboxylic acid amide 520 mg (2.74 mmol) of EDC hydrochloride, 250 mg (1.64 mmol) of HOBT, 0.9 ml (5.48 mmol) of DIPEA and 180 mg (1.64 mmol) of pyridin-2-yl-methanamine were added in succession to a solution of 400 mg (1.37 mmol) of 2-(3-(4-fluorophenyl)-propylthio)nicotinic acid in DCM (6 ml), and the mixture was stirred for 4 h at RT. Dilution with water (40 ml) and extraction with DCM (3×50 ml) were then carried out. The combined organic phases were washed with a sat. NH$_4$Cl sol. and water, dried over Na$_2$SO$_4$, filtered and concentrated in vacuo. CC (hexane/EA 22:3) of the residue yielded 240 mg (0.63 mmol, 46%) of 2-[3-(4-fluorophenyl)-propylsulfanyl]-N-(pyridin-2-yl-methyl)-pyridine-3-carboxylic acid amide. MS: m/z 382.1 [M+H]$^+$.

Synthesis of exemplary compound 147: 2-[3-(4-Fluorophenyl)-propylsulfanyl]-4-methyl-N-(thiophen-2-yl-methyl)-pyridine-3-carboxylic acid amide

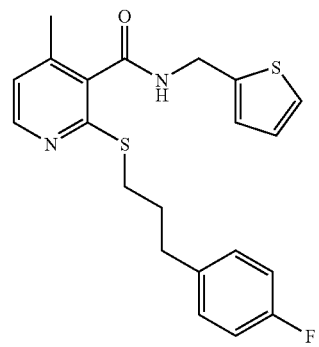

a) Synthesis of 2-(3-(4-fluorophenyl)propylthio)-4-methylnicotinenitrile 4.14 g (30 mmol) of K$_2$CO$_3$ and 5.2 g (30 mmol) of 1-(3-chloropropyl)-4-fluoro-benzene were added to a solution of 3.0 g (20 mmol) of 2-mercapto-4-methyl-nicotinenitrile in acetone (60 ml), and the mixture was then heated for 16 h at 60° C. Filtration over kieselguhr was then carried out and the filtrate was diluted with water (50 ml). Washing with EA (200 ml) was then carried out. The aqueous phase was acidified with 6M hydrochloric acid (50 ml) and then extracted with EA (3×100 ml). The combined organic phases were washed with water and brine, dried over Na$_2$SO$_4$, filtered and concentrated in vacuo. CC (hexane/EA 9:1) of the residue yielded 3.5 g (12 mmol, 61%) of 2-(3-(4-fluorophenyl)propylthio)-4-methylnicotine-nitrile.

b) Synthesis of 2-(3-(4-fluorophenyl)propylthio)-4-methylnicotinic acid

50% sulfuric acid (8 ml) was added to 500 mg (1.74 mmol) of 2-(3-(4-fluorophenyl)-propylthio) -4-methylnicotinenitrile, and the reaction solution was heated for 6 d at 140° C. The mixture was then poured onto ice-water and extracted with EA (3×100 ml). The combined organic phases were washed with water and brine, dried over Na$_2$SO$_4$, filtered and concentrated in vacuo. There were obtained as residue 400 mg (1.31 mmol, 75%) of 2-(3-(4-fluorophenyl)propylthio)-4-methylnicotinic acid, which was reacted further without additional purification.

c) Synthesis of 2-[3-(4-fluorophenyl)-propylsulfanyl]-4-methyl-N-(thiophen-2-yl-methyl)-pyridine-3-carboxylic acid amide From 200 mg (0.66 mmol) of 2-(3-(4-fluorophenyl)propylthio)-4-methylnicotinic acid and 80 µl (0.79 mmol) of thiophen-2-yl-methanamine there were prepared, according to the process described for exemplary compound 169 section b), 120 mg (0.30 mmol, 45%) of 2-[3-(4-fluorophenyl)-propylsulfanyl]-4-methyl-N-(thiophen-2-yl-methyl)-pyridine-3-carboxylic acid amide. MS: m/z 401.1 [M+H]$^+$.

Synthesis of exemplary compound 167: N-(3,3-Dimethyl-butyl)-2-[(2-oxo-3-phenyl-propyl)sulfanyl]-pyridine-3-carboxylic acid amide

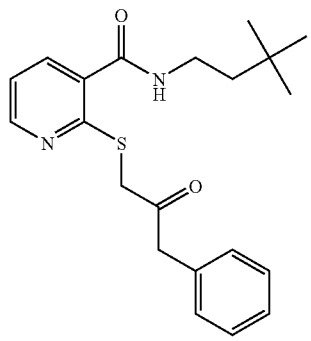

a) Synthesis of N-(3,3-dimethylbutyl)-2-mercapto-nicotinamide 5.84 ml (33.8 mmol) of DIPEA and 4.66 g (14.5 mmol) of TBTU were added at 0° C. to a solution of 1.50 g (9.7 mmol) of 2-mercapto-nicotinic acid in DMF (30 ml). After stirring for 30 min at 0° C., 1.6 ml (11.6 mmol) of 3,3-dimethylbutan-1-amine were added and then the mixture was stirred for 16 h at RT. Dilution with water (100 ml) and extraction with EA (2×100 ml) were then carried out. The combined organic phases were washed with water and brine, dried over Na$_2$SO$_4$, filtered and concentrated in vacuo. CC (hexane/acetone 1:1) of the residue yielded 1.4 g (5.9 mmol, 61%) of N-(3,3-dimethylbutyl)-2-mercapto-nicotinamide.

b) Synthesis of N-(3,3-dimethyl-butyl)-2-[(2-oxo-3-phenyl-propyl)sulfanyl]-pyridine-3-carboxylic acid 840 mg (6.1 mmol) of K$_2$CO$_3$ and 340 mg (2.0 mmol) of 1-chloro-3-phenylpropan-2-one were added to a solution of 450 mg (2.0 mmol) of N-(3,3-dimethylbutyl)-2-mercapto-nicotinamide in acetone (10 ml), and the mixture was then heated for 1 h at 50° C. Dilution with water (20 ml) and extraction with EA (2×30 ml) were then carried out. The combined organic phases were washed with water and brine, dried over Na$_2$SO$_4$, filtered and concentrated in vacuo. CC (hexane/EA 4:1) of the residue yielded 420 mg (1.1 mmol, 56%) of N-(3,3-dimethyl-butyl)-2-[(2-oxo-3-phenyl-propyl)sulfanyl]-pyridine-3-carboxylic acid amide. MS: m/z 371.2 [M+H]$^+$.

Synthesis of exemplary compound 169: 2-[[3,3-Difluoro-3-(4-fluorophenyl)-propyl]sulfanyl]-N-(3-methyl-butyl)-pyridine-3-carboxylic acid amide

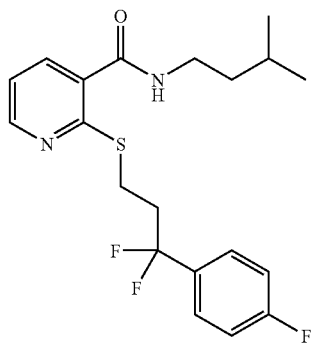

a) Synthesis of 2-(3,3-difluoro-3-(4-fluorophenyl)propylthio)nicotinic acid 1.02 g (4.0 mmol) of 1-(3-bromo-1,1-difluoropropyl)-4-fluorobenzene (precursor VC005) and 1.67 g (12.0 mmol) of K$_2$CO$_3$ were added to a solution of 620 mg (4.0 mmol) of 2-mercapto-nicotinic acid in DMF (10 ml), and the mixture was heated for 2 h at 90° C. Dilution with water (20 ml) was then carried out, and the pH was adjusted to ~2 with 6M hydrochloric acid. Extraction with EA (3×40 ml) was then carried out. The combined organic phases were washed with water and brine, dried over Na$_2$SO$_4$, filtered and concentrated in vacuo. CC (hexane/EA 1:4) of the residue yielded 400 mg (1.2 mmol, 31%) of 2-(3,3-difluoro-3-(4-fluorophenyl)propylthio)-nicotinic acid.

b) Synthesis of 2-[[3,3-difluoro-3-(4-fluorophenyl)-propyl]sulfanyl]-N-(3-methyl-butyl)-pyridine-3-carboxylic acid amide 320 µl (1.83 mmol) of DIPEA and 350 mg (0.91 mmol) of HATU were added at 0° C. to a solution of 150 mg (0.46 mmol) of 2-(3,3-difluoro-3-(4-fluorophenyl)propylthio)-nicotinic acid in DCM (10 ml). After stirring for 30 min at 0° C., 63 µl (0.55 mmol) of 3-methylbutan-1-amine were added and then the mixture was stirred for 16 h at RT. Dilution with water (20 ml) and extraction with DCM (2×20 ml) were then carried out. The combined organic phases were washed with water and brine, dried over Na$_2$SO$_4$, filtered and concentrated in vacuo. CC (EA/hexane 7:3) of the residue yielded 100 mg (0.25 mmol, 55%) of 2-[[3,3-difluoro-3-(4-fluorophenyl)-propyl]-sulfanyl]-N-(3-methyl-butyl)-pyridine-3-carboxylic acid amide. MS: m/z 397.1 [m+H]$^+$.

Synthesis of exemplary compound 225: 6-Fluoro-2-(3-phenylpropylthio) -N-(thiophen-2-ylmethyl)pyridine-3-carboxylic acid amide

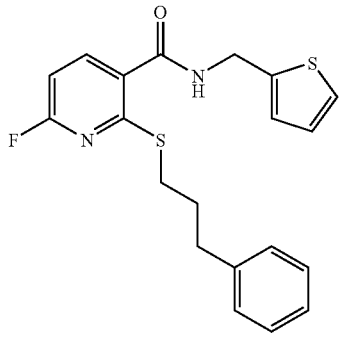

a) Synthesis of 2,6-difluoro-N-(thiophen-2-ylmethyl)nicotinamide 795 mg (5.0 mmol) of 2,6-difluoro-nicotinic acid were dissolved in thionyl chloride (15 ml) and the solution was heated for 2 h at 80° C. Concentration in vacuo was then carried out and the residue was taken up in dioxane (15 ml). 566 mg (5.0 mmol) of thiophen-2-yl-methanamine were then added and the mixture was stirred for 1 h at RT. Concentration in vacuo was then carried out and the residue was taken up in EA, washed with water, a sat. aq. $Na_2CO_3$ sol., water again and brine, dried over $Na_2SO_4$, filtered and concentrated in vacuo. CC (hexane/EA 7:3) of the residue yielded 605 mg (2.4 mmol, 48%) of 2,6-difluoro-N-(thiophen-2-ylmethyl) nicotinamide.

b) Synthesis of 6-fluoro-2-(3-phenylpropylthio)-N-(thiophen-2-ylmethyl)pyridine-3-carboxylic acid amide 919 mg (6.0 mmol) of $K_2CO_3$ and 305 mg (2.0 mmol) of 3-phenylpropane-1-thiol were added to a solution of 509 mg (2.0 mmol) of 2,6-difluoro-N-(thiophen-2-ylmethyl)-nicotinamide in DMF (10 ml), and the mixture was stirred for 1 h at RT. Dilution with water and extraction with EA were then carried out. The organic phase was washed with water and brine, dried over $Na_2SO_4$, filtered and concentrated in vacuo. CC (hexane/EA 4:1) of the residue yielded 336 mg (0.9 mmol, 43%) of 6-fluoro-2-(3-phenylpropylthio)-N-(thiophen-2-ylmethyl)pyridine-3-carboxylic acid amide. MS: m/z 387.1 $[M+H]^+$.

Synthesis of Further Exemplary Compounds

The synthesis of further exemplary compounds was carried out according to the processes already described. Table 2 shows which compound was prepared by which process. It will be clear to the person skilled in the art which starting materials and reagents were used in each case.

TABLE 2

| Exemplary compound | Chemical name | Synthesis analogous to exemplary compound | MS m/z $[M + H]^+$ |
|---|---|---|---|
| 2 | 2-(3-Cyclohexyl-propylsulfanyl)-N-(thiophen-2-yl-methyl)-pyridine-3-carboxylic acid amide | 17 | 375.1 |
| 4 | N-(Thiophen-2-yl-methyl)-2-[2-[3-(trifluoromethyl)-phenoxy]-ethylsulfanyl]-pyridine-3-carboxylic acid amide | 17 | 439.1 |
| 5 | 2-(4-Methyl-pentylsulfanyl)-N-(thiophen-2-yl-methyl)-pyridine-3-carboxylic acid amide | 17 | 335.1 |
| 7 | 2-(4-Phenyl-butyl)-N-(thiophen-2-yl-methyl)-pyridine-3-carboxylic acid amide | 13 | 351.1 |
| 8 | 2-[3-(Benzenesulfonyl)-propyl]-N-(cyclohexyl-methyl)-pyridine-3-carboxylic acid amide | 13 | 401.2 |
| 9 | N-(Cyclohexyl-methyl)-2-(4-phenyl-butyl)-pyridine-3-carboxylic acid amide | 13 | 351.2 |
| 10 | 2-[3-(Benzenesulfonyl)-propyl]-N-(thiophen-2-yl-methyl)-pyridine-3-carboxylic acid amide | 13 | 401.1 |
| 12 | N-(Thiophen-2-yl-methyl)-2-[3-[[3-(trifluoromethyl)phenyl]sulfonyl]-propyl]-pyridine-3-carboxylic acid amide | 13 | 469.1 |
| 18 | N-(Thiophen-2-yl-methyl)-2-[3-[3-(trifluoromethyl)phenyl]-propylsulfanyl]-pyridine-3-carboxylic acid amide | 17 | 437.1 |
| 19 | 2-[2-[(4-Fluorophenyl)sulfanyl]-propylsulfanyl]-N-(thiophen-2-yl-methyl)-pyridine-3-carboxylic acid amide | 16 (aus VC002) | 419.1 |
| 20 | N-(Thiophen-2-yl-methyl)-2-[2-[[3-(trifluoromethyl)phenyl]sulfanyl]-propylsulfanyl]-pyridine-3-carboxylic acid amide | 16 (aus VC003) | 469.1 |
| 22 | 2-[4-(4-Fluorophenyl)-butyl]-N-(thiophen-2-yl-methyl)-pyridine-3-carboxylic acid amide | 21 | 369.1 |
| 23 | 2-(3-Phenylsulfanyl-propyl)-N-(thiophen-2-yl-methyl)-pyridine-3-carboxylic acid amide | 21 | 369.1 |
| 24 | 2-[(1-Methyl-2-phenylsulfanyl-ethyl)sulfanyl]-N-(thiophen-2-yl-methyl)-pyridine-3-carboxylic acid amide | 16 (aus VC004) | 401.1 |
| 25 | N-(Cycloheptyl-methyl)-2-[4-[3-(trifluoromethyl)phenyl]-butyl]-pyridine-3-carboxylic acid amide | 17 | 433.2 |
| 26 | N-(5-Bicyclo[2.2.1]heptanyl-methyl)-2-[4-[3-(trifluoromethyl)phenyl]-butyl]-pyridine-3-carboxylic acid amide | 17 | 431.2 |
| 27 | N-(5-Bicyclo[2.2.1]heptanyl-methyl)-2-[3-[3-(trifluoromethyl)phenyl]-propylsulfanyl]-pyridine-3-carboxylic acid amide | 51 | 449.2 |
| 28 | N-(5-Bicyclo[2.2.1]heptanyl-methyl)-2-(4-methyl-pentylsulfanyl)-pyridine-3-carboxylic acid amide | 51 | 347.2 |
| 29 | N-(Cycloheptyl-methyl)-2-[3-[(4-fluorophenyl)sulfanyl]-propyl]-pyridine-3-carboxylic acid amide | 21 | 401.2 |
| 30 | N-(5-Bicyclo[2.2.1]heptanyl-methyl)-2-[3-[(4-fluorophenyl)sulfanyl]-propyl]-pyridine-3-carboxylic acid amide | 21 | 399.2 |
| 31 | N-(Cycloheptyl-methyl)-2-[3-[[3-(trifluoromethyl)phenyl]sulfonyl]-propyl]-pyridine-3-carboxylic acid amide | 21 | 483.2 |
| 32 | N-(5-Bicyclo[2.2.1]heptanyl-methyl)-2-[3-[[3-(trifluoromethyl)phenyl]sulfonyl]-propyl]-pyridine-3-carboxylic acid amide | 21 | 481.2 |
| 33 | N-(5-Bicyclo[2.2.1]heptanyl-methyl)-2-(3-phenyl-propylsulfanyl)-pyridine-3-carboxylic acid amide | 51 | 381.2 |
| 34 | N-(5-Bicyclo[2.2.1]heptanyl-methyl)-2-[3-[4-(trifluoromethyl)-phenyl]-propylsulfanyl-pyridine-3-carboxylic acid amide | 51 | 449.2 |

TABLE 2-continued

| Exemplary compound | Chemical name | Synthesis analogous to exemplary compound | MS m/z [M + H]+ |
|---|---|---|---|
| 35 | N-(5-Bicyclo[2.2.1]heptanyl-methyl)-2-[3-(4-chlorophenyl)-propylsulfanyl]-pyridine-3-carboxylic acid amide | 51 | 415.2 |
| 36 | N-[(3,5-Difluoro-phenyl)-methyl]-2-[3-(4-fluorophenyl)-propylsulfanyl]-pyridine-3-carboxylic acid amide | 42 | 417.1 |
| 37 | N-[(5-Chloro-thiophen-2-yl)-methyl]-2-[3-(4-fluorophenyl)-propylsulfanyl]-pyridine-3-carboxylic acid amide | 42 | 421.1 |
| 38 | N-[(2,2-Dimethyl-cyclopropyl)-methyl]-2-[3-(4-fluorophenyl)-propylsulfanyl]-pyridine-3-carboxylic acid amide | 42 | 373.2 |
| 39 | N-(5-Bicyclo[2.2.1]heptanyl-methyl)-2-[3-(3-fluorophenyl)-propylsulfanyl]-pyridine-3-carboxylic acid amide | 51 | 399.2 |
| 40 | N-(Cyclohexyl-methyl)-2-[3-(4-fluorophenyl)-propylsulfanyl]-pyridine-3-carboxylic acid amide | 42 | 387.2 |
| 41 | N-(Cycloheptyl-methyl)-2-[3-(4-fluorophenyl)-propylsulfanyl]-pyridine-3-carboxylic acid amide | 42 | 401.2 |
| 43 | N-(5-Bicyclo[2.2.1]heptanyl-methyl)-2-[[3-(4-fluorophenyl)-3-oxo-propyl]sulfanyl]-pyridine-3-carboxylic acid amide | 51 | 413.2 |
| 44 | N-(5-Bicyclo[2.2.1]heptanyl-methyl)-2-[(3-oxo-3-phenyl-propyl)sulfanyl]-pyridine-3-carboxylic acid amide | 51 | 395.2 |
| 45 | N-(5-Bicyclo[2.2.1]heptanyl-methyl)-2-(hexylsulfanyl)-pyridine-3-carboxylic acid amide | 51 | 347.2 |
| 46 | N-(5-Bicyclo[2.2.1]heptanyl-methyl)-2-(2-phenoxy-ethylsulfanyl)-pyridine-3-carboxylic acid amide | 51 | 383.2 |
| 47 | N-(5-Bicyclo[2.2.1]heptanyl-methyl)-2-[2-[3-(trifluoromethyl)-phenoxy]-ethylsulfanyl]-pyridine-3-carboxylic acid amide | 51 | 451.2 |
| 48 | 2-[3-(4-Fluorophenyl)-propylsulfanyl]-N-(3,3,3-trifluoro-propyl)-pyridine-3-carboxylic acid amide | 51 | 387.1 |
| 49 | N-(5-Bicyclo[2.2.1]heptanyl-methyl)-2-[2-(4-fluoro-phenoxy)-ethylsulfanyl]-pyridine-3-carboxylic acid amide | 51 | 401.2 |
| 52 | N-(5-Bicyclo[2.2.1]heptanyl-methyl)-2-(3-naphthalen-1-yl-propylsulfanyl)-pyridine-3-carboxylic acid amide | 51 | 431.2 |
| 53 | N-(5-Bicyclo[2.2.1]heptanyl-methyl)-2-[3-[3-fluoro-4-(trifluoromethyl)-phenyl]-propylsulfanyl]-pyridine-3-carboxylic acid amide | 51 | 467.2 |
| 54 | N-(5-Bicyclo[2.2.1]heptanyl-methyl)-2-[3-[4-fluoro-3-(trifluoromethyl)-phenyl]-propylsulfanyl]-pyridine-3-carboxylic acid amide | 51 | 467.2 |
| 55 | N-(Cyclooctyl-methyl)-2-[3-(4-fluorophenyl)-propylsulfanyl]-pyridine-3-carboxylic acid amide | 42 | 415.2 |
| 56 | N-(5-Bicyclo[2.2.1]heptanyl-methyl)-2-[3-(4-methoxyphenyl)-propylsulfanyl]-pyridine-3-carboxylic acid amide | 51 | 411.2 |
| 57 | 2-[3-(4-Fluorophenyl)-propylsulfanyl]-N-[(4-methoxyphenyl)-methyl]-pyridine-3-carboxylic acid amide | 42 | 411.1 |
| 59 | 2-[3-(4-Fluorophenyl)-propylsulfanyl]-N-[[3-(trifluoromethyl)phenyl]-methyl]-pyridine-3-carboxylic acid amide | 42 | 449.1 |
| 60 | N-(5-Bicyclo[2.2.1]heptanyl-methyl)-2-[3-(3,4-difluoro-phenyl)-propylsulfanyl]-pyridine-3-carboxylic acid amide | 51 | 417.2 |
| 61 | N-(5-Bicyclo[2.2.1]heptanyl-methyl)-2-[3-(3,5-difluoro-phenyl)-propylsulfanyl]-pyridine-3-carboxylic acid amide | 51 | 417.2 |
| 62 | N-(5-Bicyclo[2.2.1]heptanyl-methyl)-2-[3-(2,4-difluoro-phenyl)-propylsulfanyl]-pyridine-3-carboxylic acid amide | 51 | 417.2 |
| 63 | N-[(2-Fluorophenyl)-methyl]-2-[3-(4-fluorophenyl)-propylsulfanyl]-pyridine-3-carboxylic acid amide | 42 | 399.1 |
| 64 | N-[(3-Fluorophenyl)-methyl]-2-[3-(4-fluorophenyl)-propylsulfanyl]-pyridine-3-carboxylic acid amide | 42 | 399.1 |
| 65 | N-[(4-Fluorophenyl)-methyl]-2-[3-(4-fluorophenyl)-propylsulfanyl]-pyridine-3-carboxylic acid amide | 42 | 399.1 |
| 66 | N-Benzyl-2-[3-(4-fluorophenyl)-propylsulfanyl]-pyridine-3-carboxylic acid amide | 42 | 381.1 |
| 67 | N-(5-Bicyclo[2.2.1]heptanyl-methyl)-2-[(1-methyl-3-phenyl-propyl)sulfanyl]-pyridine-3-carboxylic acid amide | 51 | 395.2 |
| 68 | N-(5-Bicyclo[2.2.1]heptanyl-methyl)-2-[3-(3,4,5-trifluoro-phenyl)-propylsulfanyl]-pyridine-3-carboxylic acid amide | 51 | 435.2 |
| 69 | N-(5-Bicyclo[2.2.1]heptanyl-methyl)-2-[3-[3-fluoro-5-(trifluoromethyl)-phenyl]-propylsulfanyl]-pyridine-3-carboxylic acid amide | 51 | 467.2 |
| 70 | N-(5-Bicyclo[2.2.1]heptanyl-methyl)-2-[3-(3-methoxyphenyl)-propylsulfanyl]-pyridine-3-carboxylic acid amide | 51 | 411.2 |
| 71 | N-[(3,4-Difluoro-phenyl)-methyl]-2-[3-(4-fluorophenyl)-propylsulfanyl]-pyridine-3-carboxylic acid amide | 42 | 417.1 |
| 72 | N-(2,3-Dihydro-benzofuran-5-yl-methyl)-2-[3-(4-fluorophenyl)-propylsulfanyl]-pyridine-3-carboxylic acid amide | 42 | 423.1 |
| 73 | N-(5-Bicyclo[2.2.1]heptanyl-methyl)-2-[3-(3-hydroxyphenyl)-propylsulfanyl]-pyridine-3-carboxylic acid amide | 58 | 397.2 |
| 74 | N-(5-Bicyclo[2.2.1]heptanyl-methyl)-2-[[3-(4-fluorophenyl)-1-methyl-propyl]sulfanyl]-pyridine-3-carboxylic acid amide | 51 | 413.2 |
| 75 | N-(5-Bicyclo[2.2.1]heptanyl-methyl)-2-[[3-(4-fluorophenyl)-2-methyl-propyl]sulfanyl]-pyridine-3-carboxylic acid amide | 51 | 413.2 |
| 76 | 2-[3-(4-Fluorophenyl)-propylsulfanyl]-N-[(2-methoxyphenyl)-methyl]-pyridine-3-carboxylic acid amide | 42 | 411.1 |
| 77 | 2-[3-(4-Fluorophenyl)-propylsulfanyl]-N-[(3-methoxyphenyl)-methyl]-pyridine-3-carboxylic acid amide | 42 | 411.1 |
| 78 | 2-[3-(4-Fluorophenyl)-propylsulfanyl]-N-phenethyl-pyridine-3-carboxylic acid amide | 42 | 395.2 |
| 79 | 2-[3-(4-Fluorophenyl)-propylsulfanyl]-N-[[4-(trifluoromethyloxy)-phenyl]-methyl]-pyridine-3-carboxylic acid amide | 42 | 465.1 |
| 80 | 2-[3-(4-Fluorophenyl)-propylsulfanyl]-N-[[4-(trifluoromethyl)-phenyl]-methyl]-pyridine-3-carboxylic acid amide | 42 | 449.1 |
| 81 | 2-[3-(4-Fluorophenyl)-propylsulfanyl]-N-(2-pyridine-3-yl-ethyl)-pyridine-3-carboxylic acid amide | 42 | 396.1 |
| 82 | 2-[3-(4-Fluorophenyl)-propylsulfanyl]-N-(2-pyridine-2-yl-ethyl)-pyridine-3-carboxylic acid amide | 42 | 396.1 |
| 83 | 2-[3-(4-Fluorophenyl)-propylsulfanyl]-N-[(2-hydroxyphenyl)-methyl]-pyridine-3-carboxylic acid amide | 58 | 397.1 |
| 84 | 2-[3-(4-Fluorophenyl)-propylsulfanyl]-N-[(3-hydroxyphenyl)-methyl]-pyridine-3-carboxylic acid amide | 58 | 397.1 |

TABLE 2-continued

| Exemplary compound | Chemical name | Synthesis analogous to exemplary compound | MS m/z [M + H]+ |
|---|---|---|---|
| 85 | 2-[3-(4-Fluorophenyl)-propylsulfanyl]-N-[2-(m-tolyl)-ethyl]-pyridine-3-carboxylic acid amide | 42 | 409.2 |
| 86 | 2-[3-(4-Fluorophenyl)-propylsulfanyl]-N-[2-(o-tolyl)-ethyl]-pyridine-3-carboxylic acid amide | 42 | 409.2 |
| 87 | 2-[3-(4-Fluorophenyl)-propylsulfanyl]-N-[[3-(trifluoromethyloxy)-phenyl]-methyl]-pyridine-3-carboxylic acid amide | 42 | 465.1 |
| 88 | 2-[3-(4-Fluorophenyl)-propylsulfanyl]-N-[(4-hydroxyphenyl)-methyl]-pyridine-3-carboxylic acid amide | 42 | 397.1 |
| 89 | 2-[3-(4-Fluorophenyl)-propylsulfanyl]-N-(2-pyridine-4-yl-ethyl)-pyridine-3-carboxylic acid amide | 42 | 396.1 |
| 90 | 2-[3-(4-Fluorophenyl)-propylsulfanyl]-N-[2-(p-tolyl)-ethyl]-pyridine-3-carboxylic acid amide | 42 | 409.2 |
| 91 | N-(5-Bicyclo[2.2.1]heptanyl-methyl)-2-[3-(4-fluorophenyl)-butylsulfanyl]-pyridine-3-carboxylic acid amide | 51 | 413.2 |
| 92 | N-(5-Bicyclo[2.2.1]heptanyl-methyl)-2-[3-(2,4,5-trifluoro-phenyl)-propylsulfanyl]-pyridine-3-carboxylic acid amide | 51 | 435.2 |
| 93 | 2-[3-(4-Fluorophenyl)-propylsulfanyl]-N-(3-pyridine-2-yl-propyl)-pyridine-3-carboxylic acid amide | 42 | 410.2 |
| 94 | 2-[3-(4-Fluorophenyl)-propylsulfanyl]-N-(3-pyridine-3-yl-propyl)-pyridine-3-carboxylic acid amide | 42 | 410.2 |
| 95 | 2-[3-(4-Fluorophenyl)-propylsulfanyl]-N-(3-pyridine-4-yl-propyl)-pyridine-3-carboxylic acid amide | 42 | 410.2 |
| 96 | 2-[3-(4-Fluorophenyl)-propylsulfanyl]-N-propyl-pyridine-3-carboxylic acid amide | 42 | 333.1 |
| 97 | N-Butyl-2-[3-(4-fluorophenyl)-propylsulfanyl]-pyridine-3-carboxylic acid amide | 42 | 347.2 |
| 98 | 2-(3-Pyridin-3-yl-propylsulfanyl)-N-(thiophen-2-yl-methyl)-pyridine-3-carboxylic acid amide | 167 | 370.1 |
| 99 | 2-[3-(p-Tolyl)-propylsulfanyl]-N-(thiophen-2-yl-methyl)-pyridine-3-carboxylic acid amide | 167 | 383.1 |
| 100 | 2-(4-Phenyl-butylsulfanyl)-N-(thiophen-2-yl-methyl)-pyridine-3-carboxylic acid amide | 51 | 383.1 |
| 101 | 2-(3-Pyridin-4-yl-propylsulfanyl)-N-(thiophen-2-yl-methyl)-pyridine-3-carboxylic acid amide | 51 | 370.1 |
| 102 | 2-(3-Naphthalen-2-yl-propylsulfanyl)-N-(thiophen-2-yl-methyl)-pyridine-3-carboxylic acid amide | 51 | 419.1 |
| 103 | 2-[3-(m-Tolyl)-propylsulfanyl]-N-(thiophen-2-yl-methyl)-pyridine-3-carboxylic acid amide | 167 | 383.1 |
| 104 | N-(Thiophen-2-yl-methyl)-2-(3-thiophen-2-yl-propylsulfanyl)-pyridine-3-carboxylic acid amide | 167 | 375.1 |
| 105 | 2-[(1-Methyl-3-phenyl-propyl)sulfanyl]-N-(thiophen-2-yl-methyl)-pyridine-3-carboxylic acid amide | 51 | 383.1 |
| 106 | N-(Thiophen-2-yl-methyl)-2-(3-thiophen-3-yl-propylsulfanyl)-pyridine-3-carboxylic acid amide | 167 | 375.1 |
| 107 | 2-[[1-Methyl-3-[3-(trifluoromethyl)phenyl]-propyl]sulfanyl]-N-(thiophen-2-yl-methyl)-pyridine-3-carboxylic acid amide | 167 | 451.1 |
| 108 | 2-[(2-Benzyl-cyclohexyl)sulfanyl]-N-(thiophen-2-yl-methyl)-pyridine-3-carboxylic acid amide | 115 | 423.1 |
| 109 | 2-[3-[3-Methyl-5-(trifluoromethyl)-phenyl]-propylsulfanyl]-N-(thiophen-2-yl-methyl)-pyridine-3-carboxylic acid amide | 115 | 451.1 |
| 110 | 2-[4-(3,4-Difluoro-phenyl)-butylsulfanyl]-N-(thiophen-2-yl-methyl)-pyridine-3-carboxylic acid amide | 115 | 419.1 |
| 111 | 2-(3-Pyridin-2-yl-propylsulfanyl)-N-(thiophen-2-yl-methyl)-pyridine-3-carboxylic acid amide | 225 | 370.1 |
| 113 | 2-[3-[4-Methyl-3-(trifluoromethyl)-phenyl]-propylsulfanyl]-N-(thiophen-2-yl-methyl)-pyridine-3-carboxylic acid amide | 115 | 451.1 |
| 114 | 2-[(3-Phenyl-cyclohexyl)sulfanyl]-N-(thiophen-2-yl-methyl)-pyridine-3-carboxylic acid amide | 115 | 409.1 |
| 116 | 2-[[3,3-Difluoro-3-(4-fluorophenyl)-propyl]sulfanyl]-N-(3,3-dimethyl-butyl)-pyridine-3-carboxylic acid amide | 115 | 411.2 |
| 117 | N-(Cycloheptyl-methyl)-2-[[3,3-difluoro-3-(4-fluorophenyl)-propyl]sulfanyl]-pyridine-3-carboxylic acid amide | 115 | 437.2 |
| 118 | 2-[[3,3-Difluoro-3-(4-fluorophenyl)-propyl]sulfanyl]-N-(thiophen-2-yl-methyl)-pyridine-3-carboxylic acid amide | 115 | 423.1 |
| 119 | 2-[3-(4-Fluorophenyl)-propylsulfanyl]-N-(1,2,3,4-tetrahydro-naphthalen-2-yl-methyl)-pyridine-3-carboxylic acid amide | 169 | 435.2 |
| 120 | N-(2,3-Dihydro-1H-inden-2-yl-methyl)-2-[3-(4-fluorophenyl)-propylsulfanyl]-pyridine-3-carboxylic acid amide | 169 | 421.2 |
| 121 | N-(1,3-Benzodioxol-5-yl-methyl)-2-[3-(4-fluorophenyl)-propylsulfanyl]-pyridine-3-carboxylic acid amide | 169 | 425.1 |
| 122 | 2-[3-(4-Fluorophenyl)-propylsulfanyl]-N-[(3-phenyl-phenyl)-methyl]-pyridine-3-carboxylic acid amide | 169 | 457.2 |
| 123 | 2-[3-(4-Fluorophenyl)-propylsulfanyl]-N-[(3-methyl-cyclohexyl)-methyl]-pyridine-3-carboxylic acid amide | 169 | 401.2 |
| 124 | 2-[[3,3-Difluoro-3-(4-fluorophenyl)-propyl]sulfanyl]-N-[(4-fluorophenyl)-methyl]-pyridine-3-carboxylic acid amide | 115 | 435.1 |
| 125 | N-(3,3-Dimethyl-2-oxo-butyl)-2-[3-(4-fluorophenyl)-propylsulfanyl]-pyridine-3-carboxylic acid amide | 169 | 389.2 |
| 127 | 2-[3-(4-Fluorophenyl)-propylsulfanyl]-N-(pyridin-3-yl-methyl)-pyridine-3-carboxylic acid amide | 169 | 382.1 |
| 128 | 2-[3-(4-Fluorophenyl)-propylsulfanyl]-N-(pyridin-4-yl-methyl)-pyridine-3-carboxylic acid amide | 169 | 382.1 |
| 129 | 3-[[[2-[3-(4-Fluorophenyl)-propylsulfanyl]-pyridine-3-carbonyl]amino]-methyl]-benzoic acid methyl ester | 169 | 439.1 |
| 130 | 2-[3-(4-Fluorophenyl)-propylsulfanyl]-N-[3-(2-methoxyphenyl)-propyl]-pyridine-3-carboxylic acid amide | 169 | 439.2 |
| 132 | N-[(4-Fluorophenyl)-methyl]-2-[[1-methyl-3-[3-(trifluoromethyl)phenyl]-propyl]sulfanyl]-pyridine-3-carboxylic acid amide | 51 | 463.1 |
| 133 | 2-[3-(4-Fluorophenyl)-propylsulfanyl]-N-(3-methyl-butyl)-pyridine-3-carboxylic acid amide | 169 | 361.2 |
| 134 | 2-[3-(4-Fluorophenyl)-propylsulfanyl]-N-(tetrahydro-pyran-2-yl-methyl)-pyridine-3-carboxylic acid amide | 169 | 389.2 |
| 135 | 2-[3-(4-Fluorophenyl)-propylsulfanyl]-N-[3-(1H-pyrazol-1-yl)-propyl]-pyridine-3-carboxylic acid amide | 169 | 399.2 |
| 136 | 2-[3-(4-Fluorophenyl)-propylsulfanyl]-N-(naphthalen-2-yl-methyl)-pyridine-3-carboxylic acid amide | 169 | 431.2 |
| 137 | N-(2,3-Dihydro-[1,4]benzodioxin-6-yl-methyl)-2-[3-(4-fluorophenyl)-propylsulfanyl]-pyridine-3-carboxylic acid amide | 169 | 439.1 |

TABLE 2-continued

| Exemplary compound | Chemical name | Synthesis analogous to exemplary compound | MS m/z [M + H]+ |
|---|---|---|---|
| 138 | 2-[3-(4-Fluorophenyl)-propylsulfanyl]-N-[(3-morpholin-4-yl-phenyl)-methyl]-pyridine-3-carboxylic acid amide | 169 | 466.2 |
| 139 | N-(2,3-Dihydro-benzofuran-6-yl-methyl)-2-[3-(4-fluorophenyl)-propylsulfanyl]-pyridine-3-carboxylic acid amide | 169 | 423.1 |
| 140 | 2-[3-(4-Fluorophenyl)-propylsulfanyl]-N-[[3-(1H-pyrazol-1-yl)-phenyl]-methyl]-pyridine-3-carboxylic acid amide | 169 | 447.2 |
| 141 | 2-[3-(4-Fluorophenyl)-propylsulfanyl]-N-[3-(1H-[1,2,3]triazol-1-yl)-propyl]-pyridine-3-carboxylic acid amide | 169 | 400.2 |
| 142 | N-(7-Bicyclo[2.2.1]heptanyl-methyl)-2-[3-(4-fluorophenyl)-propylsulfanyl]-pyridine-3-carboxylic acid amide | 169 | 399.2 |
| 144 | 2-[3-(4-Fluorophenyl)-propylsulfanyl]-N-(thiazol-2-yl-methyl)-pyridine-3-carboxylic acid amide | 143 | 388.1 |
| 145 | 2-[3-(4-Fluorophenyl)-propylsulfanyl]-N-(thiazol-5-yl-methyl)-pyridine-3-carboxylic acid amide | 143 | 388.1 |
| 146 | 2-[3-(4-Fluorophenyl)-propylsulfanyl]-N-(oxazol-2-yl-methyl)-pyridine-3-carboxylic acid amide | 143 | 372.1 |
| 148 | N-(3,3-Dimethyl-butyl)-2-[3-(4-fluorophenyl)-propylsulfanyl]-4-methyl-pyridine-3-carboxylic acid amide | 147 | 389.2 |
| 149 | N-(3,3-Dimethyl-butyl)-2-[[1-methyl-3-[3-(trifluoromethyl)phenyl]-propyl]sulfanyl]-pyridine-3-carboxylic acid amide | 115 | 439.2 |
| 150 | 2-[3-(4-Fluorophenyl)-propylsulfanyl]-N-(quinolin-7-yl-methyl)-pyridine-3-carboxylic acid amide | 143 | 432.1 |
| 151 | 2-[3-(4-Fluorophenyl)-propylsulfanyl]-N-[(3-pyridin-2-yl-phenyl)-methyl]-pyridine-3-carboxylic acid amide | 143 | 458.2 |
| 152 | 2-[3-(4-Fluorophenyl)-propylsulfanyl]-N-[(3-pyridin-3-yl-phenyl)-methyl]-pyridine-3-carboxylic acid amide | 143 | 458.2 |
| 153 | N-(3,3-Dimethyl-butyl)-2-[[(1R)-1-methyl-3-phenyl-propyl]sulfanyl]-pyridine-3-carboxylic acid amide | 115 | 371.2 |
| 154 | N-(3,3-Dimethyl-butyl)-2-[[(1S)-1-methyl-3-phenyl-propyl]sulfanyl]-pyridine-3-carboxylic acid amide | 115 | 371.2 |
| 155 | 2-[(2-Benzyl-cyclopentyl)sulfanyl]-N-(3,3-dimethyl-butyl)-pyridine-3-carboxylic acid amide | 115 | 397.2 |
| 156 | N-(7-Bicyclo[2.2.1]heptanyl-methyl)-2-[3-[3-(trifluoromethyl)phenyl]-propylsulfanyl]-pyridine-3-carboxylic acid amide | 169 | 449.2 |
| 157 | 2-[3-(4-Fluorophenyl)-propylsulfanyl]-N-[3-(1H-[1,2,4]triazol-1-yl)-propyl]-pyridine-3-carboxylic acid amide | 143 | 400.2 |
| 158 | 2-[3-(4-Fluorophenyl)-propylsulfanyl]-N-([1,3,4]oxadiazol-2-yl-methyl)-pyridine-3-carboxylic acid amide | 143 | 373.1 |
| 159 | 2-[3-(4-Fluorophenyl)-propylsulfanyl]-N-[(3-pyridin-4-yl-phenyl)-methyl]-pyridine-3-carboxylic acid amide | 143 | 458.2 |
| 160 | N-[[4-(Cyclopropyl-methyl)-3,4-dihydro-2H-[1,4]benzoxazin-6-yl]-methyl]-2-[3-(4-fluorophenyl)-propylsulfanyl]-pyridine-3-carboxylic acid amide | 169 | 492.2 |
| 161 | N-[(4-Ethyl-3,4-dihydro-2H-[1,4]benzoxazin-6-yl]-methyl]-2-[3-(4-fluorophenyl)-propylsulfanyl]-pyridine-3-carboxylic acid amide | 169 | 466.2 |
| 162 | 2-[3-(4-Fluorophenyl)-propylsulfanyl]-N-[(4-methyl-3,4-dihydro-2H-[1,4]benzoxazin-6-yl]-methyl]-pyridine-3-carboxylic acid amide | 169 | 452.2 |
| 163 | 2-[3-(4-Fluorophenyl)-propylsulfanyl]-N-(3-methyl-3-phenyl-butyl)-pyridine-3-carboxylic acid amide | 169 | 437.2 |
| 164 | N-(7-Bicyclo[2.2.1]heptanyl-methyl)-2-[[3,3-difluoro-3-(4-fluorophenyl)-propyl]sulfanyl]-pyridine-3-carboxylic acid amide | 115 | 435.2 |
| 165 | 2-[[3,3-Difluoro-3-[3-(trifluoromethyl)phenyl]-propyl]sulfanyl]-N-[(4-fluorophenyl)-methyl]-pyridine-3-carboxylic acid amide | 115 | 485.1 |
| 166 | 2-[[3,3-Difluoro-3-[3-(trifluoromethyl)phenyl]-propyl]sulfanyl]-N-(3,3-dimethyl-butyl)-pyridine-3-carboxylic acid amide | 169 | 461.2 |
| 168 | 2-[[3,3-Difluoro-3-(4-fluorophenyl)-propyl]sulfanyl]-N-[(3-fluorophenyl)-methyl]-pyridine-3-carboxylic acid amide | 169 | 435.1 |
| 170 | N-Butyl-2-[[3,3-difluoro-3-(4-fluorophenyl)-propyl]sulfanyl]-pyridine-3-carboxylic acid amide | 169 | 383.1 |
| 171 | 2-[[3,3-Difluoro-3-(4-fluorophenyl)-propyl]sulfanyl]-N-(2-methoxy-ethyl)-pyridine-3-carboxylic acid amide | 169 | 385.1 |
| 172 | 2-[3-(4-Fluorophenyl)-propylsulfanyl]-N-(2-methoxy-ethyl)-pyridine-3-carboxylic acid amide | 169 | 349.1 |
| 173 | N-[(4-Fluoro-2-hydroxy-phenyl)-methyl]-2-[3-(4-fluorophenyl)-propylsulfanyl]-pyridine-3-carboxylic acid amide | 58 | 415.1 |
| 174 | 2-[3-(4-Fluorophenyl)-propylsulfanyl]-N-(furan-2-yl-methyl)-pyridine-3-carboxylic acid amide | 169 | 371.1 |
| 175 | 2-[3-(4-Fluorophenyl)-propylsulfanyl]-N-[(5-methyl-furan-2-yl)-methyl]-pyridine-3-carboxylic acid amide | 169 | 385.1 |
| 176 | N-[(4-Fluorophenyl)-methyl]-2-[[3-(4-fluorophenyl)-1-methyl-propyl]sulfanyl]-pyridine-3-carboxylic acid amide | 169 | 413.1 |
| 177 | 2-[[3-(4-Fluorophenyl)-1-methyl-propyl]sulfanyl]-N-(3-methyl-butyl)-pyridine-3-carboxylic acid amide | 169 | 375.2 |
| 178 | N-(7-Bicyclo[2.2.1]heptanyl-methyl)-2-[[3-(4-fluorophenyl)-1-methyl-propyl]sulfanyl]-pyridine-3-carboxylic acid amide | 169 | 413.2 |
| 179 | 2-[[3,3-Difluoro-3-(4-fluorophenyl)-propyl]sulfanyl]-N-(tetrahydro-furan-2-yl-methyl)-pyridine-3-carboxylic acid amide | 169 | 411.1 |
| 180 | 2-[[3,3-Difluoro-3-(4-fluorophenyl)-propyl]sulfanyl]-N-(tetrahydro-pyran-2-yl-methyl)-pyridine-3-carboxylic acid amide | 169 | 425.1 |
| 181 | 2-[3-(4-Fluorophenyl)-propylsulfanyl]-N-(tetrahydro-furan-2-yl-methyl)-pyridine-3-carboxylic acid amide | 169 | 375.1 |
| 182 | 2-[3-(4-Fluorophenyl)-propylsulfanyl]-N-(2-methoxy-3,3-dimethyl-butyl)-pyridine-3-carboxylic acid amide | 169 | 405.2 |
| 183 | 2-[[3,3-Difluoro-3-(4-fluorophenyl)-propyl]sulfanyl]-N-(m-tolyl-methyl)-pyridine-3-carboxylic acid amide | 169 | 431.1 |
| 184 | 2-[[3,3-Difluoro-3-(4-fluorophenyl)-propyl]sulfanyl]-N-[(3,5-dimethyl-phenyl)-methyl]-pyridine-3-carboxylic acid amide | 169 | 445.1 |
| 185 | 2-[[3,3-Difluoro-3-(4-fluorophenyl)-propyl]sulfanyl]-N-propyl-pyridine-3-carboxylic acid amide | 169 | 369.1 |
| 186 | 2-[[3,3-Difluoro-3-(4-fluorophenyl)-propyl]sulfanyl]-N-hexyl-pyridine-3-carboxylic acid amide | 169 | 411.2 |
| 187 | 2-[[3,3-Difluoro-3-(4-fluorophenyl)-propyl]sulfanyl]-N-(tetrahydro-furan-3-yl-methyl)-pyridine-3-carboxylic acid amide | 169 | 411.1 |

TABLE 2-continued

| Exemplary compound | Chemical name | Synthesis analogous to exemplary compound | MS m/z [M + H]+ |
|---|---|---|---|
| 188 | 2-[[3,3-Difluoro-3-(4-fluorophenyl)-propyl]sulfanyl]-N-(tetrahydro-pyran-3-yl-methyl)-pyridine-3-carboxylic acid amide | 169 | 425.1 |
| 189 | 2-[[3,3-Difluoro-3-(4-fluorophenyl)-propyl]sulfanyl]-N-(tetrahydro-pyran-4-yl-methyl)-pyridine-3-carboxylic acid amide | 169 | 425.1 |
| 190 | 2-[[3,3-Difluoro-3-(4-fluorophenyl)-propyl]sulfanyl]-N-(furan-2-yl-methyl)-pyridine-3-carboxylic acid amide | 169 | 407.1 |
| 191 | 2-[[3,3-Difluoro-3-(4-fluorophenyl)-propyl]sulfanyl]-N-[(5-methyl-furan-2-yl)-methyl]-pyridine-3-carboxylic acid amide | 169 | 421.1 |
| 192 | 2-[[3,3-Difluoro-3-(4-fluorophenyl)-propyl]sulfanyl]-N-pentyl-pyridine-3-carboxylic acid amide | 169 | 397.1 |
| 193 | 2-[[3,3-Difluoro-3-(4-fluorophenyl)-propyl]sulfanyl]-N-(3-methoxy-butyl)-pyridine-3-carboxylic acid amide | 169 | 413.1 |
| 194 | 2-[[3,3-Difluoro-3-(4-fluorophenyl)-propyl]sulfanyl]-N-(2-methoxy-propyl)-pyridine-3-carboxylic acid amide | 169 | 399.1 |
| 195 | 2-[[3,3-Difluoro-3-(4-fluorophenyl)-propyl]sulfanyl]-N-(2-methoxy-butyl)-pyridine-3-carboxylic acid amide | 169 | 413.1 |
| 196 | 3-[[2-[[3,3-Difluoro-3-(4-fluorophenyl)-propyl]sulfanyl]-pyridine-3-carbonyl]amino]-propionic acid methyl ester | 169 | 413.1 |
| 197 | 3-[[2-[[3,3-Difluoro-3-(4-fluorophenyl)-propyl]sulfanyl]-pyridine-3-carbonyl]amino]-propionic acid | 131 | 399.1 |
| 198 | 2-[[3,3-Difluoro-3-(4-fluorophenyl)-propyl]sulfanyl]-N-(2-dimethylaminoethyl)-pyridine-3-carboxylic acid amide | 169 | 398.1 |
| 199 | 2-[[3-(3,4-Difluoro-phenyl)-1-methyl-propyl]sulfanyl]-N-[(4-fluorophenyl)-methyl]-pyridine-3-carboxylic acid amide | 169 | 431.1 |
| 200 | 2-[[3-(3,4-Difluoro-phenyl)-1-methyl-propyl]sulfanyl]-N-(3-methyl-butyl)-pyridine-3-carboxylic acid amide | 169 | 393.2 |
| 201 | N-[(4-Fluorophenyl)-methyl]-2-[[3-(3-fluorophenyl)-1-methyl-propyl]sulfanyl]-pyridine-3-carboxylic acid amide | 169 | 413.1 |
| 202 | 2-[[3-(3-Fluorophenyl)-1-methyl-propyl]sulfanyl]-N-(3-methyl-butyl)-pyridine-3-carboxylic acid amide | 169 | 375.2 |
| 203 | N-(3-Methyl-butyl)-2-[[1-methyl-3-[3-(trifluoromethyl)phenyl]-propyl]sulfanyl]-pyridine-3-carboxylic acid amide | 169 | 425.2 |
| 204 | 2-[[3-(3,4-Difluoro-phenyl)-3,3-difluoro-propyl]sulfanyl]-N-[(4-fluorophenyl)-methyl]-pyridine-3-carboxylic acid amide | 169 | 453.1 |
| 205 | N-(1-Bicyclo[2.2.1]heptanyl-methyl)-2-[[3,3-difluoro-3-(4-fluorophenyl)-propyl]sulfanyl]-pyridine-3-carboxylic acid amide | 169 | 435.2 |
| 206 | N-(1-Bicyclo[2.2.1]heptanyl-methyl)-2-[3-(4-fluorophenyl)-propylsulfanyl]-pyridine-3-carboxylic acid amide | 169 | 399.2 |
| 207 | N-[(4-Fluorophenyl)-methyl]-2-[3-[3-(trifluoromethyl)phenyl]-propylsulfanyl]-pyridine-3-carboxylic acid amide | 169 | 449.1 |
| 208 | N-(3-Methyl-butyl)-2-[3-[3-(trifluoromethyl)phenyl]-propylsulfanyl]-pyridine-3-carboxylic acid amide | 169 | 411.2 |
| 209 | 2-[[3-(3,4-Difluoro-phenyl)-3,3-difluoro-propyl]sulfanyl]-N-(3-methyl-butyl)-pyridine-3-carboxylic acid amide | 169 | 415.1 |
| 210 | N-(7-Bicyclo[2.2.1]heptanyl-methyl)-2-[[3-(3,4-difluoro-phenyl)-3,3-difluoro-propyl]sulfanyl]-pyridine-3-carboxylic acid amide | 169 | 453.2 |
| 211 | 2-[[3,3-Difluoro-3-(4-fluorophenyl)-propyl]sulfanyl]-N-(2-hydroxy-ethyl)-pyridine-3-carboxylic acid amide | 169 | 371.1 |
| 224 | N-[(4-Fluoro-2-methoxy-phenyl)-methyl]-2-[3-(4-fluorophenyl)-propylsulfanyl]-pyridine-3-carboxylic acid amide | 169 | 429.1 |

Pharmacological Experiments

Fluorescence Assay Using a Voltage Sensitive Dye

Human CHO-$K_1$ cells expressing KCNQ2/3 channels are cultivated adherently at 37° C., 5% $CO_2$ and 95% humidity in cell culture bottles (e.g. 80 $cm^2$ TC flasks, Nunc) with DMEM-high glucose (Sigma Aldrich, D7777) including 10% FCS (PAN Biotech, e.g. 3302-P270521) or alternatively MEM Alpha Medium (1×, liquid, Invitrogen, #22571), 10% fetal calf serum (FCS) (Invitrogen, #10270-106, heat-inactivated) and the necessary selection antibiotics.

Before being sown out for the measurements, the cells are washed with a 1×DPBS buffer without $Ca^{2+}$/$Mg^{2+}$ (e.g. Invitrogen, #14190-094) and detached from the bottom of the culture vessel by means of Accutase (PAA Laboratories, #L11-007) (incubation with Accutase for 15 min at 37° C.). The cell count then present is determined using a CASY™ cell counter (TCC model, Schärfe System) in order subsequently to apply, depending on the density optimization for the individual cell line, 20,000-30,000 cells/well/100 ml of the described nutrient medium to 96-well measuring plates of the Corning™ CellBIND™ type (Flat Clear Bottom Black Polystyrene Microplates, #3340). Incubation is then carried out for one hour at room temperature, without gassing or adjusting the humidity, followed by incubation for 24 hours at 37° C., 5% $CO_2$ and 95% humidity.

The voltage-sensitive fluorescent dye from the Membrane Potential Assay Kit (Red™ Bulk format part R8123 for FLIPR, MDS Analytical Technologies™) is prepared by dissolving the contents of a vessel Membrane Potential Assay Kit Red Component A in 200 ml of extracellular buffer (ES buffer, 120 mM NaCl, 1 mM KCl, 10 mM HEPES, 2 mM $CaCl_2$, 2 mM $MgCl_2$, 10 mM glucose; pH 7.4). After removal of the nutrient medium, the cells are washed with 200 µl of ES buffer, then covered with a layer of 100 ml of the dye solution prepared above and incubated for 45 min at room temperature with the exclusion of light.

The fluorescence measurements are carried out with a BMG Labtech FLUOstar™ BMG Labtech NOVOstar™ or BMG Labtech POLARstar™ instrument (525 nm excitation, 560 nm emission, Bottom Read mode). After incubation of the dye, 50 ml of the test substances in the desired concentrations, or 50 µl of ES buffer for control purposes, are introduced into separate cavities of the measuring plate and incubated for 30 min at room temperature while being shielded from light. The fluorescence intensity of the dye is then measured for 5 min and the fluorescence value $F_1$ of each well is thus determined at a given, constant time. 15 µl of a 100 mM KCl solution (final concentration 92 mM) are then added to each well. The change in fluorescence is subsequently measured until all the relevant measured values have been obtained (mainly 5-30 min). At a given time after KCl application, a fluorescence value $F_2$ is determined, in this case at the time of the fluorescence peak.

For calculation, the fluorescence intensity $F_2$ is compared with the fluorescence intensity $F_1$, and the agonistic activity of the target compound on the potassium channel is determined therefrom. $F_2$ and $F_1$ are calculated as follows:

$$\left(\frac{F_2 - F_1}{F_1}\right) \times 100 = \frac{\Delta F}{F}(\%)$$

In order to determine whether a substance has agonistic activity, $$\frac{\Delta F}{F},$$

for example, can be compared with $$\left(\frac{\Delta F}{F}\right)_K$$

of control cells.

$$\left(\frac{\Delta F}{F}\right)_K$$

is determined by adding to the reaction batch only the buffer solution instead of the test substance, determining the value $F_{1K}$ of the fluorescence intensity, adding the potassium ions as described above, and measuring a value $F_{2K}$ of the fluorescence intensity. $F_{2K}$ and $F_{1K}$ are then calculated as follows:

$$\left(\frac{F_{2K} - F_{1K}}{F_{1K}}\right) \times 100 = \left(\frac{\Delta F}{F}\right)_K(\%)$$

A substance has an agonistic activity on the potassium channel when $$\frac{\Delta F}{F}$$

is greater than $$\left(\frac{\Delta F}{F}\right)_K:$$

$$\frac{\Delta F}{F} \rangle \left(\frac{\Delta F}{F}\right)_K$$

Independently of the comparison of $$\frac{\Delta F}{F} \text{ with } \left(\frac{\Delta F}{F}\right)_K$$

it is possible to conclude that a target compound has agonistic activity if an increase in $$\frac{\Delta F}{F}$$

is to be observed as the dosage of the target compound increases.

Calculations of $EC_{50}$ values are carried out with the aid of 'Prism v4.0' software (GraphPad Software™).

Low-Intensity Tail Flick in the Rat

The antinociceptive effectiveness of the test substance towards an acute, noxious thermal stimulus was studied in the focal ray (tail flick) test in the rat according to the method of D'Amour and Smith (J. Pharm. Exp. Ther. 72, 74 79 (1941)). Male Sprague-Dawley rats (breeder: Janvier, Le Genest St. Isle, France) weighing from 200 to 250 g were used for this purpose. The animals were accommodated individually in special test compartments and the base of the tail was exposed to the focused ray of an analgesia meter (model 2011, Rhema Labortechnik, Hofheim, Germany). 10 animals were used per group. Before a substance according to the invention was administered, the withdrawal latency (time from switching on of the focal ray to the sudden withdrawal of the tail) was determined twice at an interval of five minutes and the mean value was defined as the control latency time. The intensity of the focal ray was chosen so that the control latency time was 7 to 9 seconds. Measurement of the withdrawal latency was then repeated 10, 20, 30 and 60 minutes after peroral administration of substance. The antinociceptive action of the test substance was determined as the increase in the withdrawal latency time according to the following formula:

$$MPE[\%] = [(T_1 - T_0)/(T_2 - T_0)] \times 100$$

where: $T_0$=control latency time before administration of substance, $T_1$=latency time after administration of substance, $T_2$=maximum exposure time to the focal ray (30 seconds), MPE=maximum possible effect.

Variance analysis (repeated measures ANOVA) was used to test for statistically significant differences between the substance group and the vehicle group. The level of significance was set at $\leq 0.05$.

Pharmacological Data

The results from the pharmacological models described above are summarized in Table 3.

TABLE 3

| Exemplary compound | Fluorimetry $EC_{50}$ [nM] | Fluorimetry % efficacy (retigabine 50 μM = 100%) | Low-intensity tail flick rat p.o. % effect (dose [mg/kg]) |
|---|---|---|---|
| 1 | 170 | 132 | |
| 2 | 1349 | 97 | |
| 3 | | 53 | |
| 4 | 772 | 126 | |
| 5 | 435 | 161 | |
| 7 | | 91 | |
| 8 | | 37 | |
| 9 | 1354 | 157 | |
| 10 | | 13 | |
| 12 | 2919 | 170 | |
| 13 | 302 | 200 | |
| 16 | 74 | 176 | |
| 17 | 128 | 176 | |

TABLE 3-continued

| Exemplary compound | Fluorimetry EC$_{50}$ [nM] | Fluorimetry % efficacy (retigabine 50 μM = 100%) | Low-intensity tail flick rat p.o. % effect (dose [mg/kg]) |
|---|---|---|---|
| 18 | 111 | 160 | |
| 19 | 37 | 171 | |
| 20 | 49 | 174 | |
| 21 | 364 | 126 | |
| 22 | 2350 | 150 | |
| 23 | 3766 | 163 | |
| 24 | 11 | 122 | |
| 25 | 1016 | 216 | |
| 26 | 126 | 244 | |
| 27 | 85 | 210 | 18 (10.0) |
| 28 | 1571 | 192 | |
| 29 | 275 | 159 | |
| 30 | 630 | 261 | |
| 31 | 437 | 98 | |
| 32 | 3125 | 191 | |
| 33 | 451 | 242 | |
| 34 | 463 | 204 | |
| 35 | 242 | 221 | |
| 36 | 45 | 78 | |
| 37 | 74 | 89 | |
| 38 | 144 | 176 | |
| 39 | 250 | 250 | |
| 40 | 129 | 144 | 26 (21.5) |
| 41 | 157 | 159 | |
| 42 | 128 | 164 | |
| 43 | 896 | 46 | |
| 44 | 2962 | 167 | |
| 45 | 1606 | 224 | |
| 46 | 672 | 238 | |
| 47 | 218 | 183 | |
| 48 | 148 | 183 | |
| 49 | 231 | 174 | |
| 50 | 1491 | 169 | |
| 51 | 198 | 192 | 49 (21.5) |
| 52 | 496 | 190 | |
| 53 | 302 | 220 | 0 (10.0) |
| 54 | 133 | 240 | 20 (10.0) |
| 55 | 227 | 149 | |
| 56 | 1014 | 251 | |
| 57 | 252 | 83 | |
| 58 | 3875 | 174 | |
| 59 | 210 | 83 | |
| 60 | 263 | 236 | |
| 61 | 221 | 283 | |
| 62 | 182 | 274 | |
| 63 | 34 | 72 | |
| 64 | 49 | 100 | |
| 65 | 40 | 97 | 49 (10.0) |
| 66 | 50 | 121 | |
| 67 | 113 | 290 | |
| 68 | 65 | 280 | 32 (10.0) |
| 69 | 140 | 259 | |
| 70 | 244 | 308 | |
| 71 | 72 | 107 | |
| 72 | 85 | 85 | |
| 73 | 377 | 268 | |
| 74 | 62 | 260 | |
| 75 | 37 | 261 | |
| 76 | | 33 | |
| 77 | 233 | 118 | |
| 78 | 319 | 53 | |
| 79 | 101 | 103 | |
| 80 | 77 | 104 | |
| 81 | 8023 | 89 | |
| 82 | 6457 | 96 | |
| 83 | 139 | 171 | |
| 84 | 3512 | 55 | |
| 85 | 394 | 59 | |
| 86 | | 26 | |
| 87 | 101 | 116 | |
| 88 | 3759 | 53 | |
| 89 | 5447 | 72 | |
| 90 | | 37 | |
| 91 | 184 | 241 | |
| 92 | 138 | 270 | |
| 93 | 2809 | 154 | |
| 94 | 2215 | 181 | |
| 95 | 2061 | 147 | |
| 96 | 660 | 194 | |
| 97 | 134 | 196 | |
| 98 | | 29 | |
| 99 | 178 | 70 | |
| 100 | 1592 | 48 | |
| 101 | | 38 | |
| 102 | 456 | 111 | |
| 103 | 111 | 129 | |
| 104 | 361 | 87 | |
| 105 | 479 | 166 | |
| 106 | 191 | 95 | |
| 107 | 57 | 119 | 20 (21.5) |
| 108 | 165 | 143 | |
| 109 | 180 | 129 | |
| 110 | 462 | 110 | |
| 111 | 11061 | 61 | |
| 112 | 494 | 104 | |
| 113 | 5199 | 90 | |
| 114 | 553 | 128 | |
| 115 | 42 | 213 | |
| 116 | 62 | 186 | ED$_{50}$ 5.4 |
| 117 | 35 | 160 | |
| 118 | 37 | 159 | |
| 119 | | 30 | |
| 120 | 307 | 61 | |
| 121 | 256 | 99 | |
| 122 | 153 | 94 | |
| 123 | 155 | 168 | |
| 124 | 17 | 114 | ED$_{50}$ 3.5 |
| 125 | 1404 | 99 | |
| 126 | 627 | 177 | |
| 127 | 1857 | 147 | |
| 128 | 1846 | 122 | |
| 129 | 325 | 122 | |
| 130 | 465 | 164 | |
| 131 | | 25 | |
| 132 | 82 | 120 | |
| 133 | 106 | 185 | 61 (10.0) |
| 134 | 268 | 224 | 40 (21.5) |
| 135 | 3143 | 154 | |
| 136 | | 28 | |
| 137 | 366 | 93 | |
| 138 | 417 | 92 | |
| 139 | 101 | 81 | |
| 140 | 312 | 88 | |
| 141 | 12773 | 86 | |
| 142 | 97 | 260 | |
| 143 | 1513 | 175 | |
| 144 | 815 | 215 | |
| 145 | 1493 | 174 | |
| 146 | 2551 | 193 | |
| 147 | | 34 | |
| 148 | 1958 | 85 | |
| 149 | 93 | 181 | |
| 150 | 1492 | 96 | |
| 151 | 667 | 95 | |
| 152 | 1292 | 89 | |
| 153 | 1251 | 155 | |
| 154 | 237 | 207 | |
| 155 | 657 | 159 | |
| 156 | 110 | 249 | |
| 157 | | 88 | |
| 158 | | 30 | |
| 159 | 670 | 113 | |
| 160 | 228 | 74 | |
| 161 | 145 | 67 | |

TABLE 3-continued

| Exemplary compound | Fluorimetry EC$_{50}$ [nM] | Fluorimetry % efficacy (retigabine 50 μM = 100%) | Low-intensity tail flick rat p.o. % effect (dose [mg/kg]) |
|---|---|---|---|
| 162 | 166 | 83 | |
| 163 | 537 | 89 | |
| 164 | 32 | 287 | 20 (4.64) |
| 165 | 30 | 119 | |
| 166 | 46 | 206 | |
| 167 | 2714 | 77 | |
| 168 | 17 | 110 | |
| 169 | 19 | 224 | ED$_{50}$ 2.7 |
| 170 | 24 | 229 | 20 (4.64) |
| 171 | 432 | 181 | |
| 172 | 1046 | 196 | |
| 173 | 156 | 185 | |
| 174 | 134 | 213 | |
| 175 | 126 | 173 | |
| 176 | 40 | 108 | |
| 177 | 76 | 192 | |
| 178 | 96 | 270 | |
| 179 | 378 | 234 | |
| 180 | 47 | 224 | 64 (10.0) |
| 181 | 1552 | 254 | |
| 182 | 366 | 110 | |
| 183 | 43 | 109 | |
| 184 | | 23 | |
| 185 | 167 | 212 | |
| 186 | 236 | 191 | |
| 187 | 805 | 231 | |
| 188 | 315 | 210 | |
| 189 | 287 | 161 | |
| 190 | 26 | 214 | |
| 191 | 37 | 202 | |
| 192 | 32 | 195 | |
| 193 | 371 | 206 | |
| 194 | 232 | 203 | |
| 195 | 48 | 122 | |
| 196 | 3710 | 190 | |
| 197 | 14717 | 128 | |
| 198 | 8840 | 110 | |
| 199 | 20 | 124 | |
| 200 | 40 | 230 | |
| 201 | 40 | 128 | |
| 202 | 71 | 235 | |
| 203 | 20 | 233 | |
| 204 | 11 | 125 | |
| 205 | 28 | 294 | |
| 206 | 40 | 293 | |
| 207 | 34 | 119 | |
| 208 | 27 | 207 | |
| 209 | 9 | 228 | |
| 210 | 14 | 276 | |
| 211 | 8828 | 87 | |
| 212 | 427 | 184 | |

The invention claimed is:

1. A substituted nicotinamide of the formula (1):

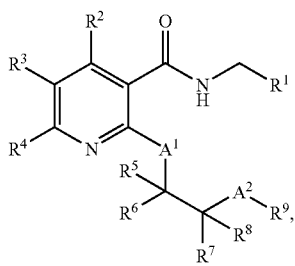

wherein
A$^1$ represents CR$^{10}$R$^{11}$ or S;
A$^2$ represents CR$^{12}$R$^{13}$, C(=O), O, S, S(=O) or S(=O)$_2$;
R$^1$ represents C$_{1-10}$-alkyl or C$_{2-10}$-heteroalkyl, in each case saturated or unsaturated, branched or unbranched, unsubstituted or mono- or poly-substituted; C$_{3-10}$-cycloalkyl or heterocyclyl, in each case saturated or unsaturated, unsubstituted or mono- or poly-substituted; aryl or heteroaryl, in each case unsubstituted or mono- or poly-substituted;
C$_{1-8}$-alkyl- or C$_{2-8}$-heteroalkyl-bridged C$_{3-10}$-cycloalkyl or heterocyclyl, in each case saturated or unsaturated, unsubstituted or mono- or poly-substituted, wherein the alkyl or heteroalkyl chain can in each case be branched or unbranched, saturated or unsaturated, unsubstituted or mono- or poly-substituted; or C$_{1-8}$-alkyl- or C$_{2-8}$-heteroalkyl-bridged aryl or heteroaryl, in each case unsubstituted or mono- or poly-substituted, wherein the alkyl or heteroalkyl chain can in each case be branched or unbranched, saturated or unsaturated, unsubstituted or mono- or poly-substituted;
R$^2$, R$^3$ and R$^4$ each independently of the others represents H; F; Cl; Br; I; NO$_2$; CF$_3$; CN; OH; OCF$_3$; SH; SCF$_3$; methyl; CH$_2$-O-methyl; CH$_2$—OH; C$_{2-6}$-alkyl, O—C$_{1-6}$-alkyl, or S—C$_{1-6}$-alkyl, in each case saturated or unsaturated, branched or unbranched, unsubstituted or mono- or poly-substituted; C$_{3-7}$-cycloalkyl, saturated or unsaturated, branched or unbranched, unsubstituted or mono- or poly-substituted; NR$^a$R$^b$, wherein R$^a$ and R$^b$ each independently of the other represents H or C$_{1-4}$-alkyl, saturated or unsaturated, branched or unbranched, unsubstituted or mono- or poly-substituted, or R$^a$ and R$^b$, together with the nitrogen atom joining them, form a heterocyclyl, saturated or unsaturated, branched or unbranched, unsubstituted or mono- or poly-substituted;
R$^5$, R$^6$, R$^7$, R$^8$, R$^{10}$, R$^{11}$, R$^{12}$ and R$^{13}$ each independently of the others represents H; F; Cl; Br; I; NO$_2$; CF$_3$; CN; OH; OCF$_3$; SH; SCF$_3$; C$_{1-10}$-alkyl, C$_{2-10}$-heteroalkyl, O—C$_{1-10}$-alkyl or S—C$_{1-10}$-alkyl, in each case saturated or unsaturated, branched or unbranched, unsubstituted or mono- or poly-substituted; C$_{3-10}$-cycloalkyl, saturated or unsaturated, branched or unbranched, unsubstituted or mono- or poly-substituted;
with the proviso that when R$^5$, R$^6$, R$^7$ and R$^8$ each denotes H and A$^1$ represents S, A$^2$ may not denote S, S(=O) or S(=O)$_2$;
or R$^5$ and R$^6$ or R$^7$ and R$^8$ or R$^{10}$ and R$^{11}$ or R$^{12}$ and R$^{13}$ or R$^5$ and R$^{11}$ or R$^5$ and R$^{13}$ or R$^7$ and R$^{13}$ or R$^7$ and R$^{11}$ or R$^{11}$ and R$^{13}$, together with the carbon atom(s) joining them, form a C$_{3-8}$-cycloalkyl or a heterocyclyl having from three to eight ring members, in each case saturated or unsaturated, unsubstituted or mono- or poly-substituted; wherein the remaining substituents R$^5$, R$^6$, R$^7$, R$^8$, R$^{10}$, R$^{11}$, R$^{12}$ and R$^{13}$ in each case have the meaning given above;
or R$^5$ and R$^7$, together with the carbon atom(s) joining them, form a C$_{3-8}$-cycloalkyl, saturated or unsaturated, unsubstituted or mono- or poly-substituted; or a heterocyclyl having from three to eight ring members, unsaturated, unsubstituted or mono- or poly-substituted; wherein the remaining substituents R$^6$, R$^8$, R$^{10}$, R$^{11}$, R$^{12}$ and R$^{13}$ in each case have the meaning given above;
R$^9$ represents C$_{3-10}$-cycloalkyl, saturated or unsaturated, unsubstituted or mono- or poly-substituted; or represents aryl or heteroaryl, in each case unsubstituted or mono- or poly-substituted;

with the proviso that when $A^2$ represents O or S and $R^9$ represents heteroaryl, unsubstituted or mono- or poly-substituted, the heteroaryl is bound via a carbon atom of the heteroaryl;

wherein "substituted" in the case of substitution on alkyl, heteroalkyl, heterocyclyl and cycloalkyl stands for the substitution of one or more hydrogen atoms, in each case independently of one another, by F; Cl; Br; I; $NO_2$; $CF_3$; CN; =O; $C_{1-8}$-alkyl; $C_{2-8}$-heteroalkyl; aryl; heteroaryl; $C_{3-10}$-cycloalkyl; heterocyclyl; $C_{1-8}$-alkyl- or $C_{2-8}$-heteroalkyl-bridged aryl, heteroaryl, $C_{3-10}$-cycloalkyl or heterocyclyl; CHO; C(=O)$C_{1-8}$-alkyl; C(=O)aryl; C(=O)heteroaryl; $CO_2H$; C(=O)O—$C_{1-8}$-alkyl; C(=O)O-aryl; C(=O)O-heteroaryl; $CONH_2$; C(=O)NH—$C_{1-8}$-alkyl; C(=O)N($C_{1-8}$-alkyl)$_2$; C(=O)NH-aryl; C(=O)N(aryl)$_2$; C(=O)NH-heteroaryl; C(=O)N(heteroaryl)$_2$; C(=O)N($C_{1-8}$-alkyl)(aryl); C(=O)N($C_{1-8}$-alkyl)(heteroaryl); C(=O)N(heteroaryl)(aryl); OH; O—$C_{1-8}$-alkyl; $OCF_3$; O—($C_{1-8}$-alkyl)-OH; O—($C_{1-8}$-alkyl)-O—$C_{1-8}$-alkyl; O-benzyl; O-aryl; O-heteroaryl; O—C(=O)$C_{1-8}$-alkyl; O—C(=O)aryl; O—C(=O)heteroaryl; $NH_2$; NH—$C_{1-8}$-alkyl; N($C_{1-8}$-alkyl)$_2$; NH—C(=O)$C_{1-8}$-alkyl; N($C_{1-8}$-alkyl)-C(=O)$C_{1-8}$-alkyl; N(C(=O)$C_{1-8}$-alkyl)$_2$; NH—C(=O) -aryl; NH—C(=O)-heteroaryl; SH; S—$C_{1-8}$-alkyl; $SCF_3$; S-benzyl; S-aryl; S-heteroaryl; S(=O)$_2C_{1-8}$-alkyl; S(=O)$_2$aryl; S(=O)$_2$heteroaryl; S(=O)$_2$OH; S(=O)$_2$O—$C_{1-8}$-alkyl; S(=O)$_2$O-aryl; S(=O)$_2$O-heteroaryl; S(=O)$_2$—NH—$C_{1-8}$-alkyl; S(=O)$_2$—NH-aryl; and S(=O)$_2$—NH—$C_{1-8}$-heteroaryl;

wherein "substituted" in the case of substitution on aryl or heteroaryl stands for the substitution of one or more hydrogen atoms, in each case independently of one another, by F; Cl; Br; I; $NO_2$; $CF_3$; CN; $C_{1-8}$-alkyl; $C_{2-8}$-heteroalkyl; aryl; heteroaryl; $C_{3-10}$-cycloalkyl; heterocyclyl; $C_{1-8}$-alkyl- or $C_{2-8}$-heteroalkyl-bridged aryl, heteroaryl, $C_{3-10}$-cycloalkyl or heterocyclyl; CHO; C(=O)$C_{1-8}$-alkyl; C(=O)aryl; C(=O)heteroaryl; $CO_2H$; C(=O)O—$C_{1-8}$-alkyl; C(=O)O-aryl; C(=O)O-heteroaryl; $CONH_2$; C(=O)NH—$C_{1-8}$-alkyl; C(=O)N($C_{1-8}$-alkyl)$_2$; C(=O)NH-aryl; C(=O)N(aryl)$_2$; C(=O)NH-heteroaryl; C(=O)N(heteroaryl)$_2$; C(=O)N($C_{1-8}$-alkyl)(aryl); C(=O)N($C_{1-8}$-alkyl)(heteroaryl); C(=O)N(heteroaryl)(aryl); OH; O—$C_{1-8}$-alkyl; $OCF_3$; O—($C_{1-8}$-alkyl)-OH; O—($C_{1-8}$-alkyl)-O—$C_{1-8}$-alkyl; O-benzyl; O-aryl; O-heteroaryl; O—C(=O)$C_{1-8}$-alkyl; O—C(=O)aryl; )—C(=O)heteroaryl; $NH_2$; NH—$C_{1-8}$-alkyl; N($C_{1-8}$-alkyl)$_2$; NH—C(=O)$C_{1-8}$-alkyl; N($C_{1-8}$-alkyl) -C(=O)$C_{1-8}$-alkyl; N(C(=O)$C_{1-8}$-alkyl)$_2$; NH—C(=O)-aryl; NH—C(=O)-heteroaryl; SH; S—$C_{1-8}$-alkyl; $SCF_3$; S-benzyl; S-aryl; S-heteroaryl; S(=O)$_2C_{1-8}$-alkyl; S(=O)$_2$aryl; S(=O)$_2$heteroaryl; S(=O)$_2$OH; S(=O)$_2$O—$C_{1-8}$-alkyl; S(=O)$_2$O-aryl; S(=O)$_2$O-heteroaryl; S(=O)$_2$—NH—$C_{1-8}$-alkyl; S(=O)$_2$—NH-aryl; or S(=O)$_2$—NH—$C_{1-8}$-heteroaryl;

said substituted nicotinamide being in the form of a free compound or a salt of physiologically acceptable acids or bases.

2. The substituted nicotinamide according to claim 1, wherein $A^1$ represents S; and $A^2$ represents $CR^{12}R^{13}$, O, S or S(=O)$_2$.

3. The substituted nicotinamide according to claim 1, wherein $R^1$ represents the partial structure (T1)

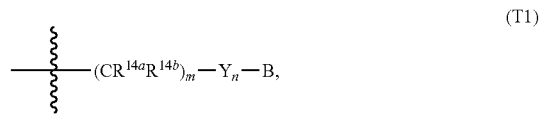

(T1)

wherein $R^{14a}$ and $R^{14b}$ each independently of the other represents H; F; Cl; Br; I; $NO_2$; $CF_3$; CN; OH; $OCF_3$; $NH_2$; $C_{1-4}$-alkyl, O—$C_{1-4}$-alkyl, NH—$C_{1-4}$-alkyl, or N($C_{1-4}$-alkyl)$_2$, in each case saturated or unsaturated, branched or unbranched, unsubstituted or mono- or poly-substituted by one or more substituents each selected independently of one another from the group consisting of F, Cl, Br, I, O—$C_{1-4}$-alkyl, OH and $OCF_3$; $C_{3-10}$-cycloalkyl or heterocyclyl, in each case saturated or unsaturated, unsubstituted or mono- or poly-substituted by one or more substituents each selected independently of one another from the group consisting of F, Cl, Br, I, $C_{1-4}$-alkyl, OH, =O,O—$C_{1-4}$-alkyl, $OCF_3$, $NH_2$, NH—$C_{1-4}$-alkyl and N($C_{1-4}$-alkyl)$_2$;

m represents 0, 1, 2 or 3;

Y represents O or $NR^{15}$, wherein $R^{15}$ represents H; $C_{1-4}$-alkyl, saturated or unsaturated, branched or unbranched, unsubstituted or mono- or poly-substituted by one or more substituents each selected independently of one another from the group consisting of F, Cl, Br, I, $C_{1-4}$-alkyl, OH, O—$C_{1-4}$-alkyl, $OCF_3$, $NH_2$, NH—$C_{1-4}$-alkyl and N($C_{1-4}$-alkyl)$_2$; or represents $C_{3-10}$-cycloalkyl, saturated or unsaturated, unsubstituted or mono- or poly-substituted by one or more substituents each selected independently of one another from the group consisting of F, Cl, Br, I, $C_{1-4}$-alkyl, OH, O—$C_{1-4}$-alkyl, $OCF_3$, $NH_2$, NH—$C_{1-4}$-alkyl and N($C_{1-4}$-alkyl)$_2$;

n represents 0 or 1,

B represents $C_{1-8}$-alkyl, saturated or unsaturated, branched or unbranched, unsubstituted or mono- or poly-substituted by one or more substituents each selected independently of one another from the group consisting of F, Cl, Br, I, $NO_2$, CN, OH, =O, O—$C_{1-4}$-alkyl, $OCF_3$, C(=O)—OH, $CF_3$, $NH_2$, NH($C_{1-4}$-alkyl), N($C_{1-4}$-alkyl)$_2$, SH, S—$C_{1-4}$-alkyl, $SCF_3$ and S(=O)$_2$OH; $C_{3-10}$-cycloalkyl or heterocyclyl, in each case saturated or unsaturated, unsubstituted or mono- or poly-substituted by one or more substituents each selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, NH($C_{1-8}$-alkyl), N($C_{1-8}$-alkyl)$_2$, SH, S—$C_{1-8}$-alkyl, $SCF_3$, S(=O)$_2$OH, benzyl, phenyl, pyridyl and thienyl, wherein benzyl, phenyl, pyridyl, thienyl can in each case be unsubstituted or mono- or poly-substituted by one or more substituents selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, NH($C_{1-8}$-alkyl), N($C_{1-8}$-alkyl)$_2$, SH, S—$C_{1-8}$-alkyl, $SCF_3$ and S(=O)$_2$OH; aryl or heteroaryl, in each case unsubstituted or mono- or poly-substituted by one or more substituents each selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl)$_2$, SH, S—$C_{1-8}$-alkyl, $SCF_3$, $S(=O)_2OH$, benzyl, phenyl, pyridyl and thienyl, wherein benzyl, phenyl, pyridyl, thienyl can in each case be unsubstituted or mono- or poly-substituted by one or more substituents selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl)$_2$, SH, S—$C_{1-8}$-alkyl, $SCF_3$ and $S(=O)_2OH$.

4. The substituted nicotinamide according to claim 3, wherein $R^{14a}$ and $R^{14b}$ each independently of the other represents H; F; Cl; Br; I; $NO_2$; $CF_3$; CN; methyl; ethyl; n-propyl; isopropyl; cyclopropyl; n-butyl; sec-butyl; tert-butyl; $CH_2CF_3$; OH; O-methyl; O-ethyl; O—$(CH_2)_2$—O—$CH_3$; O—$(CH_2)_2$—OH; $OCF_3$; $NH_2$; NH-methyl; $N(methyl)_2$; NH-ethyl; $N(ethyl)_2$; or N(methyl)(ethyl);

m represents 0, 1 or 2;

n represents 0; and

B represents $C_{1-4}$-alkyl, saturated, branched or unbranched, unsubstituted or mono- or poly-substituted by one or more substituents each selected independently of one another from the group consisting of F, Cl, Br, I, OH, O—$C_{1-4}$-alkyl, $OCF_3$ and $CF_3$; $C_{3-10}$-cycloalkyl, saturated, unsubstituted; phenyl, naphthyl, pyridyl, thienyl, in each case unsubstituted or mono- or di- or tri-substituted by one, two or three substituents each selected independently of one another from the group consisting of F, Cl, Br, I, $NO_2$, CN, OH, O—$C_{1-4}$-alkyl, $OCF_3$, $C_{1-4}$-alkyl, C(=O)—OH, $CF_3$, $NH_2$, $NH(C_{1-4}$-alkyl), $N(C_{1-4}$-alkyl)$_2$, SH, S—$C_{1-4}$-alkyl, $SCF_3$, and $S(=O)_2OH$.

5. The substituted nicotinamide according to claim 1, wherein $R^2$, $R^3$ and $R^4$ each independently of the others represents H; F; Cl; Br; I; $NO_2$; $CF_3$; CN; OH; $OCF_3$; SH; $SCF_3$; methyl; $CH_2$—O-methyl; $CH_2$—OH; $C_{2-6}$-alkyl, O—$C_{1-6}$-alkyl, or S—$C_{1-6}$-alkyl, in each case saturated or unsaturated, branched or unbranched, unsubstituted or mono- or poly-substituted by one or more substituents each selected independently of one another from the group consisting of F, Cl, Br, I, OH, =O and O—$C_{1-4}$-alkyl; $C_{3-7}$-cycloalkyl, saturated or unsaturated, branched or unbranched, unsubstituted; $NR^aR^b$, wherein $R^a$ and $R^b$ each independently of the other represents H or $C_{1-4}$-alkyl, saturated or unsaturated, branched or unbranched, unsubstituted or mono- or poly-substituted by one or more substituents each selected independently of one another from the group consisting of OH, =O and O—$C_{1-4}$-alkyl, or $R^a$ and $R^b$, together with the nitrogen atom joining them, form a heterocyclyl, saturated or unsaturated, unsubstituted or mono- or poly-substituted by $C_{1-4}$-alkyl.

6. The substituted nicotinamide according to claim 5, wherein $R^2$, $R^3$ and $R^4$ each independently of the others represents H; F; Cl; Br; I; methyl; ethyl; n-propyl, isopropyl; cyclopropyl; CN; $CF_3$; O-methyl; $OCF_3$; S-methyl; or $SCF_3$.

7. The substituted nicotinamide according to claim 1, wherein $R^5$, $R^6$, $R^7$, $R^8$, $R^{10}$, $R^{11}$, $R^{12}$ and $R^{13}$ each independently of the others represents H; F; Cl; Br; I; $NO_2$; $CF_3$; CN; OH; $OCF_3$; SH; $SCF_3$; methyl; ethyl; n-propyl; isopropyl; n-butyl; sec-butyl; tert-butyl; O-methyl; O-ethyl; O—$(CH_2)_2$—O—$CH_3$; O—$(CH_2)_2$—OH; S-methyl; S-ethyl; cyclopropyl; cyclobutyl; cyclopentyl; or cyclohexyl;

or $R^5$ and $R^6$ or $R^7$ and $R^8$ or $R^{10}$ and $R^{11}$ or $R^{12}$ and $R^{13}$ or $R^5$ and $R^{11}$ or $R^5$ and $R^7$ or $R^5$ and $R^{13}$ or $R^7$ and $R^{13}$ or $R^7$ and $R^{11}$ or $R^{11}$ and $R^{13}$, together with the carbon atom(s) joining them, form a cyclopropyl, cyclobutyl, cyclopentyl or cyclohexyl, in each case unsubstituted; wherein the remaining substituents $R^5$, $R^6$, $R^7$, $R^8$, $R^{10}$, $R^{11}$, $R^{12}$ and $R^{13}$ in each case have the meaning given above.

8. The substituted nicotinamide according to claim 1, wherein $R^9$ represents $C_{3-10}$-cycloalkyl, saturated or unsaturated, unsubstituted or mono- or poly-substituted by one or more substituents each selected independently of one another from the group consisting of F, Cl, Br, I, $NO_2$, CN, OH, =O, O—$C_{1-4}$-alkyl, $OCF_3$, $C_{1-4}$-alkyl, $CF_3$, SH, S—$C_{1-4}$-alkyl and $SCF_3$; or represents aryl or heteroaryl, in each case unsubstituted or mono- or poly-substituted by one or more substituents each selected independently of one another from the group consisting of F, Cl, Br, I, $NO_2$, CN, OH, O—$C_{1-4}$-alkyl, $OCF_3$, $C_{1-4}$-alkyl, $CF_3$, $NH_2$, $NH(C_{1-4}$-alkyl), $N(C_{1-4}$-alkyl)$_2$, SH, S—$C_{1-4}$-alkyl and $SCF_3$.

9. The substituted nicotinamide according to claim 1, wherein $R^9$ represents phenyl, pyridyl or thienyl, in each case unsubstituted or mono- or poly-substituted by one or more substituents each selected independently of one another from the group consisting of F, Cl, Br, I, CN, OH, O—$C_{1-4}$-alkyl, $OCF_3$, $C_{1-4}$-alkyl, $CF_3$, SH, S—$C_{1-4}$-alkyl and $SCF_3$.

10. The substituted nicotinamide according to claim 1, wherein $A^1$ represents S and $A^2$ represents $CR^{12}R^{13}$;

$R^1$ represents the partial structure (T1-1)

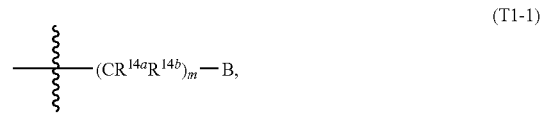

(T1-1)

wherein $R^{14a}$ and $R^{14b}$ each independently of the other represents H; F; Cl; Br; I; methyl; ethyl; n-propyl; isopropyl; n-butyl; sec-butyl; tert-butyl; OH; O-methyl; O-ethyl; O—$(CH_2)_2$—O—$CH_3$; or O—$(CH_2)_2$—OH;

m represents 0, 1 or 2;

B represents methyl; ethyl; n-propyl; isopropyl; n-butyl; sec-butyl; tert-butyl; cyclopropyl; cyclobutyl; cyclopentyl; cyclohexyl; cycloheptyl; adamantyl; bicyclo[2.2.1]heptyl; bicyclo[2.2.2]octyl; phenyl, pyridyl, thienyl, in each case unsubstituted or mono-, di- or tri-substituted by one, two or three substituents each selected independently of one another from the group consisting of F, Cl, Br, I, $NO_2$, CN, OH, O—$C_{1-4}$-alkyl, $OCF_3$, $C_{1-4}$-alkyl, C(=O)—OH, $CF_3$, $NH_2$, $NH(C_{1-4}$-alkyl), $N(C_{1-4}$-alkyl)$_2$, SH, S—$C_{1-4}$-alkyl, $SCF_3$ and $S(=O)_2OH$;

$R^2$, $R^3$ and $R^4$ each independently of the others represents H; F; Cl; methyl; ethyl; $CF_3$ or O-methyl;

$R^5$, $R^6$, $R^7$, $R^8$, $R^{10}$, $R^{11}$, $R^{12}$ and $R^{13}$ each independently of the others represents H; F; Cl; methyl; ethyl; n-propyl, isopropyl; or cyclopropyl;

$R^9$ represents phenyl, pyridyl or thienyl, unsubstituted or mono- or poly-substituted by one or more substituents each selected independently of one another from the group consisting of F, Cl, Br, I, CN, methyl, ethyl, n-propyl, isopropyl, n-butyl, sec-butyl, tert-butyl, O-methyl, O-ethyl, O-n-propyl, O-isopropyl, O-butyl, O-sec-butyl, O-tert-butyl, OH, OCF$_3$, CF$_3$, SH, S—C$_{1-4}$-alkyl and SCF$_3$.

11. The substituted nicotinamide according to claim 1, selected from the group consisting of:

1  2-(3-Phenyl-propylsulfanyl)-N-(thiophen-2-yl-methyl)-pyridine-3-carboxylic acid amide;
2  2-(3-Cyclohexyl-propylsulfanyl)-N-(thiophen-2-yl-methyl)-pyridine-3-carboxylic acid amide;
3  2-[(3-Oxo-3-phenyl-propyl)sulfanyl]-N-(thiophen-2-yl-methyl)-pyridine-3-carboxylic acid amide;
4  N-(Thiophen-2-yl-methyl)-2-[2-[3-(trifluoromethyl)-phenoxy]-ethylsulfanyl]-pyridine-3-carboxylic acid amide;
7  2-(4-Phenyl-butyl)-N-(thiophen-2-yl-methyl)-pyridine-3-carboxylic acid amide;
8  2-[3-(Benzenesulfonyl)-propyl]-N-(cyclohexyl-methyl)-pyridine-3-carboxylic acid amide;
9  N-(Cyclohexyl-methyl)-2-(4-phenyl-butyl)-pyridine-3-carboxylic acid amide;
10  2-[3-(Benzenesulfonyl)-propyl]-N-(thiophen-2-yl-methyl)-pyridine-3-carboxylic acid amide;
12  N-(Thiophen-2-yl-methyl)-2-[3-[[3-(trifluoromethyl)phenyl]sulfonyl]-propyl]-pyridine-3-carboxylic acid amide;
13  N-(Thiophen-2-yl-methyl)-2-[3-[[3-(trifluoromethyl)phenyl]sulfanyl]-propyl]-pyridine-3-carboxylic acid amide;
16  2-(2-Phenylsulfanyl-propylsulfanyl)-N-(thiophen-2-yl-methyl)-pyridine-3-carboxylic acid amide;
17  2-[3-(4-Fluorophenyl)-propylsulfanyl]-N-(thiophen-2-yl-methyl)-pyridine-3-carboxylic acid amide;
18  N-(Thiophen-2-yl-methyl)-2-[3-[3-(trifluoromethyl)phenyl]-propylsulfanyl]-pyridine-3-carboxylic acid amide;
19  2-[2-[(4-Fluorophenyl)sulfanyl]-propylsulfanyl]-N-(thiophen-2-yl-methyl) -pyridine-3-carboxylic acid amide;
20  N-(Thiophen-2-yl-methyl)-2-[2-[[3-(trifluoromethyl)phenyl]sulfanyl]-propylsulfanyl]-pyridine-3-carboxylic acid amide;
21  N-(Thiophen-2-yl-methyl)-2-[4-[3-(trifluoromethyl)-phenyl]-butyl]-pyridine-3-carboxylic acid amide;
22  2-[4-(4-Fluorophenyl)-butyl]-N-(thiophen-2-yl-methyl)-pyridine-3-carboxylic acid amide;
23  2-(3-Phenylsulfanyl-propyl)-N-(thiophen-2-yl-methyl)-pyridine-3-carboxylic acid amide;
24  2-[(1-Methyl-2-phenylsulfanyl-ethyl)sulfanyl]-N-(thiophen-2-yl-methyl) -pyridine-3-carboxylic acid amide;
25  N-(Cycloheptyl-methyl)-2-[4-[3-(trifluoromethyl)phenyl]-butyl]-pyridine-3-carboxylic acid amide;
26  N-(5-Bicyclo[2.2.1]heptanyl-methyl)-2-[4-[3-(trifluoromethyl)phenyl]-butyl]-pyridine-3-carboxylic acid amide;
27  N-(5-Bicyclo[2.2.1]heptanyl-methyl)-2-[3-[3-(trifluoromethyl)phenyl]-propylsulfanyl]-pyridine-3-carboxylic acid amide;
29  N-(Cycloheptyl-methyl)-2-[3-[(4-fluorophenyl)sulfanyl]-propyl]-pyridine-3-carboxylic acid amide;
30  N-(5-Bicyclo[2.2.1]heptanyl-methyl)-2-[3-[(4-fluorophenyl)sulfanyl]-propyl]-pyridine-3-carboxylic acid amide;
31  N-(Cycloheptyl-methyl)-2-[3-[[3-(trifluoromethyl)phenyl]sulfonyl]-propyl]-pyridine-3-carboxylic acid amide;
32  N-(5-Bicyclo[2.2.1]heptanyl-methyl)-2-[3-[[3-(trifluoromethyl)phenyl]sulfonyl]-propyl]-pyridine-3-carboxylic acid amide;
33  N-(5-Bicyclo[2.2.1]heptanyl-methyl)-2-(3-phenyl-propylsulfanyl)-pyridine-3-carboxylic acid amide;
34  N-(5-Bicyclo[2.2.1]heptanyl-methyl)-2-[3-[4-(trifluoromethyl)-phenyl]-propylsulfanyl]-pyridine-3-carboxylic acid amide;
35  N-(5-Bicyclo[2.2.1]heptanyl-methyl)-2-[3-(4-chlorophenyl)-propylsulfanyl]-pyridine-3-carboxylic acid amide;
36  N-[(3,5-Difluoro-phenyl)-methyl]-2-[3-(4-fluorophenyl)-propylsulfanyl]-pyridine-3-carboxylic acid amide;
37  N-[(5-Chloro-thiophen-2-yl)-methyl]-2-[3-(4-fluorophenyl)-propylsulfanyl]-pyridine-3-carboxylic acid amide;
38  N-[(2,2-Dimethyl-cyclopropyl)-methyl]-2-[3-(4-fluorophenyl)-propylsulfanyl]-pyridine-3-carboxylic acid amide;
39  N-(5-Bicyclo[2.2.1]heptanyl-methyl)-2-[3-(3-fluorophenyl)-propylsulfanyl]-pyridine-3-carboxylic acid amide;
40  N-(Cyclohexyl-methyl)-2-[3-(4-fluorophenyl)-propylsulfanyl]-pyridine-3-carboxylic acid amide;
41  N-(Cycloheptyl-methyl)-2-[3-(4-fluorophenyl)-propylsulfanyl]-pyridine-3-carboxylic acid amide;
43  N-(5-Bicyclo[2.2.1]heptanyl-methyl)-2-[[3-(4-fluorophenyl)-3-oxo-propyl]sulfanyl]-pyridine-3-carboxylic acid amide;
44  N-(5-Bicyclo[2.2.1]heptanyl-methyl)-2-[(3-oxo-3-phenyl-propyl)sulfanyl]-pyridine-3-carboxylic acid amide;
46  N-(5-Bicyclo[2.2.1]heptanyl-methyl)-2-(2-phenoxyethylsulfanyl)-pyridine-3-carboxylic acid amide;
47  N-(5-Bicyclo[2.2.1]heptanyl-methyl)-2-[2-[3-(trifluoromethyl)-phenoxy]-ethylsulfanyl]-pyridine-3-carboxylic acid amide;
48  2-[3-(4-Fluorophenyl)-propylsulfanyl]-N-(3,3,3-trifluoro-propyl)-pyridine-3-carboxylic acid amide;
49  N-(5-Bicyclo[2.2.1]heptanyl-methyl)-2-[2-(4-fluorophenoxy)-ethylsulfanyl]-pyridine-3-carboxylic acid amide;
52  N-(5-Bicyclo[2.2.1]heptanyl-methyl)-2-(3-naphthalen-1-yl-propylsulfanyl)-pyridine-3-carboxylic acid amide;
53  N-(5-Bicyclo[2.2.1]heptanyl-methyl)-2-[3-[3-fluoro-4-(trifluoromethyl)-phenyl]-propylsulfanyl]-pyridine-3-carboxylic acid amide;
54  N-(5-Bicyclo[2.2.1]heptanyl-methyl)-2-[3-[4-fluoro-3-(trifluoromethyl)-phenyl]-propylsulfanyl]-pyridine-3-carboxylic acid amide;
55  N-(Cyclooctyl-methyl)-2-[3-(4-fluorophenyl)-propylsulfanyl]-pyridine-3-carboxylic acid amide;
56  N-(5-Bicyclo[2.2.1]heptanyl-methyl)-2-[3-(4-methoxyphenyl)-propylsulfanyl]-pyridine-3-carboxylic acid amide;
57  2-[3-(4-Fluorophenyl)-propylsulfanyl]-N-[(4-methoxyphenyl)-methyl]-pyridine-3-carboxylic acid amide;
59  2-[3-(4-Fluorophenyl)-propylsulfanyl]-N-[[3-(trifluoromethyl)phenyl]-methyl]-pyridine-3-carboxylic acid amide;
60  N-(5-Bicyclo[2.2.1]heptanyl-methyl)-2-[3-(3,4-difluoro-phenyl)-propylsulfanyl]-pyridine-3-carboxylic acid amide;
61  N-(5-Bicyclo[2.2.1]heptanyl-methyl)-2-[3-(3,5-difluoro-phenyl)-propylsulfanyl]-pyridine-3-carboxylic acid amide;

62  N-(5-Bicyclo[2.2.1]heptanyl-methyl)-2-[3-(2,4-difluoro-phenyl)-propylsulfanyl]-pyridine-3-carboxylic acid amide;
63  N-[(2-Fluorophenyl)-methyl]-2-[3-(4-fluorophenyl)-propylsulfanyl]-pyridine-3-carboxylic acid amide;
64  N-[(3-Fluorophenyl)-methyl]-2-[3-(4-fluorophenyl)-propylsulfanyl]-pyridine-3-carboxylic acid amide;
65  N-[(4-Fluorophenyl)-methyl]-2-[3-(4-fluorophenyl)-propylsulfanyl]-pyridine-3-carboxylic acid amide;
66  N-Benzyl-2-[3-(4-fluorophenyl)-propylsulfanyl]-pyridine-3-carboxylic acid amide;
67  N-(5-Bicyclo[2.2.1]heptanyl-methyl)-2-[(1-methyl-3-phenyl-propyl)sulfanyl]-pyridine-3-carboxylic acid amide;
68  N-(5-Bicyclo[2.2.1]heptanyl-methyl)-2-[3-(3,4,5-trifluoro-phenyl)-propylsulfanyl]-pyridine-3-carboxylic acid amide;
69  N-(5-Bicyclo[2.2.1]heptanyl-methyl)-2-[3-[3-fluoro-5-(trifluoromethyl)-phenyl]-propylsulfanyl]-pyridine-3-carboxylic acid amide;
70  N-(5-Bicyclo[2.2.1]heptanyl-methyl)-2-[3-(3-methoxyphenyl)-propylsulfanyl]-pyridine-3-carboxylic acid amide;
71  N-[(3,4-Difluoro-phenyl)-methyl]-2-[3-(4-fluorophenyl)-propylsulfanyl]-pyridine-3-carboxylic acid amide;
72  N-(2,3-Dihydro-benzofuran-5-yl-methyl)-2-[3-(4-fluorophenyl)-propylsulfanyl]-pyridine-3-carboxylic acid amide;
73  N-(5-Bicyclo[2.2.1]heptanyl-methyl)-2-[3-(3-hydroxyphenyl)-propylsulfanyl]-pyridine-3-carboxylic acid amide;
74  N-(5-Bicyclo[2.2.1]heptanyl-methyl)-2-[[3-(4-fluorophenyl)-1-methyl-propyl]sulfanyl]-pyridine-3-carboxylic acid amide;
75  N-(5-Bicyclo[2.2.1]heptanyl-methyl)-2-[[3-(4-fluorophenyl)-2-methyl-propyl]sulfanyl]-pyridine-3-carboxylic acid amide;
76  2-[3-(4-Fluorophenyl)-propylsulfanyl]-N-[(2-methoxyphenyl)-methyl]-pyridine-3-carboxylic acid amide;
77  2-[3-(4-Fluorophenyl)-propylsulfanyl]-N-[(3-methoxyphenyl)-methyl]-pyridine-3-carboxylic acid amide;
78  2-[3-(4-Fluorophenyl)-propylsulfanyl]-N-phenethyl-pyridine-3-carboxylic acid amide;
79  2-[3-(4-Fluorophenyl)-propylsulfanyl]-N-[[4-(trifluoromethyloxy)-phenyl]-methyl]-pyridine-3-carboxylic acid amide;
80  2-[3-(4-Fluorophenyl)-propylsulfanyl]-N-[[4-(trifluoromethyl)-phenyl]-methyl]-pyridine-3-carboxylic acid amide;
81  2-[3-(4-Fluorophenyl)-propylsulfanyl]-N-(2-pyridine-3-yl-ethyl)-pyridine-3-carboxylic acid amide;
82  2-[3-(4-Fluorophenyl)-propylsulfanyl]-N-(2-pyridine-2-yl-ethyl)-pyridine-3-carboxylic acid amide;
83  2-[3-(4-Fluorophenyl)-propylsulfanyl]-N-[(2-hydroxyphenyl)-methyl]-pyridine-3-carboxylic acid amide;
84  2-[3-(4-Fluorophenyl)-propylsulfanyl]-N-[(3-hydroxyphenyl)-methyl]-pyridine-3-carboxylic acid amide;
85  2-[3-(4-Fluorophenyl)-propylsulfanyl]-N-[2-(m-tolyl)-ethyl]-pyridine-3-carboxylic acid amide;
86  2-[3-(4-Fluorophenyl)-propylsulfanyl]-N-[2-(o-tolyl)-ethyl]-pyridine-3-carboxylic acid amide;
87  2-[3-(4-Fluorophenyl)-propylsulfanyl]-N-[[3-(trifluoromethyloxy)-phenyl]-methyl]-pyridine-3-carboxylic acid amide;
88  2-[3-(4-Fluorophenyl)-propylsulfanyl]-N-[(4-hydroxyphenyl)-methyl]-pyridine-3-carboxylic acid amide;
89  2-[3-(4-Fluorophenyl)-propylsulfanyl]-N-(2-pyridine-4-yl-ethyl)-pyridine-3-carboxylic acid amide;
90  2-[3-(4-Fluorophenyl)-propylsulfanyl]-N-[2-(p-tolyl)-ethyl]-pyridine-3-carboxylic acid amide;
91  N-(5-Bicyclo[2.2.1]heptanyl-methyl)-2-[3-(4-fluorophenyl)-butylsulfanyl]-pyridine-3-carboxylic acid amide;
92  N-(5-Bicyclo[2.2.1]heptanyl-methyl)-2-[3-(2,4,5-trifluoro-phenyl)-propylsulfanyl]-pyridine-3-carboxylic acid amide;
93  2-[3-(4-Fluorophenyl)-propylsulfanyl]-N-(3-pyridine-2-yl-propyl)-pyridine-3-carboxylic acid amide;
94  2-[3-(4-Fluorophenyl)-propylsulfanyl]-N-(3-pyridine-3-yl-propyl)-pyridine-3-carboxylic acid amide;
95  2-[3-(4-Fluorophenyl)-propylsulfanyl]-N-(3-pyridine-4-yl-propyl)-pyridine-3-carboxylic acid amide;
96  2-[3-(4-Fluorophenyl)-propylsulfanyl]-N-propyl-pyridine-3-carboxylic acid amide;
97  N-Butyl-2-[3-(4-fluorophenyl)-propylsulfanyl]-pyridine-3-carboxylic acid amide;
98  2-(3-Pyridin-3-yl-propylsulfanyl)-N-(thiophen-2-yl-methyl)-pyridine-3-carboxylic acid amide;
99  2-[3-(p-Tolyl)-propylsulfanyl]-N-(thiophen-2-yl-methyl)-pyridine-3-carboxylic acid amide;
100  2-(4-Phenyl-butylsulfanyl)-N-(thiophen-2-yl-methyl)-pyridine-3-carboxylic acid amide;
101  2-(3-Pyridin-4-yl-propylsulfanyl)-N-(thiophen-2-yl-methyl)-pyridine-3-carboxylic acid amide;
102  2-(3-Naphthalen-2-yl-propylsulfanyl)-N-(thiophen-2-yl-methyl)-pyridine-3-carboxylic acid amide;
103  2-[3-(m-Tolyl)-propylsulfanyl]-N-(thiophen-2-yl-methyl)-pyridine-3-carboxylic acid amide;
104  N-(Thiophen-2-yl-methyl)-2-(3-thiophen-2-yl-propylsulfanyl)-pyridine-3-carboxylic acid amide;
105  2-[(1-Methyl-3-phenyl-propyl)sulfanyl]-N-(thiophen-2-yl-methyl)-pyridine-3-carboxylic acid amide;
106  N-(Thiophen-2-yl-methyl)-2-(3-thiophen-2-yl-propylsulfanyl)-pyridine-3-carboxylic acid amide;
107  2-[[1-Methyl-3-[3-(trifluoromethyl)phenyl]-propyl]sulfanyl]-N-(thiophen-2-yl-methyl) -pyridine-3-carboxylic acid amide;
108  2-[(2-Benzyl-cyclohexyl)sulfanyl]-N-(thiophen-2-yl-methyl)-pyridine-3-carboxylic acid amide;
109  2-[3-[3-Methyl-5-(trifluoromethyl)-phenyl]-propylsulfanyl]-N-(thiophen-2-yl-methyl) -pyridine-3-carboxylic acid amide;
110  2-[4-(3,4-Difluoro-phenyl)-butylsulfanyl]-N-(thiophen-2-yl-methyl)-pyridine-3-carboxylic acid amide;
111  2-(3-Pyridin-2-yl-propylsulfanyl)-N-(thiophen-2-yl-methyl)-pyridine-3-carboxylic acid amide;
113  2-[3-[4-Methyl-3-(trifluoromethyl)-phenyl]-propylsulfanyl]-N-(thiophen-2-yl-methyl) -pyridine-3-carboxylic acid amide;
114  2-[(3-Phenyl-cyclohexyl)sulfanyl]-N-(thiophen-2-yl-methyl)-pyridine-3-carboxylic acid amide;
116  2-[[3,3-Difluoro-3-(4-fluorophenyl)-propyl]sulfanyl]-N-(3,3-dimethyl-butyl) -pyridine-3-carboxylic acid amide;
117  N-(Cycloheptyl-methyl)-2-[[3,3-difluoro-3-(4-fluorophenyl)-propyl]sulfanyl]-pyridine-3-carboxylic acid amide;
118  2-[[3,3-Difluoro-3-(4-fluorophenyl)-propyl]sulfanyl]-N-(thiophen-2-yl-methyl) -pyridine-3-carboxylic acid amide;

119 2-[3-(4-Fluorophenyl)-propylsulfanyl]-N-(1,2,3,4-tetrahydro-naphthalen-2-yl-methyl) -pyridine-3-carboxylic acid amide;
120 N-(2,3-Dihydro-1H-inden-2-yl-methyl)-2-[3-(4-fluorophenyl)-propylsulfanyl]-pyridine-3-carboxylic acid amide;
121 N-(1,3-Benzodioxol-5-yl-methyl)-2-[3-(4-fluorophenyl)-propylsulfanyl]-pyridine-3-carboxylic acid amide;
122 2-[3-(4-Fluorophenyl)-propylsulfanyl]-N-[(3-phenyl-phenyl)-methyl]-pyridine-3-carboxylic acid amide;
123 2-[3-(4-Fluorophenyl)-propylsulfanyl]-N-[(3-methyl-cyclohexyl)-methyl]-pyridine-3-carboxylic acid amide;
124 2-[[3,3-Difluoro-3-(4-fluorophenyl)-propyl]sulfanyl]-N-[(4-fluorophenyl)-methyl]-pyridine-3-carboxylic acid amide;
125 N-(3,3-Dimethyl-2-oxo-butyl)-2-[3-(4-fluorophenyl)-propylsulfanyl]-pyridine-3-carboxylic acid amide;
127 2-[3-(4-Fluorophenyl)-propylsulfanyl]-N-(pyridin-3-yl-methyl)-pyridine-3-carboxylic acid amide;
128 2-[3-(4-Fluorophenyl)-propylsulfanyl]-N-(pyridin-4-yl-methyl)-pyridine-3-carboxylic acid amide;
129 3-[[[2-[3-(4-Fluorophenyl)-propylsulfanyl]-pyridine-3-carbonyl]amino]-methyl]-benzoic acid methyl ester;
130 2-[3-(4-Fluorophenyl)-propylsulfanyl]-N-[3-(2-methoxyphenyl)-propyl]-pyridine-3-carboxylic acid amide;
132 N-[(4-Fluorophenyl)-methyl]-2-[[1-methyl-3-[3-(trifluoromethyl)phenyl]-propyl]sulfanyl]-pyridine-3-carboxylic acid amide;
133 2-[3-(4-Fluorophenyl)-propylsulfanyl]-N-(3-methyl-butyl)-pyridine-3-carboxylic acid amide;
134 2-[3-(4-Fluorophenyl)-propylsulfanyl]-N-(tetrahydro-pyran-2-yl-methyl)-pyridine-3-carboxylic acid amide;
135 2-[3-(4-Fluorophenyl)-propylsulfanyl]-N-[3-(1H-pyrazol-1-yl)-propyl]-pyridine-3-carboxylic acid amide;
136 2-[3-(4-Fluorophenyl)-propylsulfanyl]-N-(naphthalen-2-yl-methyl)-pyridine-3-carboxylic acid amide;
137 N-(2,3-Dihydro-[1,4]benzodioxin-6-yl-methyl)-2-[3-(4-fluorophenyl)-propylsulfanyl]-pyridine-3-carboxylic acid amide;
138 2-[3-(4-Fluorophenyl)-propylsulfanyl]-N-[(3-morpholin-4-yl-phenyl)-methyl]-pyridine-3-carboxylic acid amide;
139 N-(2,3-Dihydro-benzofuran-6-yl-methyl)-2-[3-(4-fluorophenyl)-propylsulfanyl]-pyridine-3-carboxylic acid amide;
140 2-[3-(4-Fluorophenyl)-propylsulfanyl]-N-[[3-(1H-pyrazol-1-yl)-phenyl]-methyl]-pyridine-3-carboxylic acid amide;
141 2-[3-(4-Fluorophenyl)-propylsulfanyl]-N-[3-(1H-[1,2,3]triazol-1-yl)-propyl]-pyridine-3-carboxylic acid amide;
142 N-(7-Bicyclo[2.2.1]heptanyl-methyl)-2-[3-(4-fluorophenyl)-propylsulfanyl]-pyridine-3-carboxylic acid amide;
144 2-[3-(4-Fluorophenyl)-propylsulfanyl]-N-(thiazol-2-yl-methyl)-pyridine-3-carboxylic acid amide;
145 2-[3-(4-Fluorophenyl)-propylsulfanyl]-N-(thiazol-5-yl-methyl)-pyridine-3-carboxylic acid amide;
146 2-[3-(4-Fluorophenyl)-propylsulfanyl]-N-(oxazol-2-yl-methyl)-pyridine-3-carboxylic acid amide;
148 N-(3,3-Dimethyl-butyl)-2-[3-(4-fluorophenyl)-propylsulfanyl]-4-methyl-pyridine-3-carboxylic acid amide;
149 N-(3,3-Dimethyl-butyl)-2-[[1-methyl-3-[3-(trifluoromethyl)phenyl]-propyl]sulfanyl]-pyridine-3-carboxylic acid amide;
150 2-[3-(4-Fluorophenyl)-propylsulfanyl]-N-(quinolin-7-yl-methyl)-pyridine-3-carboxylic acid amide;
151 2-[3-(4-Fluorophenyl)-propylsulfanyl]-N-[(3-pyridin-2-yl-phenyl)-methyl]-pyridine-3-carboxylic acid amide;
152 2-[3-(4-Fluorophenyl)-propylsulfanyl]-N-[(3-pyridin-3-yl-phenyl)-methyl]-pyridine-3-carboxylic acid amide;
153 N-(3,3-Dimethyl-butyl)-2-[[(1R)-1-methyl-3-phenyl-propyl]sulfanyl]-pyridine-3-carboxylic acid amide;
154 N-(3,3-Dimethyl-butyl)-2-[[(1S)-1-methyl-3-phenyl-propyl]sulfanyl]-pyridine-3-carboxylic acid amide;
155 2-[(2-Benzyl-cyclopentyl)sulfanyl]-N-(3,3-dimethyl-butyl)-pyridine-3-carboxylic acid amide;
156 N-(7-Bicyclo[2.2.1]heptanyl-methyl)-2-[3-[3-(trifluoromethyl)phenyl]-propylsulfanyl]-pyridine-3-carboxylic acid amide;
157 2-[3-(4-Fluorophenyl)-propylsulfanyl]-N-[3-(1H-[1,2,4]triazol-1-yl)-propyl]-pyridine-3-carboxylic acid amide;
158 2-[3-(4-Fluorophenyl)-propylsulfanyl]-N-([1,3,4]oxadiazol-2-yl-methyl)-pyridine-3-carboxylic acid amide;
159 2-[3-(4-Fluorophenyl)-propylsulfanyl]-N-[(3-pyridin-4-yl-phenyl)-methyl]-pyridine-3-carboxylic acid amide;
160 N-[[4-(Cyclopropyl-methyl)-3,4-dihydro-2H-[1,4]benzoxazin-6-yl]-methyl]-2-[3-(4-fluorophenyl)-propylsulfanyl]-pyridine-3-carboxylic acid amide;
161 N-[(4-Ethyl-3,4-dihydro-2H-[1,4]benzoxazin-6-yl)-methyl]-2-[3-(4-fluorophenyl)-propylsulfanyl]-pyridine-3-carboxylic acid amide;
162 2-[3-(4-Fluorophenyl)-propylsulfanyl]-N-[(4-methyl-3,4-dihydro-2H -[1,4]benzoxazin-6-yl)-methyl]-pyridine-3-carboxylic acid amide;
163 2-[3-(4-Fluorophenyl)-propylsulfanyl]-N-(3-methyl-3-phenyl-butyl)-pyridine-3-carboxylic acid amide;
164 N-(7-Bicyclo[2.2.1]heptanyl-methyl)-2-[[3,3-difluoro-3-(4-fluorophenyl)-propyl]sulfanyl]-pyridine-3-carboxylic acid amide;
165 2-[[3,3-Difluoro-3-[3-(trifluoromethyl)phenyl]-propyl]sulfanyl]-N-[(4-fluorophenyl)-methyl]-pyridine-3-carboxylic acid amide;
166 2-[[3,3-Difluoro-3-[3-(trifluoromethyl)phenyl]-propyl]sulfanyl]-N-(3,3-dimethyl-butyl) -pyridine-3-carboxylic acid amide;
168 2-[[3,3-Difluoro-3-(4-fluorophenyl)-propyl]sulfanyl]-N-[(3-fluorophenyl)-methyl]-pyridine-3-carboxylic acid amide;
170 N-Butyl-2-[[3,3-difluoro-3-(4-fluorophenyl)-propyl]sulfanyl]-pyridine-3-carboxylic acid amide;
171 2-[[3,3-Difluoro-3-(4-fluorophenyl)-propyl]sulfanyl]-N-(2-methoxy-ethyl) -pyridine-3-carboxylic acid amide;
172 2-[3-(4-Fluorophenyl)-propylsulfanyl]-N-(2-methoxy-ethyl)-pyridine-3-carboxylic acid amide;
173 N-[(4-Fluoro-2-hydroxy-phenyl)-methyl]-2-[3-(4-fluorophenyl)-propylsulfanyl]-pyridine-3-carboxylic acid amide;
174 2-[3-(4-Fluorophenyl)-propylsulfanyl]-N-(furan-2-yl-methyl)-pyridine-3-carboxylic acid amide;
175 2-[3-(4-Fluorophenyl)-propylsulfanyl]-N-[(5-methyl-furan-2-yl)-methyl]-pyridine-3-carboxylic acid amide;

176 N-[(4-Fluorophenyl)-methyl]-2-[[3-(4-fluorophenyl)-1-methyl-propyl]sulfanyl]-pyridine-3-carboxylic acid amide;

177 2-[[3-(4-Fluorophenyl)-1-methyl-propyl]sulfanyl]-N-(3-methyl-butyl)-pyridine-3-carboxylic acid amide;

178 N-(7-Bicyclo[2.2.1]heptanyl-methyl)-2-[[3-(4-fluorophenyl)-1-methyl-propyl]sulfanyl]-pyridine-3-carboxylic acid amide;

179 2-[[3,3-Difluoro-3-(4-fluorophenyl)-propyl]sulfanyl]-N-(tetrahydro-furan-2-yl-methyl)-pyridine-3-carboxylic acid amide;

180 2-[[3,3-Difluoro-3-(4-fluorophenyl)-propyl]sulfanyl]-N-(tetrahydro-pyran-2-yl-methyl)-pyridine-3-carboxylic acid amide;

181 2-[3-(4-Fluorophenyl)-propylsulfanyl]-N-(tetrahydro-furan-2-yl-methyl)-pyridine-3-carboxylic acid amide;

182 2-[3-(4-Fluorophenyl)-propylsulfanyl]-N-(2-methoxy-3,3-dimethyl-butyl)-pyridine-3-carboxylic acid amide;

183 2-[[3,3-Difluoro-3-(4-fluorophenyl)-propyl]sulfanyl]-N-(m-tolyl-methyl)-pyridine-3-carboxylic acid amide;

184 2-[[3,3-Difluoro-3-(4-fluorophenyl)-propyl]sulfanyl]-N-[(3,5-dimethyl-phenyl)-methyl]-pyridine-3-carboxylic acid amide;

185 2-[[3,3-Difluoro-3-(4-fluorophenyl)-propyl]sulfanyl]-N-propyl-pyridine-3-carboxylic acid amide;

186 2-[[3,3-Difluoro-3-(4-fluorophenyl)-propyl]sulfanyl]-N-hexyl-pyridine-3-carboxylic acid amide;

187 2-[[3,3-Difluoro-3-(4-fluorophenyl)-propyl]sulfanyl]-N-(tetrahydro-furan-3-yl-methyl)-pyridine-3-carboxylic acid amide;

188 2-[[3,3-Difluoro-3-(4-fluorophenyl)-propyl]sulfanyl]-N-(tetrahydro-pyran-3-yl-methyl)-pyridine-3-carboxylic acid amide;

189 2-[[3,3-Difluoro-3-(4-fluorophenyl)-propyl]sulfanyl]-N-(tetrahydro-pyran-4-yl-methyl)-pyridine-3-carboxylic acid amide;

190 2-[[3,3-Difluoro-3-(4-fluorophenyl)-propyl]sulfanyl]-N-(furan-2-yl-methyl)-pyridine-3-carboxylic acid amide;

191 2-[[3,3-Difluoro-3-(4-fluorophenyl)-propyl]sulfanyl]-N-[(5-methyl-furan-2-yl)-methyl]-pyridine-3-carboxylic acid amide;

192 2-[[3,3-Difluoro-3-(4-fluorophenyl)-propyl]sulfanyl]-N-pentyl-pyridine-3-carboxylic acid amide;

193 2-[[3,3-Difluoro-3-(4-fluorophenyl)-propyl]sulfanyl]-N-(3-methoxy-butyl)-pyridine-3-carboxylic acid amide;

194 2-[[3,3-Difluoro-3-(4-fluorophenyl)-propyl]sulfanyl]-N-(2-methoxy-propyl)-pyridine-3-carboxylic acid amide;

195 2-[[3,3-Difluoro-3-(4-fluorophenyl)-propyl]sulfanyl]-N-(2-methoxy-butyl)-pyridine-3-carboxylic acid amide;

196 3-[[2-[[3,3-Difluoro-3-(4-fluorophenyl)-propyl]sulfanyl]-pyridine-3-carbonyl]amino]-propionic acid methyl ester;

197 3-[[2-[[3,3-Difluoro-3-(4-fluorophenyl)-propyl]sulfanyl]-pyridine-3-carbonyl]amino]-propionic acid;

198 2-[[3,3-Difluoro-3-(4-fluorophenyl)-propyl]sulfanyl]-N-(2-dimethylaminoethyl)-pyridine-3-carboxylic acid amide;

199 2-[[3-(3,4-Difluoro-phenyl)-1-methyl-propyl]sulfanyl]-N-[(4-fluorophenyl)-methyl]-pyridine-3-carboxylic acid amide;

200 2-[[3-(3,4-Difluoro-phenyl)-1-methyl-propyl]sulfanyl]-N-(3-methyl-butyl)-pyridine-3-carboxylic acid amide;

201 N-[(4-Fluorophenyl)-methyl]-2-[[3-(3-fluorophenyl)-1-methyl-propyl]sulfanyl]-pyridine-3-carboxylic acid amide;

202 2-[[3-(3-Fluorophenyl)-1-methyl-propyl]sulfanyl]-N-(3-methyl-butyl)-pyridine-3-carboxylic acid amide;

203 N-(3-Methyl-butyl)-2-[[1-methyl-3-[3-(trifluoromethyl)phenyl]-propyl]sulfanyl]-pyridine-3-carboxylic acid amide;

204 2-[[3-(3,4-Difluoro-phenyl)-3,3-difluoro-propyl]sulfanyl]-N-[(4-fluorophenyl)-methyl]-pyridine-3-carboxylic acid amide;

205 N-(1-Bicyclo[2.2.1]heptanyl-methyl)-2-[[3,3-difluoro-3-(4-fluorophenyl)-propyl]sulfanyl]-pyridine-3-carboxylic acid amide;

206 N-(1-Bicyclo[2.2.1]heptanyl-methyl)-2-[3-(4-fluorophenyl)-propylsulfanyl]-pyridine-3-carboxylic acid amide;

207 N-[(4-Fluorophenyl)-methyl]-2-[3-[3-(trifluoromethyl)phenyl]-propylsulfanyl]-pyridine-3-carboxylic acid amide;

208 N-(3-Methyl-butyl)-2-[3-[3-(trifluoromethyl)phenyl]-propylsulfanyl]-pyridine-3-carboxylic acid amide;

209 2-[[3-(3,4-Difluoro-phenyl)-3,3-difluoro-propyl]sulfanyl]-N-(3-methyl-butyl)-pyridine-3-carboxylic acid amide;

210 N-(7-Bicyclo[2.2.1]heptanyl-methyl)-2-[[3-(3,4-difluoro-phenyl)-3,3-difluoro-propyl]sulfanyl]-pyridine-3-carboxylic acid amide;

211 2-[[3,3-Difluoro-3-(4-fluorophenyl)-propyl]sulfanyl]-N-(2-hydroxy-ethyl)-pyridine-3-carboxylic acid amide; and 224 N-[(4-Fluoro-2-methoxy-phenyl)-methyl]-2-[3-(4-fluorophenyl)-propylsulfanyl]-pyridine-3-carboxylic acid amide;

and physiologically acceptable salts thereof.

12. A pharmaceutical composition comprising at least one substituted nicotinamide according to claim 1, in each case in the form of an individual stereoisomer or a mixture thereof, in the form of a free compound and/or a physiologically acceptable salt thereof, and optionally one or more suitable additives and/or auxiliary substances and/or optionally further active ingredients.

* * * * *

UNITED STATES PATENT AND TRADEMARK OFFICE
CERTIFICATE OF CORRECTION

PATENT NO.       : 8,178,684 B2
APPLICATION NO.  : 12/720894
DATED            : May 15, 2012
INVENTOR(S)      : Sven Kühnert et al.

It is certified that error appears in the above-identified patent and that said Letters Patent is hereby corrected as shown below:

In the Specification

Column 1, line 47, "post" should read -- Dost --.

Column 4, line 37, "N($C_{1-8}$-alkyl)-O" should read -- N($C_{1-8}$-alkyl)-C --.

Column 4, line 60, "N($C_{1-8}$-alkyl)-O" should read -- N($C_{1-8}$-alkyl)-C --.

Column 4, line 61, "NH-O" should read -- NH-C --.

Column 7, line 8, "tetrahydro-indolinyl" should read -- tetrahydroindolinyl --.

Column 7, line 9, "tetrahydro-pyridoindolyl" should read -- tetrahydropyridoindolyl --.

Column 7, line 47, "benzo-furanyl" should read -- benzofuranyl --.

Column 7, line 49, "benzo-triazolyl" should read -- benzotriazolyl --.

Column 8, line 14, "-O($CH_3$)$_2$" should read -- -C($CH_3$)$_2$ --.

Column 8, line 26, "-C≡O-" should read -- -C≡C- --.

Column 8, line 29, "-$CH_2$-C=C-" should read -- -$CH_2$-C≡C- --.

Column 8, line 30, "-C=C-$CH_2$-" should read -- -C≡C-$CH_2$- --.

Column 9, line 32, "0-($C_{1-8}$–alkyl)" should read -- O-($C_{1-8}$–alkyl) --.

Column 9, line 58 (at beginning of line), "cycloalkyl" should read -- $C_{3-10}$-cycloalkyl --.

Column 9, line 64, "N($C_{1-8}$-alkyl)-O" should read -- N($C_{1-8}$-alkyl)-C --.

Column 10, line 41, "N($C_{1-8}$-alkyl)-O" should read -- N($C_{1-8}$-alkyl)-C --.

Signed and Sealed this
Nineteenth Day of November, 2013

Teresa Stanek Rea
*Deputy Director of the United States Patent and Trademark Office*

CERTIFICATE OF CORRECTION (continued)
U.S. Pat. No. 8,178,684 B2

Column 14, line 18, "0-$C_{1-8}$-alkyl" should read -- O-$C_{1-8}$-alkyl --.

Column 14, line 52, "0-$C_{1-8}$-alkyl" should read -- O-$C_{1-8}$-alkyl --.

Column 15, line 11, "0-$C_{1-8}$-alkyl" should read -- O-$C_{1-8}$-alkyl --.

Column 18, line 18, "0-$(CH_2)_2$" should read -- O-$(CH_2)_2$ --.

Column 19, line 44, "ON" should read -- CN --.

Column 35, line 63, "solution DCC" should read -- solution [begin new line] DCC --.

Column 36, line 31, "HBTU 0" should read -- HBTU O --.

Column 36, line 50, "TBTU 0" should read -- TBTU O --.

Column 43, line 34, "100 ml" should read -- 100 μl --.

Column 43, line 36, "92 ml" should read -- 92 μl --.

Column 50, line 40, "-2" should read -- ~2 --.

Column 50, line 67, "[m+H]$^+$" should read -- [M+H]$^+$ --.

Column 60, line 33, "100 ml" should read -- 100 μl --.

Column 60, line 48, "100 ml" should read -- 100 μl --.

Column 60, line 52, "FLUOstar™ BMG" should read -- FLUOstar™, BMG --.

Column 60, line 55, "50 ml" should read -- 50 μl --.

Column 62, line 43, "≦0.05" should read -- ≤0.05 --.

In the Claims

Column 67, line 50, ")-C(=O)het-" should read -- O-C(=O)het- --.

Column 68, line 13, "eacn" should read -- each --.

Column 68, line 28, "Y represents 0" should read -- Y represents O --.